(12) United States Patent
Alvaro et al.

(10) Patent No.: US 7,803,833 B2
(45) Date of Patent: Sep. 28, 2010

(54) COMPOUNDS

(75) Inventors: Giuseppe Alvaro, Verona (IT); David Amantini, Verona (IT); Markus Bergauer, Verona (IT); Francesca Bonetti, Verona (IT); Roberto Profeta, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 429 days.

(21) Appl. No.: 11/570,564

(22) PCT Filed: Oct. 6, 2006

(86) PCT No.: PCT/EP2006/009732
§ 371 (c)(1),
(2), (4) Date: Dec. 13, 2006

(87) PCT Pub. No.: WO2007/042240
PCT Pub. Date: Apr. 19, 2007

(65) Prior Publication Data
US 2008/0293753 A1    Nov. 27, 2008

(30) Foreign Application Priority Data

| Oct. 10, 2005 | (GB) | ................... | 0520578.6 |
| Nov. 11, 2005 | (GB) | ................... | 0523030.5 |
| Feb. 27, 2006 | (GB) | ................... | 0603897.0 |
| May 9, 2006 | (GB) | ................... | 0609159.9 |
| Sep. 20, 2006 | (GB) | ................... | 0618511.0 |

(51) Int. Cl.
*A61K 31/40* (2006.01)
*C07D 209/96* (2006.01)

(52) U.S. Cl. ..................... 514/409; 548/409

(58) Field of Classification Search ............... 514/409; 548/409
See application file for complete search history.

(56) References Cited

U.S. PATENT DOCUMENTS

| 5,236,957 A | 8/1993 | Dostert et al. |
| 6,201,016 B1 | 3/2001 | Cai et al. |
| 6,306,903 B1 | 10/2001 | Pevarello et al. |
| 2003/0055088 A1 | 3/2003 | Shao et al. |

| 2004/0097578 A1 | 5/2004 | Jolidon et al. |

FOREIGN PATENT DOCUMENTS

| WO | 00/57877 | 10/2000 |
| WO | 2004026827 A1 | 4/2004 |
| WO | 2004/083189 | 9/2004 |
| WO | 2004/092140 | 10/2004 |
| WO | 2004/094395 | 11/2004 |
| WO | 2005/000309 | 1/2005 |
| WO | 2005040108 A1 | 5/2005 |
| WO | 2006119390 A1 | 11/2006 |
| WO | 2006119451 A1 | 11/2006 |
| WO | 2006124865 A2 | 11/2006 |
| WO | 2008090114 A1 | 7/2008 |
| WO | 2008090115 A1 | 7/2008 |
| WO | 2008090116 A1 | 7/2008 |
| WO | 2008090117 A1 | 7/2008 |
| WO | 2008122546 A1 | 10/2008 |

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
Shao et al.; "Phenoxyphenyl Pyridines as Novel State-Dependent, High-Potency Sodium Channel Inhibitors"; Journal of Medicinal Chemistry; 2004; vol. 47, No. 17; pp. 4277-4285.

* cited by examiner

*Primary Examiner*—Kamal A Saeed
*Assistant Examiner*—Samantha L Shterengarts
(74) *Attorney, Agent, or Firm*—Kathryn L. Couiter

(57) ABSTRACT

The invention relates to quaternary α-aminocarboxyamide derivatives of formula (I), wherein $R^1$, $R^2$, $R^3$, $R^4$, $R^5$, $R^6$, X, q and n are as defined in claim 1, for treating diseases and conditions mediated by modulation of voltage-gated sodium channels.

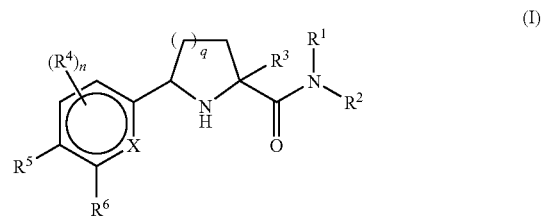

22 Claims, No Drawings

COMPOUNDS

This application is filed pursuant to 35 U.S.C. §371 as a U.S. National Phase Application of International Patent Application Ser. No. PCT/EP2006/009732 filed Oct. 6, 2006, which claims priority from Great Britain Application No. 0520578.6 filed in United Kingdom on Oct. 10, 2005, Great Britain Application No. 0523030.5 filed in the United Kingdom on Nov. 11, 2005, Great Britain Application No. 0603897.0 filed in the United Kingdom on Feb. 27, 2006, Great Britain Application No. 0609159.9 filed in the United Kingdom on May 9, 2006, and Great Britain Application No. 0618511.0 filed in the United Kingdom on Sep. 20, 2006, the content of each of which is incorporated herein by reference.

This invention relates to quaternary α-aminocarboxyamide derivatives. The invention also relates to the use of the derivatives in treating diseases and conditions mediated by modulation of voltage-gated sodium channels. In addition, the invention relates to compositions containing the derivatives and processes for their preparation.

Voltage-gated sodium channels are responsible for the initial phase of the action potential, which is a wave of electrical depolarisation usually initiated at the soma of the neuron and propagated along the nerve axon to the terminals. At the terminals, the action potential triggers the influx of calcium and the release of neurotransmitter. Drugs, such as lidocaine, that block voltage-gated sodium channels are used as local anaesthetics. Other sodium channel blockers, such as lamotrigine and carbamazepine are used to treat epilepsy. In the latter case, partial inhibition of voltage-gated sodium channels reduces neuronal excitability and reduces seizure propagation. In the case of local anaesthetics, regional block of sodium channels on sensory neurons prevents the conduction of painful stimuli. A key feature of these drugs is their use-dependent mechanism of action. The drugs are thought to stabilise an inactivated configuration of the channel that is adopted rapidly after the channel opens. This inactivated state provides a refractory period before the channel returns to its resting (closed) state ready to be reactivated. As a result, use-dependent sodium channel blockers retard the firing of neurons at high frequency, for example in response to painful stimuli, and will help to prevent repetitive firing during periods of prolonged neuronal depolarisation that might occur, for example, during a seizure. Action potentials triggered at low frequencies, for example in the heart, will not be significantly affected by these drugs, although the safety margin differs in each case, since at high enough concentrations each of these drugs is capable of blocking the resting or open states of the channels.

The voltage-gated sodium channel family is made up of 10 subtypes, four of which are brain specific, NaV1.1, 1.2, 1.3 and 1.6. Of the other subtypes, NaV1.4 is found only in skeletal muscle, NaV1.5 is specific to cardiac muscle, and NaV1.7, 1.8, and 1.9 are found predominantly in sensory neurons. The hypothesised binding site for use-dependent sodium channel blockers is highly conserved between all the subtypes. As a result, drugs such as lidocaine, lamotrigine and carbamazepine do not distinguish between the subtypes. However, selectivity can be achieved as a result of the different frequencies at which the channels normally operate.

Drugs that block voltage-gated sodium channels in a use-dependent manner are also used in the treatment of bipolar disorder, either to reduce symptoms of mania or depression, or as mood stabilisers to prevent the emergence of mood episodes. Clinical and preclinical evidence also suggests that use-dependent sodium channel blockers may help to reduce the symptoms of schizophrenia. For example, lamotrigine has been shown to reduce symptoms of psychosis induced by ketamine in healthy human volunteers, and furthermore, studies in patients suggest that the drug can augment the antipsychotic efficacy of some atypical antipsychotic drugs, such as clozapine or olanzapine. It is hypothesised that efficacy in these psychiatric disorders may result in part from a reduction of excessive glutamate release. The reduction in glutamate release is thought to be a consequence of use-dependent sodium channel inhibition in key brain areas, such as the frontal cortex. However, interaction with voltage-gated calcium channels may also contribute to the efficacy of these drugs.

International published patent application WO05/000309 (Ionix Pharmaceuticals Limited) discloses the use of compounds of formula (I), wherein $R_1$ is an organic substituent, $X_1$ and $X_2$ are direct bonds or spacer moieties, Ar is aryl or heteroaryl and Y is a substituted aminoalkyl group or a heteroaryl-, heterocyclyl- or phenyl-containing moiety:

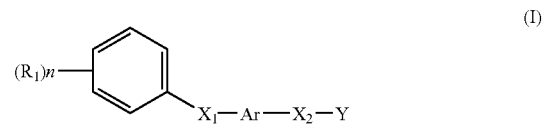

Such compounds are inhibitors of sensory neurone specific sodium channels and are said to be useful in the treatment of chronic and acute pain, tinnitus, bowel disorders, bladder dysfunction and demyelinating diseases.

International published patent application WO04/083189 (Merck & Co.) discloses biaryl substituted triazole compounds of formula (I), (II) and (III) as sodium channel blockers:

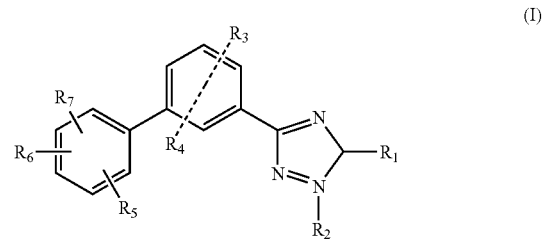

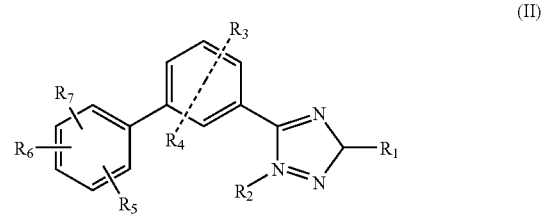

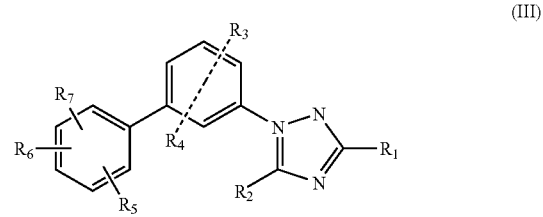

Such compounds are said to be useful in the treatment of conditions associated with sodium channel activity including, for example, acute pain, chronic pain, visceral pain, epilepsy, irritable bowel syndrome, depression and others.

International published patent application WO04/092140 (Merck & Co.) discloses biaryl substituted pyrazoles of formula (I), (II), (III) and (IV) as sodium channel blockers:

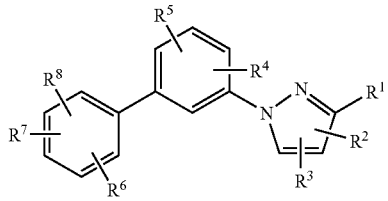

(I)

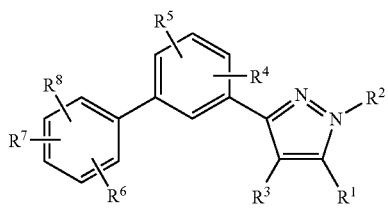

(II)

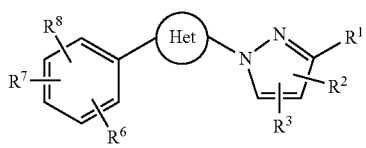

(III)

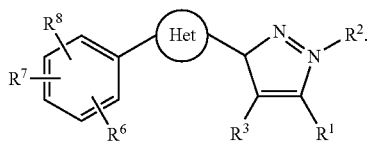

(IV)

The compounds are said to be useful in the treatment of conditions including acute pain, chronic pain, visceral pain, inflammatory pain and neuropathic pain.

International published patent application WO04/094395 (Merck & Co.) discloses biaryl substituted thiazoles, oxazoles and imidazoles of formula (I) as sodium channel blockers:

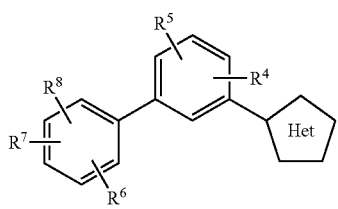

(I)

The compounds are said to be useful in the treatment of conditions including acute pain, chronic pain, visceral pain, inflammatory pain and neuropathic pain.

International patent application WO04/026826 (F. Hoffman La Roche AG) discloses 4-pyrrolidinophenyl-benzyl ether derivatives of formula (I):

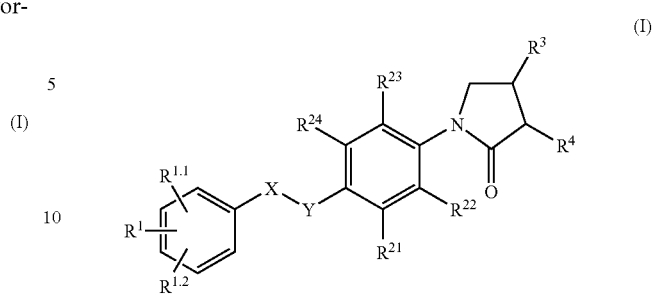

(I)

The compounds are said to be monoamine oxidase B inhibitors and are said to be useful in the treatment of conditions such as Alzheimer's disease or senile dementia.

The object of the present invention is to identify alternative compounds which modulate voltage-gated sodium channels.

In one embodiment, the compounds will be use dependent sodium channel inhibitors.

In another embodiment, the compounds will be a subtype NaV1.3 sodium channel use dependent inhibitors.

In another embodiment, the compounds will be use dependent sodium channel inhibitors which have a suitable developability profile on oral administration, for example in terms of exposure (Cmax) and/or bioavailability.

In another embodiment, the present invention provides compounds which modulate voltage-gated sodium channels and which additionally exhibit Monoamine Oxidase B inhibition.

In a still further embodiment, the present invention provides compounds which modulate voltage-gated sodium channels and which don't exhibit Monoamine Oxidase B inhibition.

According to a first aspect, the invention provides a compound of formula (I), a pharmaceutically acceptable salt, solvate, or prodrug thereof:

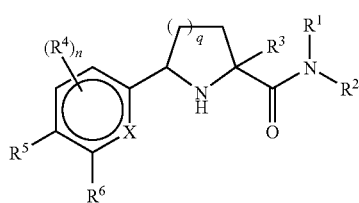

(I)

wherein $R^1$ and $R^2$ are independently hydrogen, $C_{1-6}$alkyl or $C_{3-6}$cycloalkyl$C_{1-6}$alkyl; or $R^1$ and $R^2$, together with the nitrogen to which they are attached, may form an unsubstituted 3-, 4-, 5- or 6-membered saturated ring;

$R^3$ is $C_{1-6}$alkyl, $C_{1-6}$haloalkyl, $C_{1-3}$alkoxy$C_{1-3}$alkyl or $C_{1-3}$haloalkoxy$C_{1-3}$alkyl;

or $R^1$ and $R^3$, together with the interconnecting atoms, form a saturated or unsaturated 4- to 6-membered ring;

X is carbon or nitrogen;

n is 0, 1 or 2, wherein when present each $R^4$ is independently selected from the list consisting of $C_{1-3}$alkyl, halogen, cyano, halo$C_{1-3}$alkyl, hydroxy, $C_{1-3}$alkoxy and $C_{1-3}$haloalkoxy;

q is 1 or 2;

either $R^5$ or $R^6$ is —O—$R^7$ or —OCH$_2$$R^7$, wherein the other $R^5$ or $R^6$ is hydrogen or $R^4$; and wherein $R^7$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

Unless otherwise indicated, any alkyl group is straight or branched regardless of whether it forms part of another group, for example, alkoxy, haloalkyl and haloalkoxy.

As used herein, a haloalkyl group means an alkyl group substituted by one or more halogen atoms. A haloalkoxy group should be similarly construed.

The term 5- or 6-membered aromatic heterocyclic ring means a heterocyclyl group containing one or more carbon atoms, one or more hydrogen atoms and one or more heteroatoms such as nitrogen, oxygen and sulfur; the carbon and heteroatoms being interconnected to form a ring. For example furyl, thienyl, pyrrolyl, imidazolyl, oxazolyl, thiazolyl, pyrazolyl, isoxazolyl, isothiazolyl, oxadiazolyl, triazolyl, thiadiazolyl, pyridyl, pyridazinyl, pyrimidinyl, pyrazinyl and tetrazolyl.

Halo means fluoro, chloro, bromo or iodo.

In a further embodiment, the invention provides a compound of formula (I), a pharmaceutically acceptable salt, solvate, or prodrug thereof:

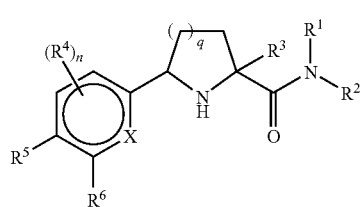

(I)

wherein $R^1$ and $R^2$ are independently hydrogen, $C_{1-6}$alkyl or $C_{3-6}$cycloalkyl$C_{1-6}$alkyl; or such $R^1$ and $R^2$, together with the nitrogen to which they are attached, may form an unsubstituted 3-, 4-, 5- or 6-membered saturated ring;

$R^3$ is $C_{1-6}$alkyl, $C_{1-6}$haloalkyl, $C_{1-3}$alkenyl, $C_{1-3}$alkoxy$C_{1-3}$alkyl, $C_{1-3}$haloalkoxy$C_{1-3}$alkyl or $(CH_2)_t$OH;

or such $R^1$ and $R^3$, together with the interconnecting atoms, form a saturated or unsaturated 5- to 7-membered ring, with the proviso that there is only one heteroatom in the ring, which must be nitrogen;

X is carbon or nitrogen;

n is 0, 1 or 2, wherein when present each $R^4$ is independently selected from the list consisting of $C_{1-3}$alkyl, halogen, cyano, halo$C_{1-3}$alkyl, hydroxy, $C_{1-3}$alkoxy and $C_{1-3}$haloalkoxy, q is 1 or 2;

t is 1 or 2;

either $R^5$ or $R^6$ is —O—$R^7$ or OCH$_2$$R^7$, wherein the other $R^5$ or $R^6$ is hydrogen or $R^4$; and wherein $R^7$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In an embodiment, $R^1$ and $R^2$ are independently H or $C_{1-6}$alkyl. In an alternative embodiment, $R^1$ and $R^2$ are both H. In another embodiment $R^1$ and $R^2$ are independently H or $C_{1-3}$alkyl. In a further embodiment $R^1$ and $R^2$ are independently H or methyl.

In an embodiment, $R^3$ is $C_{1-6}$alkyl, $C_{1-3}$alkoxy$C_{1-3}$alkyl, or $(CH_2)_q$OH. In a further embodiment, $R^3$ is $C_{1-3}$alkyl. In an alternative embodiment, $R^3$ is methyl, methoxymethyl or CH$_2$OH. In another alternative embodiment, $R^3$ is methyl.

In an embodiment, $R^1$ and $R^3$, together with the interconnecting atoms, form a saturated or unsaturated 5-, 6-, or 7-membered ring with the proviso that the ring does not contain two contiguous heteroatoms. In an alternative embodiment, $R^1$ and $R^3$, together with the interconnecting atoms, form a 5-membered pyrrolidinone ring. In another alternative embodiment, $R^1$ and $R^3$, together with the interconnecting atoms, form a 5-membered pyrrolidinone ring, and $R^2$ is $C_{1-6}$alkyl; or $R^2$ is $C_{1-3}$alkyl; or $R^2$ is methyl.

In a further embodiment, $R^1$ and $R^3$, together with the interconnecting atoms, form a 6-membered piperidinone ring.

In a still further embodiment, $R^1$ and $R^3$, together with the interconnecting atoms, form a 7-membered unsaturated azepinone ring.

In an embodiment, X is carbon.

In an embodiment, q is 1.

In an embodiment, t is 1.

In an embodiment, n is 0 or 1.

In an embodiment, n is 1 and $R^4$ is $C_{1-3}$alkoxy. In an alternative embodiment, n is 1 and $R^4$ is methoxy.

In an embodiment, $R^5$ is —O—$R^7$ or —OCH$_2$$R^7$, and $R^6$ is hydrogen or $R^4$; and wherein $R^7$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In another embodiment, $R^5$ is —O—$R^7$ or —OCH$_2$$R^7$, and $R^6$ is hydrogen or $R^4$; and wherein $R^7$ is either a phenyl ring optionally substituted by one or more groups independently selected from the list consisting of $C_{1-3}$alkyl, halogen, cyano, halo$C_{1-3}$alkyl, hydroxy, $C_{1-3}$alkoxy and $C_{1-3}$haloalkoxy.

In a yet another embodiment, $R^5$ is —O—$R^7$ or —OCH$_2$$R^7$, and $R^6$ is hydrogen or $R^4$; and wherein $R^7$ is either a phenyl ring optionally substituted by one group independently selected from the list consisting of $C_{1-3}$alkyl, halogen, cyano, halo$C_{1-3}$alkyl, hydroxy, $C_{1-3}$alkoxy and $C_{1-3}$haloalkoxy.

In a still further another embodiment, $R^5$ is —O—$R^7$ or —OCH$_2$$R^7$, and $R^6$ is hydrogen or $R^4$; and wherein $R^7$ is either a phenyl ring optionally substituted in the ortho position by one group independently selected from the list consisting of $C_{1-3}$alkyl, halogen, cyano, halo$C_{1-3}$alkyl, hydroxy, $C_{1-3}$alkoxy and $C_{1-3}$haloalkoxy.

In yet another embodiment, $R^5$ is —OCH$_2$phenyl optionally substituted by one or more groups independently selected from the list consisting of $C_{1-3}$alkyl, halogen, cyano, halo $C_{1-3}$alkyl, hydroxy, $C_{1-3}$alkoxy and $C_{1-3}$haloalkoxy. In yet another embodiment, $R^5$ is —OCH$_2$phenyl substituted by halogen or cyano.

In a further embodiment, $R^5$ is —OCH$_2$phenyl substituted by one fluorine atom.

In yet another embodiment, $R^5$ is —Ophenyl optionally substituted by one or more groups independently selected from the list consisting of $C_{1-3}$alkyl, halogen, cyano, halo $C_{1-3}$alkyl, hydroxy, $C_{1-3}$alkoxy and $C_{1-3}$haloalkoxy. In yet another embodiment, $R^5$ is —OCH$_2$phenyl substituted by halogen or cyano.

In yet another embodiment, $R^5$ is —Ophenyl optionally substituted by one cyano group.

In another embodiment, $R^5$ is phenoxy, fluorophenoxy or cyanophenoxy. In a further embodiment $R^5$ is 2-cyano phenoxy.

In another embodiment, $R^5$ is benzyloxy, fluorobenzyloxy or cyanobenzyloxy. In a further embodiment $R^5$ is 2-fluorobenzyloxy, 3-fluorobenzyloxy or 2-cyanobenzyloxy.

In an embodiment, the compounds of formula (I) are selected from the list consisting of:
(5R)-5-(4-{[(2-fluorophenyl)methyl]oxy}phenyl)-2-methyl-L-prolinamide;
(5R)-5-(4-{[(2-cyanophenyl)methyl]oxy}phenyl)-2-methyl-L-prolinamide;
(5R)-5-{4-[(2-cyanophenyl)oxy]phenyl}-2-methyl-L-prolinamide;
(5S)-2-methyl-5-{4-[(phenylmethyl)oxy]phenyl}-D-prolinamide;
(5S)-5-(4-{[(2-fluorophenyl)methyl]oxy}phenyl)-2-methyl-O-prolinamide; and
(2R,5R)-2-(4-{[(2-fluorophenyl)methyl]oxy}phenyl)-1,7-diazaspiro[4.4]nonan-6-one;

or a pharmaceutically acceptable salt, solvate or prodrug thereof.

In a further embodiment the compound of formula (I) is:
(5R)-5-(4-{[(2-fluorophenyl)methyl]oxy}phenyl)-2-methyl-L-prolinamide; or
(5S)-5-(4-{[(2-fluorophenyl)methyl]oxy}phenyl)-2-methyl-D-prolinamide;

or a pharmaceutically acceptable salt, solvate or prodrug thereof.

In a still further embodiment the compound of formula (I) is (5R)-5-(4-{[(2-fluorophenyl)methyl]oxy}phenyl)-2-methyl-L-prolinamide; or a pharmaceutically acceptable salt, solvate or prodrug thereof.

In an embodiment, the compounds of formula (I) are selected from the list consisting of:
(5R)-5-(4-{[(2-fluorophenyl)methyl]oxy}phenyl)-2-methyl-L-prolinamide;
(5R)-5-(4-{[(2-cyanophenyl)methyl]oxy}phenyl)-2-methyl-L-prolinamide;
(5R)-5-{4-[(2-cyanophenyl)oxy]phenyl}-2-methyl-L-prolinamide;
(5S)-2-methyl-5-{4-[(phenylmethyl)oxy]phenyl}-D-prolinamide;
(5S)-5-(4-{[(2-fluorophenyl)methyl]oxy}phenyl)-2-methyl-D-prolinamide;
(2R,5R)-2-(4-{[(2-fluorophenyl)methyl]oxy}phenyl)-1,7-diazaspiro[4.4]nonan-6-one; and
(2R,5R)-2-(4-{[(2-fluorophenyl)methyl]oxy}phenyl)-7-methyl-1,7-diazaspiro[4.4]nonan-6-one or a pharmaceutically acceptable salt, solvate or prodrug thereof.

In an embodiment, the compounds of formula (I) are selected from the list consisting of:
(5R)-5-(4-{[(2-fluorophenyl)methyl]oxy}phenyl)-2-methyl-L-prolinamide;
(5R)-5-(4-{[(2-cyanophenyl)methyl]oxy}phenyl)-2-methyl-L-prolinamide;
(5R)-5-{4-[(2-cyanophenyl)oxy]phenyl}-2-methyl-L-prolinamide;
(5S)-2-methyl-5-{4-[(phenylmethyl)oxy]phenyl}-D-prolinamide;
(5S)-5-(4-{[(2-fluorophenyl)methyl]oxy}phenyl)-2-methyl-D-prolinamide;
(2R,5R)-2-(4-{[(2-fluorophenyl)methyl]oxy}phenyl)-1,7-diazaspiro[4.4]nonan-6-one;
2-[({4-[(2R,5R)-6-oxo-1,7-diazaspiro[4.4]non-2-yl]phenyl}oxy)methyl]benzonitrile;
2-({4-[(2R,5R)-6-oxo-1,7-diazaspiro[4.4]non-2-yl]phenyl}oxy)benzonitrile;
(2R,5R)-2-(4-{[(2-fluorophenyl)methyl]oxy}phenyl)-7-methyl-1,7-diazaspiro[4.4]nonan-6-one;
(2R,5R)-2-(3-{[(2-fluorophenyl)methyl]oxy}phenyl)-1,7-diazaspiro[4.4]nonan-6-one;
(2R,5R)-2-(3-{[(2-fluorophenyl)methyl]oxy}phenyl)-7-methyl-1,7-diazaspiro[4.4]nonan-6-one;
(2R,5R)-2-(4-{[(2-fluorophenyl)methyl]oxy}phenyl)-1,7-diazaspiro[4.6]undec-9-en-6-one;
(2R,5S)-2-(4-{[(2-fluorophenyl)methyl]oxy}phenyl)-1,7-diazaspiro[4.5]decan-6-one;
(2S,5S)-2-(4-{[(2-fluorophenyl)methyl]oxy}phenyl)-1,7-diazaspiro[4.5]decan-6-one;
(5R)-5-[4-{[(2-fluorophenyl)methyl]oxy}-3-(methyloxy)phenyl]-2-methyl-L-prolinamide;
(5R)-5-[4-{[(2-fluorophenyl)methyl]oxy}-3-(methyloxy)phenyl]-2-[(methyloxy)methyl]-L-prolinamide;
(5R)-5-(4-{[(2-fluorophenyl)methyl]oxy}phenyl)-2-[(methyloxy)methyl]-L-prolinamide;
(5R)-5-(4-{[(2-fluorophenyl)methyl]oxy}phenyl)-2-(hydroxymethyl)-L-prolinamide;
(2S,5S)-2-(4-{[(2-fluorophenyl)methyl]oxy}phenyl)-1,7-diazaspiro[4.4]nonan-6-one;
(5R,7R)-7-(4-{[(2-Fluorophenyl)methyl]oxy}phenyl)-2,6-diazaspiro[4.5]decan-1-one; and
(5S,7S)-7-(4-{[(2-Fluorophenyl)methyl]oxy}phenyl)-2,6-diazaspiro[4.5]decan-1-one;

or a pharmaceutically acceptable salt, solvate, or prodrug thereof.

In another embodiment, the compounds of formula (I) are selected from the group consisting of hydrochloride salts, or solvates thereof, of the compounds listed below:
(5R)-5-(4-{[(2-fluorophenyl)methyl]oxy}phenyl)-2-methyl-L-prolinamide;
(5R)-5-(4-{[(2-cyanophenyl)methyl]oxy}phenyl)-2-methyl-L-prolinamide;
(5R)-5-{4-[(2-cyanophenyl)oxy]phenyl}-2-methyl-L-prolinamide;
(5S)-2-methyl-5-{4-[(phenylmethyl)oxy]phenyl}-D-prolinamide;
(5S)-5-(4-{[(2-fluorophenyl)methyl]oxy}phenyl)-2-methyl-D-prolinamide;
(2R,5R)-2-(4-{[(2-fluorophenyl)methyl]oxy}phenyl)-1,7-diazaspiro[4.4]nonan-6-one;
2-[({4-[(2R,5R)-6-oxo-1,7-diazaspiro[4.4]non-2-yl]phenyl}oxy)methyl]benzonitrile;
2-({4-[(2R,5R)-6-oxo-1,7-diazaspiro[4.4]non-2-yl]phenyl}oxy)benzonitrile;
(2R,5R)-2-(4-{[(2-fluorophenyl)methyl]oxy}phenyl)-7-methyl-1,7-diazaspiro[4.4]nonan-6-one;
(2R,5R)-2-(3-{[(2-fluorophenyl)methyl]oxy}phenyl)-1,7-diazaspiro[4.4]nonan-6-one;
(2R,5R)-2-(3-{[(2-fluorophenyl)methyl]oxy}phenyl)-7-methyl-1,7-diazaspiro[4.4]nonan-6-one;
(2R,5R)-2-(4-{[(2-fluorophenyl)methyl]oxy}phenyl)-1,7-diazaspiro[4.6]undec-9-en-6-one;
(2R,5S)-2-(4-{[(2-fluorophenyl)methyl]oxy}phenyl)-1,7-diazaspiro[4.5]decan-6-one;
(2S,5S)-2-(4-{[(2-fluorophenyl)methyl]oxy}phenyl)-1,7-diazaspiro[4.5]decan-6-one;

(5R)-5-[4-{[(2-fluorophenyl)methyl]oxy}-3-(methyloxy)phenyl]-2-methyl-L-prolinamide;
(5R)-5-[4-{[(2-fluorophenyl)methyl]oxy}-3-(methyloxy)phenyl]-2-[(methyloxy)methyl]-L-prolinamide;
(5R)-5-(4-{[(2-fluorophenyl)methyl]oxy}phenyl)-2-[(methyloxy)methyl]-L-prolinamide;
(5R)-5-(4-{[(2-fluorophenyl)methyl]oxy}phenyl)-2-(hydroxymethyl)-L-prolinamide;
(2S,5S)-2-(4-{[(2-fluorophenyl)methyl]oxy}phenyl)-1,7-diazaspiro[4.4]nonan-6-one;
(5R,7R)-7-(4-{[(2-Fluorophenyl)methyl]oxy}phenyl)-2,6-diazaspiro[4.5]decan-1-one; and
(5S,7S)-7-(4-{[(2-Fluorophenyl)methyl]oxy}phenyl)-2,6-diazaspiro[4.5]decan-1-one.

In a further embodiment the compound of formula (I) is:
(5R)-5-(4-{[(2-fluorophenyl)methyl]oxy}phenyl)-2-methyl-L-prolinamide;
(2R,5R)-2-(4-{[(2-fluorophenyl)methyl]oxy}phenyl)-1,7-diazaspiro[4.4]nonan-6-one;
(2R,5R)-2-(4-{[(2-fluorophenyl)methyl]oxy}phenyl)-7-methyl-1,7-diazaspiro[4.4]nonan-6-one;
(5R)-5-(4-{[(2-fluorophenyl)methyl]oxy}phenyl)-2-[(methyloxy)methyl]-L-prolinamide;
(5R)-5-(4-{[(2-fluorophenyl)methyl]oxy}phenyl)-2-(hydroxymethyl)-L-prolinamide;

or a pharmaceutically acceptable salt, solvate or prodrug thereof.

In another embodiment, the compounds of formula (I) are selected from the group consisting of hydrochloride salts, or solvates thereof, of the compounds listed below:
(5R)-5-(4-{[(2-fluorophenyl)methyl]oxy}phenyl)-2-methyl-L-prolinamide;
(2R,5R)-2-(4-{[(2-fluorophenyl)methyl]oxy}phenyl)-1,7-diazaspiro[4.4]nonan-6-one;
(2R,5R)-2-(4-{[(2-fluorophenyl)methyl]oxy}phenyl)-7-methyl-1,7-diazaspiro[4.4]nonan-6-one;
(5R)-5-(4-{[(2-fluorophenyl)methyl]oxy}phenyl)-2-[(methyloxy)methyl]-L-prolinamide;
(5R)-5-(4-{[(2-fluorophenyl)methyl]oxy}phenyl)-2-(hydroxymethyl)-L-prolinamide.

In another further embodiment the compound of formula (I) is:
(2R,5R)-2-(4-{[(2-fluorophenyl)methyl]oxy}phenyl)-7-methyl-1,7-diazaspiro[4.4]nonan-6-one or a pharmaceutically acceptable salt, solvate or prodrug thereof.

In a still further embodiment the compound of formula (I) is:
(2R,5R)-2-(4-{[(2-fluorophenyl)methyl]oxy}phenyl)-1,7-diazaspiro[4.4]nonan-6-one or a pharmaceutically acceptable salt, solvate or prodrug thereof.

In another embodiment, the compound of formula (I) is selected in the list consisting of:
(2R,5R)-2-(4-{[(2-fluorophenyl)methyl]oxy}phenyl)-1,7-diazaspiro[4.4]nonan-6-one hydrochloride;
(5R)-5-(4-{[(2-fluorophenyl)methyl]oxy}phenyl)-2-methyl-L-prolinamide; or a solvate thereof.

In yet another embodiment the compound of formula (I) is:
(2R,5R)-2-(4-{[(2-fluorophenyl)methyl]oxy}phenyl)-7-methyl-1,7-diazaspiro[4.4]nonan-6-one hydrochloride; or
(2R,5R)-2-(4-{[(2-fluorophenyl)methyl]oxy}phenyl)-7-methyl-1,7-diazaspiro[4.4]nonan-6-one tosylate;

or a solvate thereof.

In yet another embodiment the compound of formula (I) is selected from the group consisting of:
(5R)-5-(4-{[(2-fluorophenyl)methyl]oxy}phenyl)-2-methyl-L-prolinamide;
(5R)-5-(4-{[(2-cyanophenyl)methyl]oxy}phenyl)-2-methyl-L-prolinamide;
(5S)-2-methyl-5-{4-[(phenylmethyl)oxy]phenyl}-D-prolinamide;
(5S)-5-(4-{[(2-fluorophenyl)methyl]oxy}phenyl)-2-methyl-D-prolinamide;
(5R)-5-(4-{[(2-fluorophenyl)methyl]oxy}phenyl)-2-[(methyloxy)methyl]-L-prolinamide;
(5R)-5-(4-{[(2-fluorophenyl)methyl]oxy}phenyl)-2-(hydroxymethyl)-L-prolinamide;

or a pharmaceutically acceptable salt, solvate or prodrug thereof.

In a still another embodiment the compound of formula (I) is selected from the group consisting of:
(5R)-5-{4-[(2-cyanophenyl)oxy]phenyl}-2-methyl-L-prolinamide;
(2R,5R)-2-(4-{[(2-fluorophenyl)methyl]oxy}phenyl)-1,7-diazaspiro[4.4]nonan-6-one;
2-[({4-[(2R,5R)-6-oxo-1,7-diazaspiro[4.4]non-2-yl]phenyl}oxy)methyl]benzonitrile;
2-({4-[(2R,5R)-6-oxo-1,7-diazaspiro[4.4]non-2-yl]phenyl}oxy)benzonitrile hydrochloride;
(2R,5R)-2-(3-{[(2-fluorophenyl)methyl]oxy}phenyl)-1,7-diazaspiro[4.4]nonan-6-one;
(2R,5R)-2-(3-{[(2-fluorophenyl)methyl]oxy}phenyl)-7-methyl-1,7-diazaspiro[4.4]nonan-6-one;
(2R,5R)-2-(4-{[(2-fluorophenyl)methyl]oxy}phenyl)-1,7-diazaspiro[4.6]undec-9-en-6-one;
(2R,5S)-2-(4-{[(2-fluorophenyl)methyl]oxy}phenyl)-1,7-diazaspiro[4.5]decan-6-one;
(5R)-5-[4-{[(2-fluorophenyl)methyl]oxy}-3-(methyloxy)phenyl]-2-methyl-L-prolinamide;
(5R)-5-[4-{[(2-fluorophenyl)methyl]oxy}-3-(methyloxy)phenyl]-2-[(methyloxy) methyl]-L-prolinamide;
(2S,5S)-2-(4-{[(2-fluorophenyl)methyl]oxy}phenyl)-1,7-diazaspiro[4.4]nonan-6-one;
(5R,7R)-7-(4-{[(2-fluorophenyl)methyl]oxy}phenyl)-2,6-diazaspiro[4.5]decan-1-one;

or a pharmaceutically acceptable salt, solvate or prodrug thereof.

For the avoidance of doubt, unless otherwise indicated, the term "substituted" means substituted by one or more defined groups. In the case where groups may be selected from a number of alternative groups, the selected groups may be the same or different.

For the avoidance of doubt, the term "independently" means that where more than one substituent is selected from a number of possible substituents, those substituents may be the same or different.

The pharmaceutically or veterinarily acceptable salts of the compounds of the invention which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

Hereinafter, compounds and their pharmaceutically acceptable salts, solvates and prodrugs defined in any aspect of the invention (except intermediate compounds in chemical processes) are referred to as "compounds of the invention".

The pharmaceutically acceptable solvates of the compounds of the invention include the hydrates thereof.

Also included within the scope of the compound and various salts of the invention are polymorphs thereof.

The compounds of the invention may possess at least two or more chiral centres and so exist in a number of stereoisomeric forms. All stereoisomers and mixtures thereof are included in the scope of the present invention.

It will be appreciated by a person skilled in the art that four diastereoisomers can be envisaged for compounds of formula (I), i.e. compounds of formula (Ia), (Ib), (Ic) and (Id):

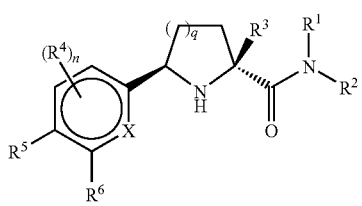

(Ia)

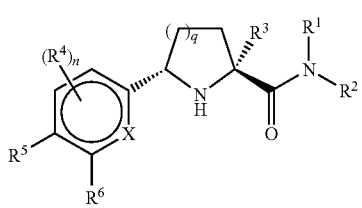

(Ib)

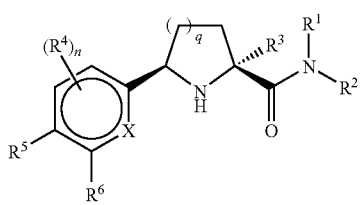

(Ic)

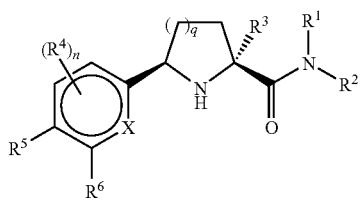

(Id)

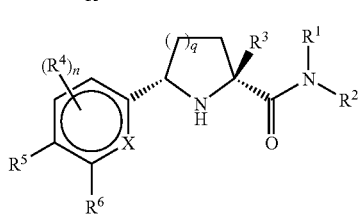

wherein $R^1$, $R^2$, $R^3$, $R^4$, $R^5$, $R^6$, X, n and q are as defined above.

In one embodiment, the present invention provides compounds of formula (Ia)

(Ia)

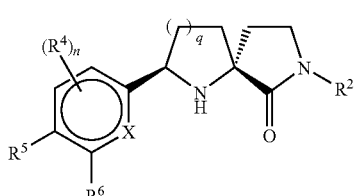

wherein $R^1$, $R^2$, $R^3$, $R^4$, $R^5$, $R^6$, X, n and q are as defined above, or pharmaceutically acceptable salts, solvates or prodrugs thereof.

In another embodiment, the present invention provides a compound of formula (Ie)

(Ie)

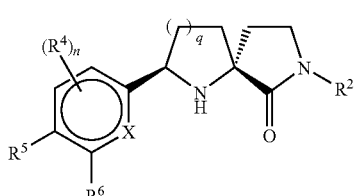

wherein $R^2$, $R^4$, $R^5$, $R^6$, X, n and q are as defined above, or pharmaceutically acceptable salts, solvates or prodrugs thereof.

In a yet another embodiment, the present invention provides a compound of formula (Ih)

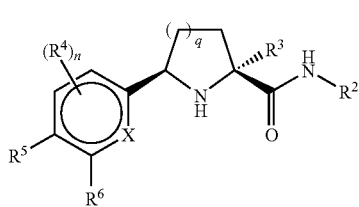

(Ih)

wherein $R^2$, $R^3$, $R^4$, $R^5$, $R^6$, X, n and q are as defined above or pharmaceutically acceptable salts, solvates or prodrug thereof.

Diastereoisomers of compounds of the invention or of intermediates thereof may be obtained according to methods well known in the literature, for example by preparative HPLC or by chromatographic purifications. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

The compounds of the invention may exist in one or more tautomeric forms. All tautomers and mixtures thereof are included in the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples hereafter using appropriate isotopic variations of suitable reagents.

Compounds of the invention may be prepared in a variety of ways. In the following reaction schemes and hereafter, unless otherwise stated $R^1$ to $R^7$, n, q and X are as defined in the first aspect. These processes form further aspects of the invention.

Throughout the specification, general formulae are designated by Roman numerals (I), (II), (III), (IV) etc. Subsets of these general formulae are defined as (Ia), (Ib), (Ic) etc. . . . (IVa), (IVb), (IVc) etc.

Hydrochloride salts of compounds of formula (I) may be prepared according to Reaction Scheme 1 by reacting compounds of formula (II) with an excess (such as 2.5 equivalents) of acetyl chloride and methanol. Typical reaction conditions comprise reacting (II) in a suitable aprotic solvent (such as EtOAc) at room temperature.

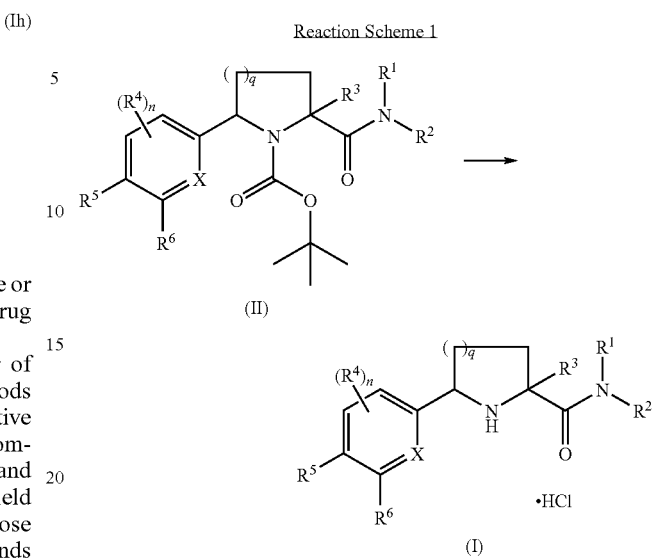

Compounds of formula (IIa), i.e. compounds of formula (II) wherein $R^5$ is —$OCH_2R^7$ may be prepared according to Reaction Scheme 2 by reacting compounds of formula (III) with an excess (eg 1.5 eq) of $R^7CH_2Y$ (where Y is a suitable leaving group—for examples see J. March, Advanced Organic Chemistry: reactions, mechanisms, and structure, John Wiley & Sons (1992), $4^{th}$ Ed., p 352). Typical reaction conditions comprise reaction in a suitable solvent (such as acetonitrile or DMF) at a temperature ranging from room temperature to solvent reflux. It will be appreciated that compounds of formula (II) where $R^6$ is —$OCH_2R^7$, can be prepared by analogous methods starting from the corresponding hydroxy compound. Compounds of formula $R^7CH_2Y$ are either commercially available or can be synthesized via methodologies known in the literature.

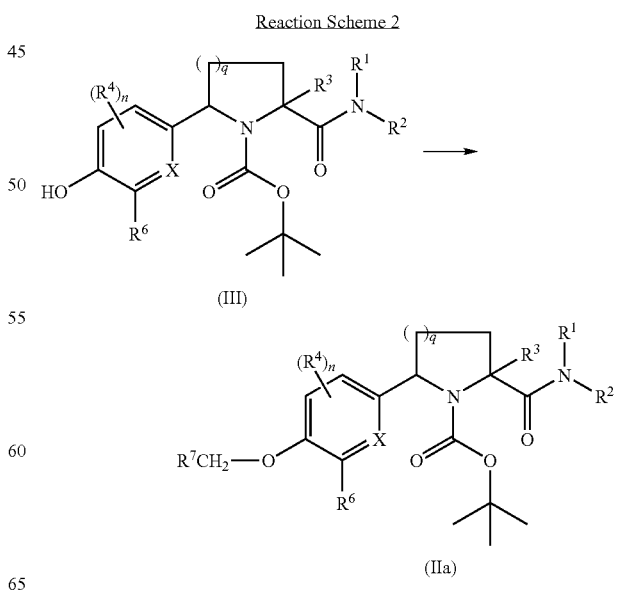

Compounds of formula (IIb), i.e. compounds of formula (II) wherein $R^5$ is —$OR^7$ can be prepared according to Reaction Scheme 3 by reacting compounds of formula (III) with $R^7$—$B(OH)_2$. Typical reaction conditions comprise the use of a suitable catalyst (such as copper (II) acetate) and a suitable base (such as triethylamine or pyridine) in a halogenated hydrocarbon solvent (such as DCM) at a temperature ranging from room temperature to solvent reflux. Compounds of formula $R^7$—$B(OH)_2$ are either commercially available or may be synthesised via methodologies known in the literature.

Alternatively compounds of formula (IIb), where $R^7$ contains one or more electron withdrawing substituents, can be obtained according to Reaction Scheme 3 by reacting compounds of formula (III) with $R^7$—F in the presence of a suitable base (such as potassium carbonate) in a suitable solvent (such as DMF) by heating with microwave irradiation. Compounds of formula $R^7$—F are either commercially available or may be synthesised via methodologies known in the literature.

It will be appreciated that compounds of formula (II) wherein $R^6$ is —$OR^7$, can be prepared by analogous methods starting from the corresponding hydroxy compound.

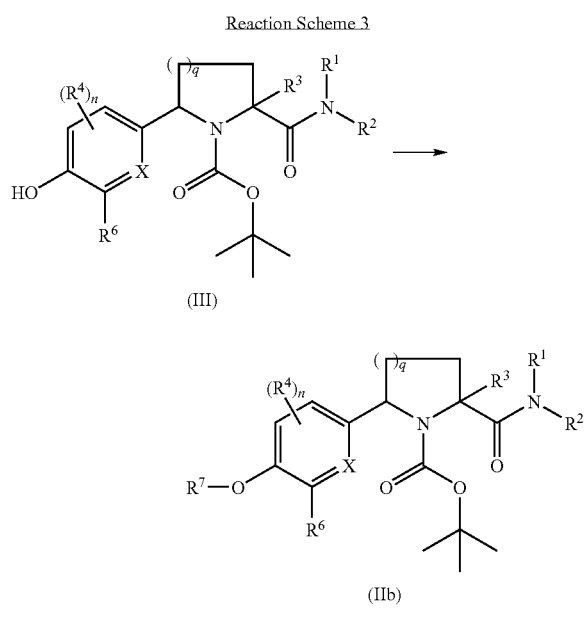

Compounds of formula (IIc), i.e. compounds of formula (II) wherein $R^3$ and $R^1$ together with the interconnecting atoms form a saturated or unsaturated 5- to 7-membered ring (i.e. m is 2, 3 or 4 and optionally including 1 or 2 unsaturations) and $R^2$ is other than hydrogen, may be prepared according to Reaction Scheme 4 by reacting compounds of formula (IId), i.e. compounds of formula (II) wherein $R^3$ and $R^1$ together with the interconnecting atoms form a saturated or unsaturated 5- to 7-membered ring (i.e. m is 2, 3 or 4 and optionally including 1 or 2 unsaturations) and $R^2$ is hydrogen, with a suitable base (such as sodium hydride) followed by treatment with a compound of formula $R^2$—Y (wherein $R^2$ is lower alkyl and Y is a suitable leaving group) in an aprotic solvent (such as DMF) at a temperature ranging from 0° C. to room temperature.

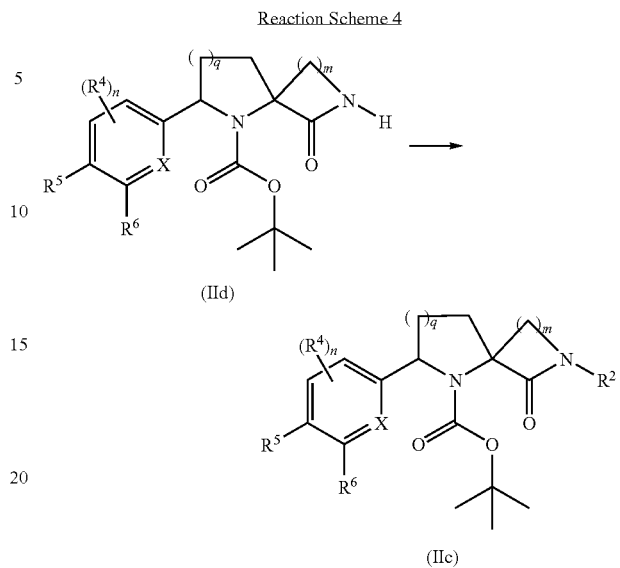

Compounds of formula (III) may be prepared according to Reaction Scheme 5 by reacting compounds of formula (IV) with palladium metal on carbon under a hydrogen atmosphere (such as 1 atmosphere) in a suitable alcoholic solvent (such as methanol) at room temperature.

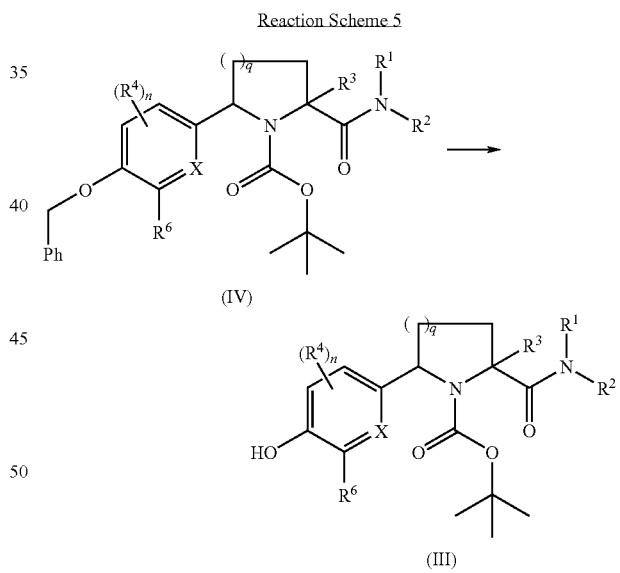

Compounds of formula (IVa), i.e. compounds of formula (IV) wherein $R^3$ and $R^1$ together with the interconnecting atoms form a saturated or unsaturated 5- to 7-membered ring (i.e. m is 2, 3 or 4 and optionally including 1 or 2 unsaturations) and $R^2$ is other than hydrogen, may be prepared according to Reaction Scheme 6 by reacting compounds of formula (V) with a suitable base (such as sodium hydride) followed by treatment with a compound of formula $R^2$—Y (wherein $R^2$ is lower alkyl and Y is a suitable leaving group) in an aprotic solvent (such as DMF) at a temperature ranging from 0° C. to room temperature.

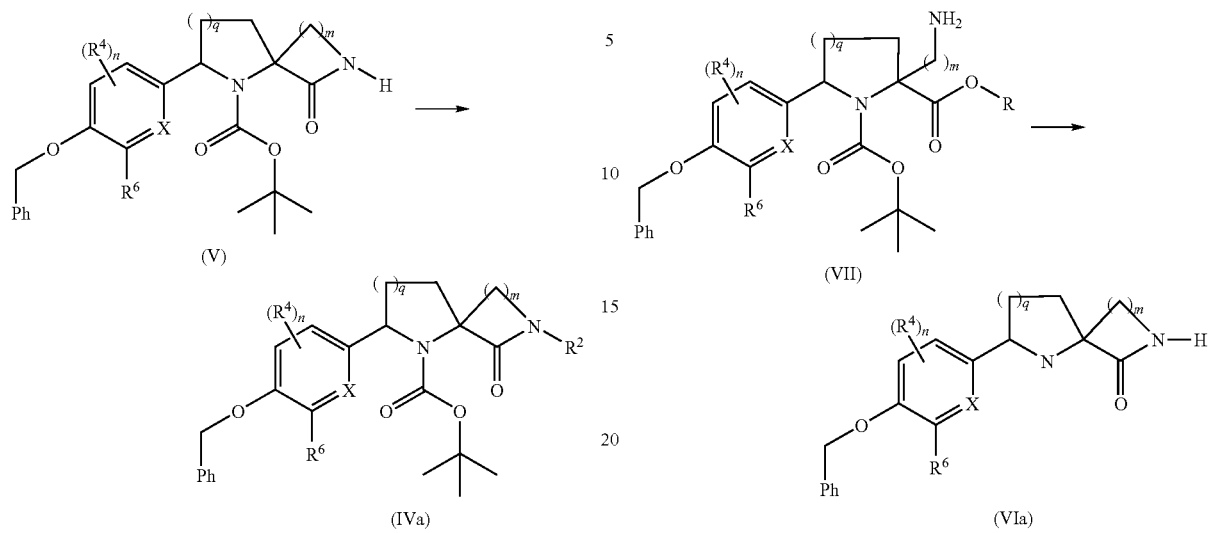

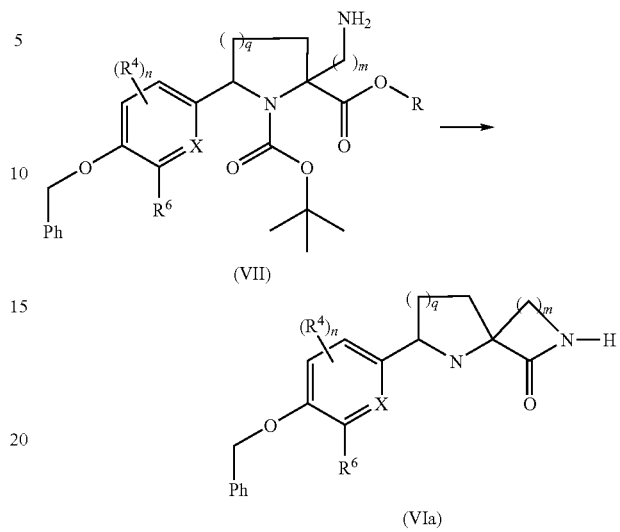

Compounds of formula (V), wherein $R^3$ and $R^1$ together with the interconnecting atoms form a saturated or unsaturated 5- to 7-membered ring (i.e. m is 2, 3 or 4 and optionally including 1 or 2 unsaturations), may be obtained according to Reaction Scheme 7 starting from compounds of formula (VI). Typical reaction conditions comprise treatment with a reagent suitable to transfer a t-butoxycarbonyl group onto an amine (such as di-tert-butyl dicarbonate) in a mixture of solvents (such as THF/aq NaHCO₃/t-BuOH) at room temperature.

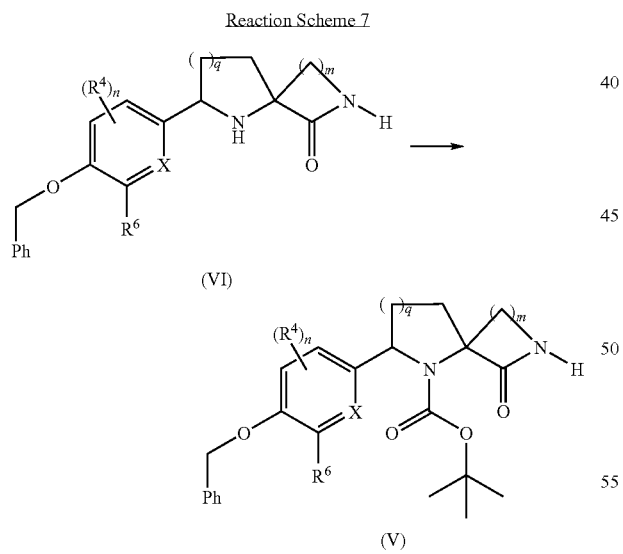

Compounds of formula (VIa), i.e. compounds of formula (VI) wherein $R^3$ and $R^1$ together with the interconnecting atoms form a saturated 5- to 7-membered ring (i.e. m is 2, 3 or 4) and $R^2$ is hydrogen, may be obtained according to Reaction Scheme 8 by reacting compounds of formula (VII), wherein R is $C_{1-3}$alkyl, with trifluoroacetic acid in a halogenated hydrocarbon solvent (such as DCM) at a temperature ranging from 0° C. to room temperature.

Compounds of formula (VII) may be obtained according to Reaction Scheme 9 by reacting compounds of formula (VII) with Raney Nickel under elevated pressure (such as 7 atmos) in an alcoholic solvent (such as methanol) at room temperature.

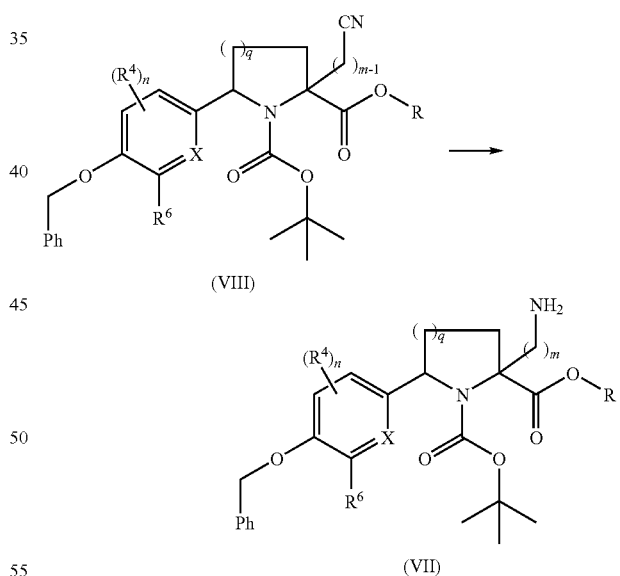

Alternatively compounds of formula (IIIa), i.e. compounds of formula (III) wherein $R^3$ and $R^1$ together with the interconnecting atoms form a saturated 5- to 7-membered ring (i.e. m is 2, 3 or 4) and $R^2$ is hydrogen, may be obtained according to Reaction Scheme 10 by reacting compounds of formula (VIII) wherein R is $C_{1-3}$alkyl, with Raney Nickel under an elevated; pressure of hydrogen (7 atmos) in an alcoholic solvent (such as methanol) at room temperature for 15 hours and then, after filtering off the catalyst, heating the solution at the reflux temperature of methanol for 5 hours.

Reaction Scheme 10

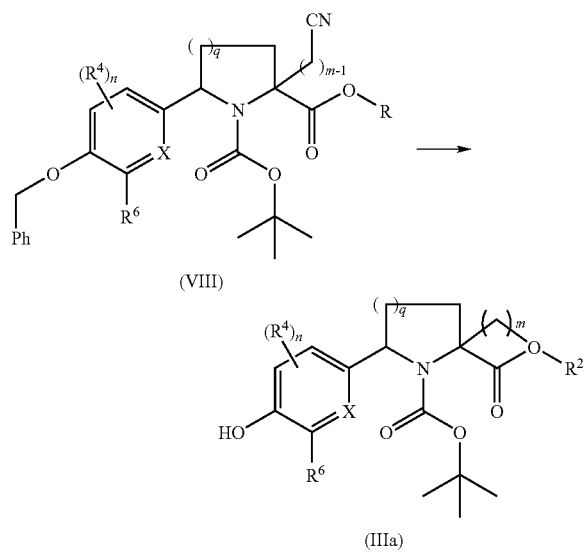

Compounds of formula (VIII) may be prepared according to Reaction Scheme 11, by reacting compounds of formula (IX) with lithium hexamethyldisilazide followed by addition of a compound of formula $Y(CH_2)_{m-1}CN$ (where Y is a leaving group, such as Br) in an aprotic solvent (such as THF) at low temperature (such as −78° C.).

Reaction Scheme 11

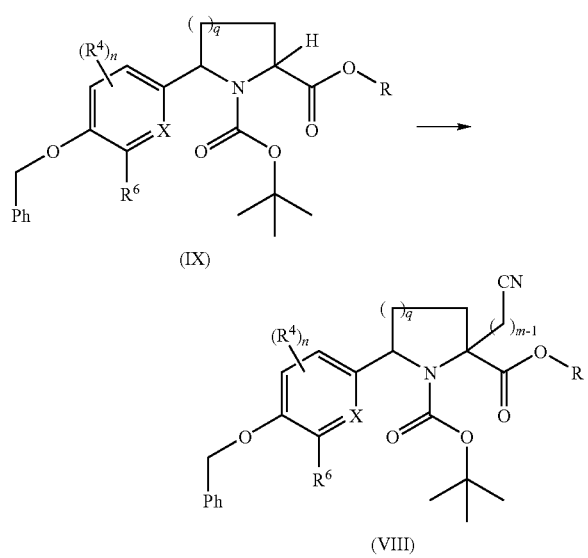

Compounds of formula (Va), wherein $R^3$ and $R^1$ together with the interconnecting atoms form an unsaturated 5-7-membered ring (i.e. r is 0, 1 or 2), may be obtained according to Reaction Scheme 12 by reacting compounds of formula (X), with TFA in a halogenated hydrocarbon (such as dichloromethane) at 40° C., followed by treatment of the resulting material with a reagent suitable to transfer a t-butoxycarbonyl group onto an amine (such as di-tert-butyl dicarbonate) in a mixture of solvents (THF/aq $NaHCO_3$/t-BuOH) at room temperature.

Reaction Scheme 12

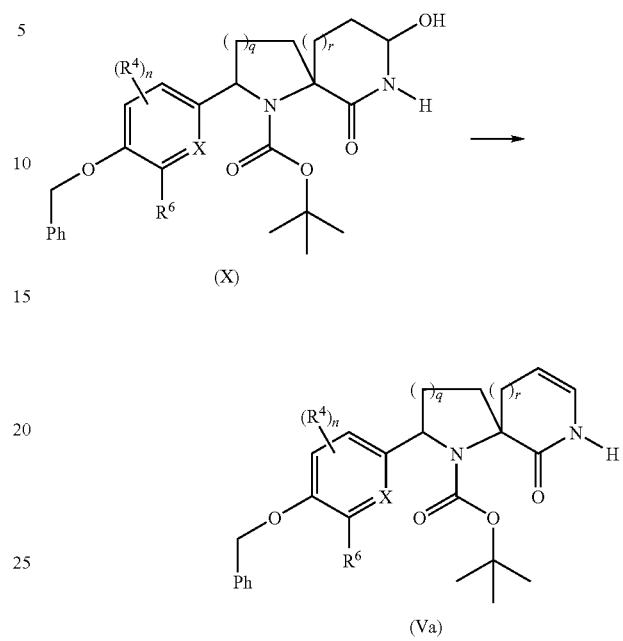

Compounds of formula (X) may be obtained according to Reaction Scheme 13 by reacting compounds of formula (XI) with osmium tetroxide and sodium periodate in a solvent mixture (such as water/THF) at room temperature.

Reaction Scheme 13

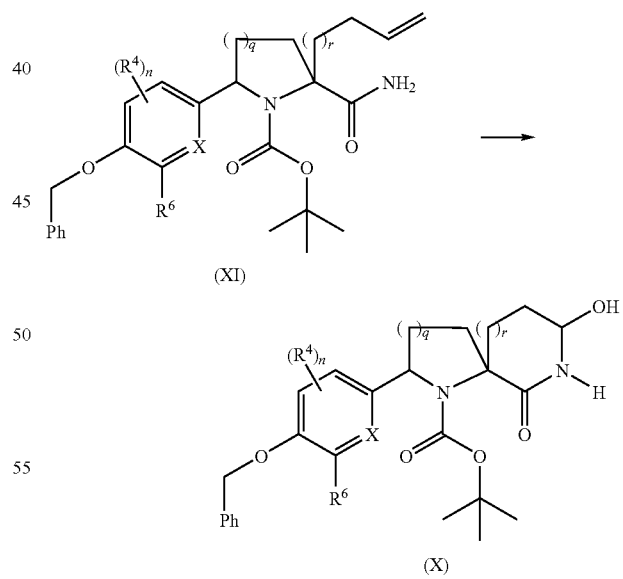

Compounds of formula (XI) may be obtained according to Reaction Scheme 14 by reacting compounds of formula (XII) with HMDS. Typical reaction conditions comprise reacting (XII) with TBTU and a base (such as diisopropyloethylamine) in a suitable solvent (such as DMF) followed by addition of HMDS at room temperature.

Reaction Scheme 14

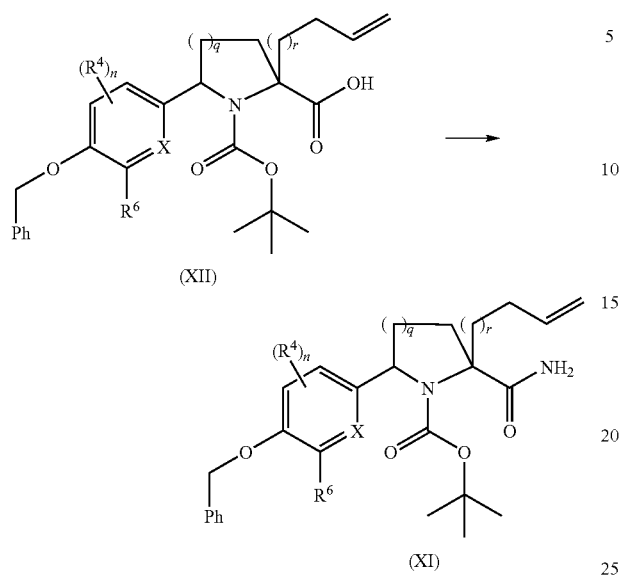

(XII)

(XI)

Compounds of formula (XII) may be prepared according to Reaction Scheme 15 by reacting compounds of formula (XIII), wherein R is $C_{1-3}$alkyl, with a suitable base (such as LiOH) in a THF/water mixture (such as 1:1) at room temperature.

Reaction Scheme 15

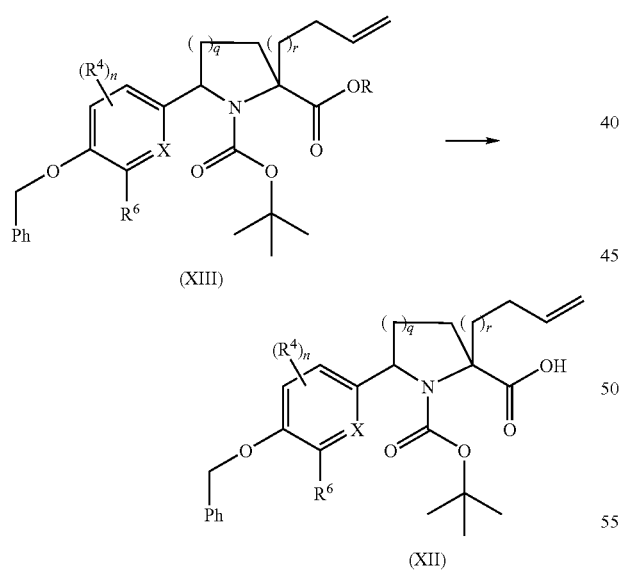

(XIII)

(XII)

Compounds of formula (XIII) may be prepared according to Reaction Scheme 16 by treating compounds of formula (IX) with lithium hexamethyldisilazide and $CH_2\!\!=\!\!CHCH_2(CH_2)_rY$ (where Y is a suitable leaving group) in an aprotic solvent (such as THF) at low temperature (such as $-78°$ C.). Compounds of formula $CH_2\!\!=\!\!CHCH_2(CH_2)_rY$ are commercially available or may be synthesized via methodologies known in the literature.

Reaction Scheme 16

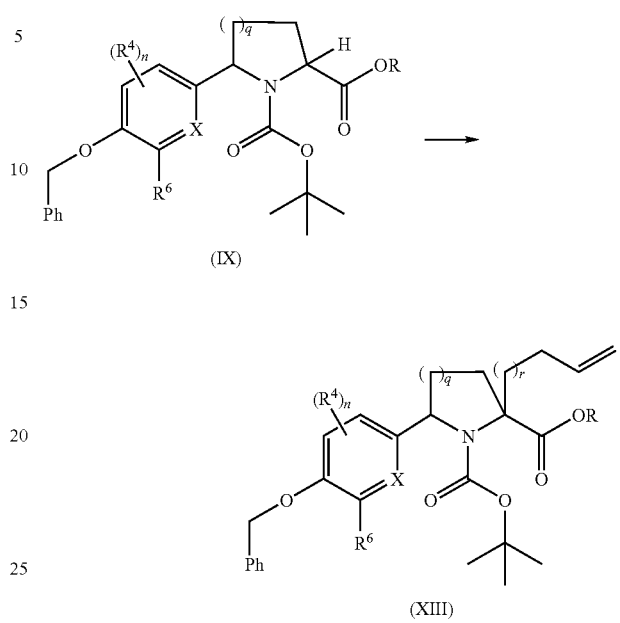

(IX)

(XIII)

Compounds of formula (IX) may be prepared according to Reaction Scheme 17. Typical reaction conditions comprise reaction of compounds of formula (XIV) with a reagent suitable to transfer a tert-butoxycarbonyl group onto an amine (such as di-tert-butyl dicarbonate) in an aprotic solvent (such as THF) at room temperature.

Reaction Scheme 17

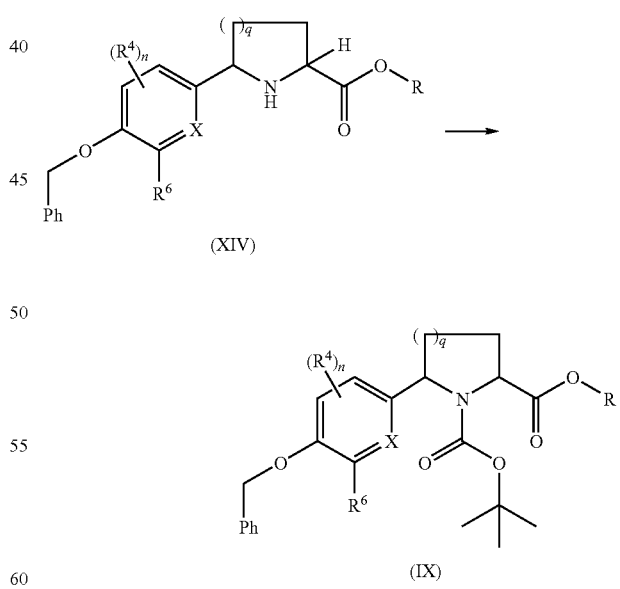

(XIV)

(IX)

Compounds of formula (XIV) may be prepared according to Reaction Scheme 18 by reacting compounds of formula (XV) with $PtO_2$ under an atmosphere of hydrogen at high pressure (such as 2 atm) in a suitable alcoholic solvent (such as methanol) at room temperature.

Reaction Scheme 18

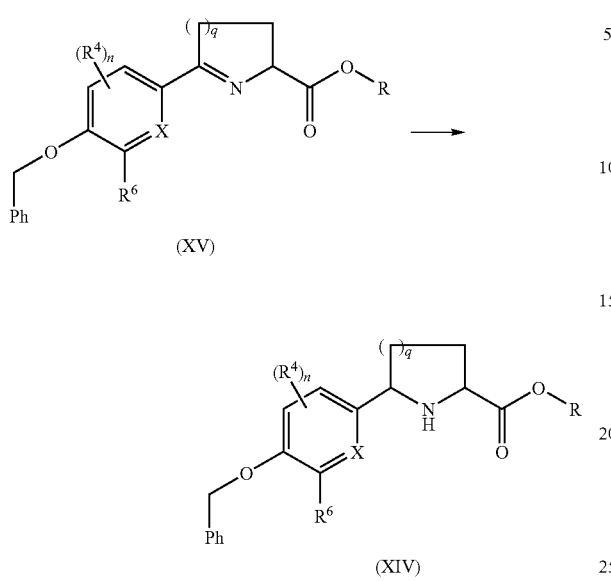

(XV)

(XIV)

Compounds of formula (XV) may be prepared according to Reaction Scheme 19 by reacting compounds of formula (XVI) with trifluoroacetic acid in a halogenated hydrocarbon solvent (such as DCM) at low temperature (such as 0° C.).

Reaction Scheme 19

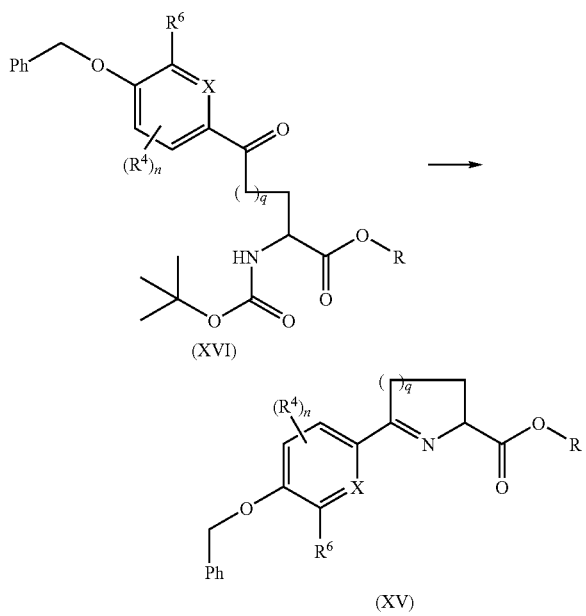

(XVI)

(XV)

Compounds of formula (XVI) may be obtained according to Reaction Scheme 20. Typical reaction conditions comprise reacting compounds of formula (XVII) with a suitable metallated compound of formula (XVIII) where M is for example MgZ (where Z is Cl, Br or I) or lithium in a suitable solvent (such as diethyl ether or THF) at low temperature (such as −78° C.).

Reaction Scheme 20

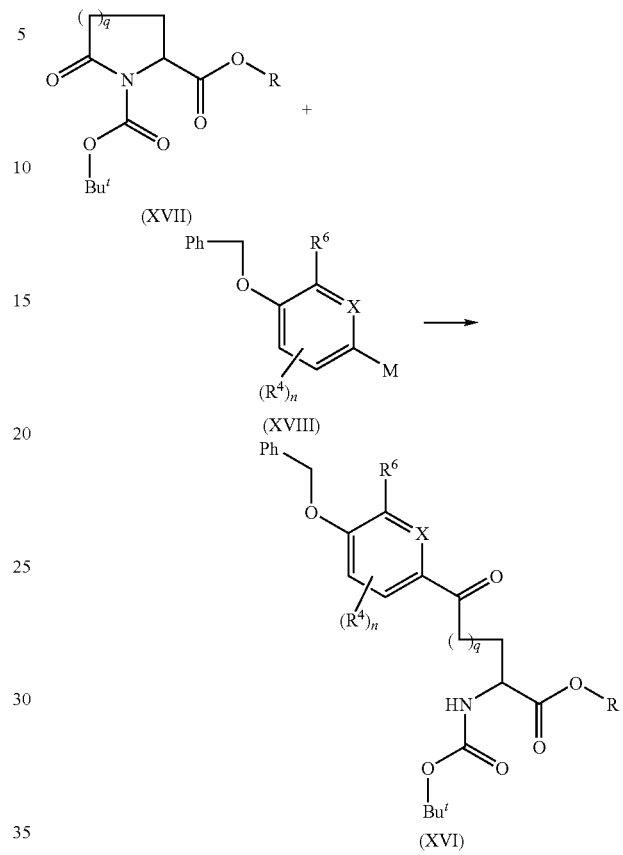

(XVII)

(XVIII)

(XVI)

The compounds of formula (XVIIIa), i.e. compounds of general formula (XVIII) wherein M is MgZ (where Z is Cl, Br or I), may be generated according to Reaction Scheme 21 via Grignard methodologies known in the literature by reacting the appropriate compound of general formula (XIX) with magnesium metal in ether. Typical reaction conditions comprise reaction at low temperature (ranging from −78° C. to 0° C.) in a suitable solvent (such as ether or THF).

Reaction Scheme 21

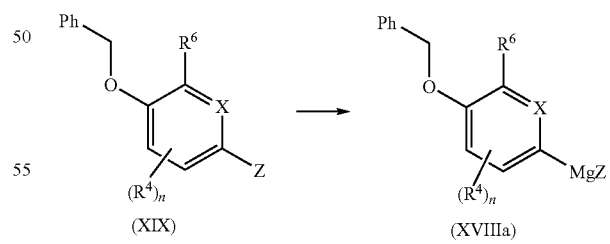

(XIX)

(XVIIIa)

The compounds of general formula (XVIIIb), i.e. compounds of formula (XVIII) wherein M is lithium, may be generated according to Reaction Scheme 22 via methodologies widely known in the literature by reacting the appropriate compound of general formula (XIX) with n-butyllithium. Typical reaction conditions comprise reaction at low temperature (ranging from −78° C. to 0° C.) in a suitable solvent (such as ether or THF).

Reaction Scheme 22

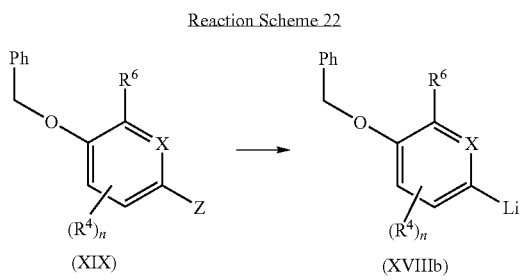

Compounds of general formula (XIX) are either commercially available or may be synthesized following the procedures described in Reaction Scheme 23 by reacting compounds of formula (XX) with benzyl bromide in the presence of a suitable base (such as potassium carbonate) in a suitable solvent (such as acetonitrile or DMF) at a temperature ranging from room temperature to reflux.

Reaction Scheme 23

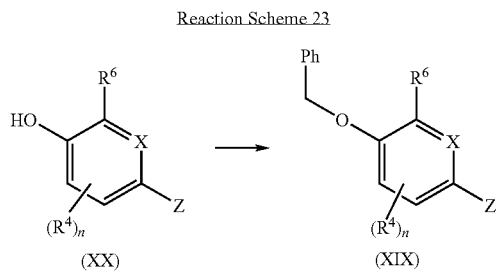

It will be appreciated that the reactions shown in schemes 2 to 23 are applicable to the preparation of compounds of formula (I) where $R^6$ is —O—$R^7$ or —OCH$_2$$R^7$ as appropriate.

Compounds of formula (XVII) may be prepared according to Reaction Scheme 24 by reacting compounds of formula (XXI) with a reagent suitable to transfer a BOC group onto an amine (such as di-tert-butyl dicarbonate) in the presence of a base (such as 4-DMAP) in an aprotic solvent (such as DCM) at room temperature.

Reaction Scheme 24

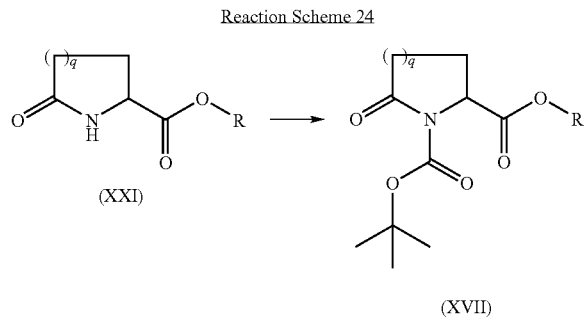

Compounds of general formula (XXI) are either commercially available or can be obtained via synthetic procedures known in the literature (S. Huang, J. Nelson, D. Weller, *Synthetic Communications*, 20, 3485-96 (1989)).

Alternatively, hydrochloric salts of compounds of formula (Ie), i.e. compounds of formula (I) wherein $R^3$ and $R^1$ together with the interconnecting atoms form a saturated 5-membered ring and $R^2$ is other than hydrogen, may be prepared according to Reaction Scheme 25 by treatment of compounds of formula (Ie) with an excess of HCl in the appropriate solvent (such as DCM/IPA).

Reaction Scheme 25

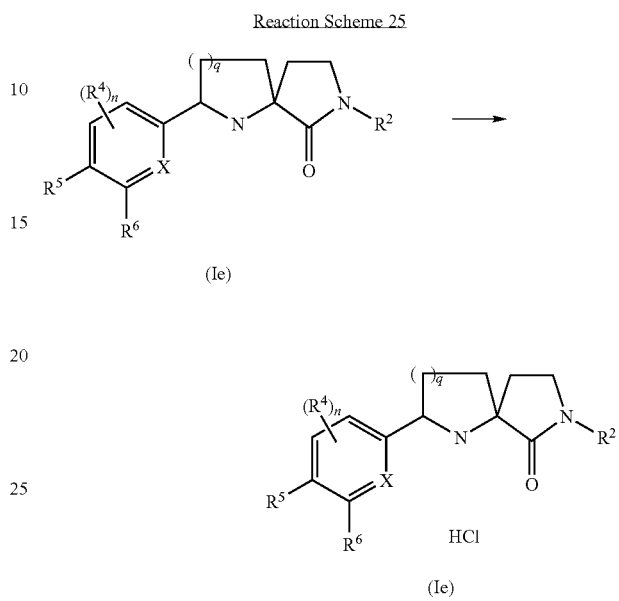

Compounds of formula (Ie), i.e. compounds of formula (I) wherein $R^3$ and $R^1$ together with the interconnecting atoms form a saturated 5-membered ring and $R^2$ is other than hydrogen, may be prepared according to Reaction Scheme 26 by reacting compounds of formula (XXII) with hydrochloric acid under appropriate conditions (such as in IPA/MeOH at room temperature) followed by treatment with a suitable base (such as aqueous ammonia).

Reaction Scheme 26

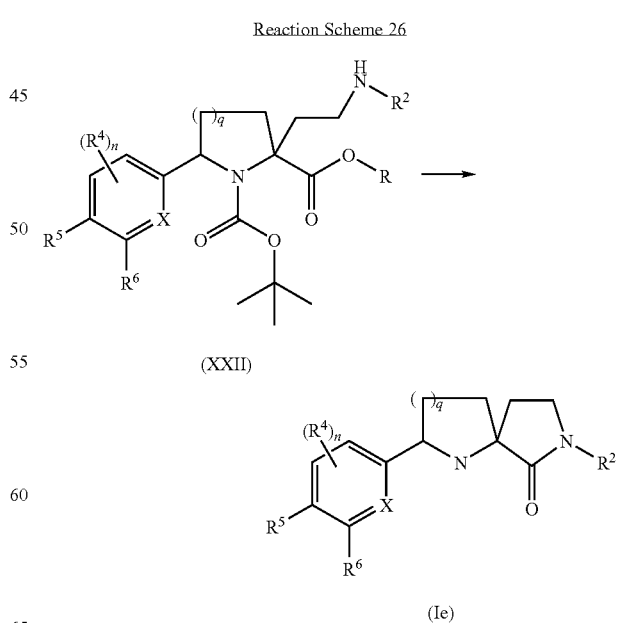

Compounds of formula (XXII) may be prepared according to Reaction Scheme 27 by reductive amination of compounds of formula (XXIII) with $R^2NH_2$ in an appropriate solvent (such as MeOH) and in the presence of a suitable reducing agent (such as $NaBH(OAc)_3$).

Reaction Scheme 27

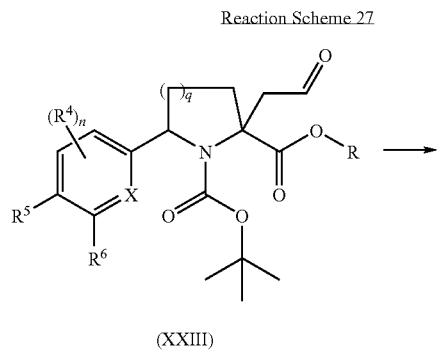

(XXIII)

(XXII)

Compounds of formula (XXIII) may be prepared according to Reaction Scheme 28 by reaction of compounds of formula (XXIV) with $K_2OsO_4$ and N-methylmorpholine-N-oxide at room temperature in an appropriate solvent (such as acetone/water) and followed by treatment of the product obtained with $NaIO_4$.

Alternative conditions to obtain compounds of formula (XXIII) comprise reaction of compounds of formula (XXIV) with ozone gas at low temperature in a suitable solvent (such as methanol) followed by addition of a reducing agent (for example, dimethylsulfide or zinc).

Reaction Scheme 28

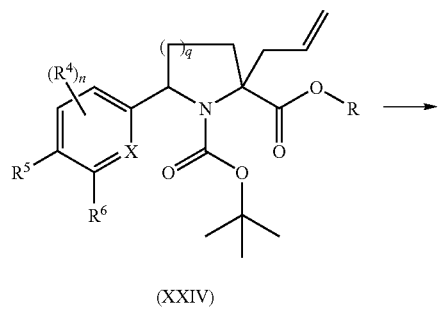

(XXIV)

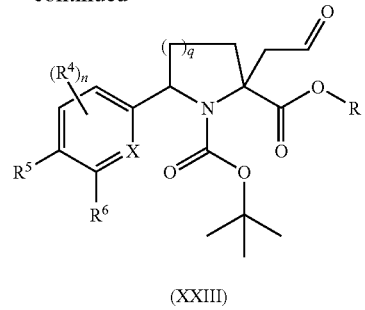

(XXIII)

Compounds of formula (XXIV) may be prepared according to Reaction Scheme 29 by treatment of compounds of formula (XXV) with an allyl halide (such as allyl bromide) followed by treatment with a suitable base (such as lithium bis-trimethylsilyldisilazide solution in THF) at low temperature (suitably −30° C.) in an appropriate solvent (such as THF).

Reaction Scheme 29

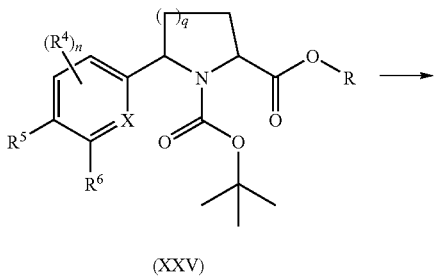

(XXV)

(XXIV)

Compounds of formula (XXV) may be prepared according to Reaction Scheme 30 by treatment of compounds of formula (XXVI) with di-tert-butyl-dicarbonate in a suitable solvent (such as EtOAc) at low temperature (such as 0° C.).

Reaction Scheme 30

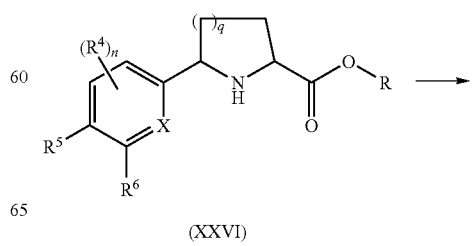

(XXVI)

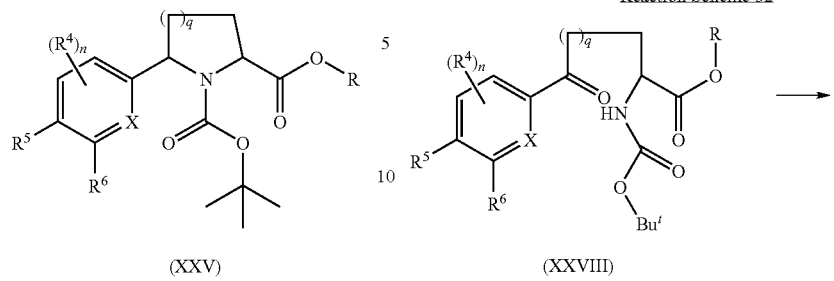

(XXV) (XXVIII)

Compounds of formula (XXVI) can be prepared according to Reaction Scheme 31 by reacting compounds of formula (XXVII) with Pt/C under an atmosphere of hydrogen at elevated pressure (such as 2 atm) in a suitable solvent (such as EtOAc) at room temperature.

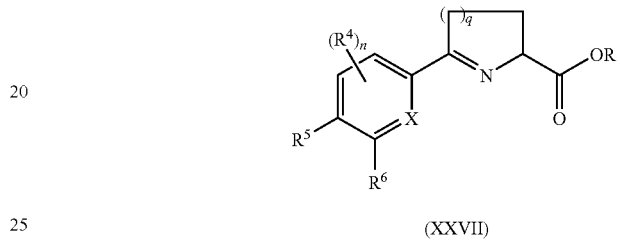

(XXVII)

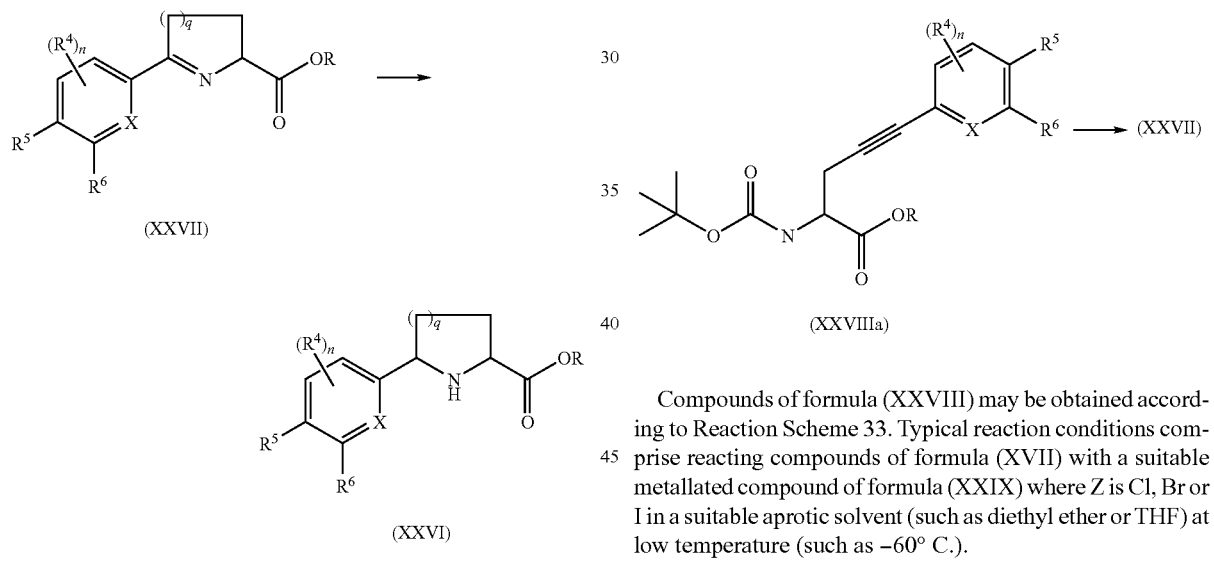

Reaction Scheme 31

(XXVII)

(XXVIIIa)

(XXVI)

Compounds of formula (XXVIII) may be obtained according to Reaction Scheme 33. Typical reaction conditions comprise reacting compounds of formula (XVII) with a suitable metallated compound of formula (XXIX) where Z is Cl, Br or I in a suitable aprotic solvent (such as diethyl ether or THF) at low temperature (such as −60° C.).

Compounds of formula (XXVII) may be prepared according to Reaction Scheme 32 by reacting compounds of formula (XXVIII) with trifluoroacetic acid in a halogenated hydrocarbon solvent (such as DCM) at a temperature ranging from 0° C. to room temperature. As an alternative, compounds of formula (XXVII) with q=1 may be prepared from compounds of formula (XXVIIIa) using a metal catalyst such as silver-(I)-triflate in N,N-dimethylformamide, tetrahydrofuran, acetonitrile or solvents having similar physicochemical properties at temperatures ranging from 0° C. to reflux. Compounds of formula (XXVIIa) are readily prepared by analogous procedures to that described in the literature (van Esseveldt et al, Journal of Organic Chemistry 2005, 70, 1791-1795 and references cited therein).

Reaction Scheme 33

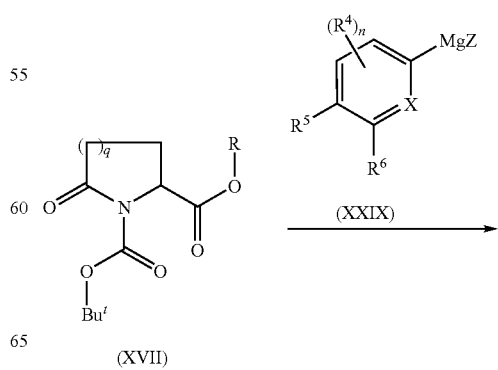

(XVII) (XXIX)

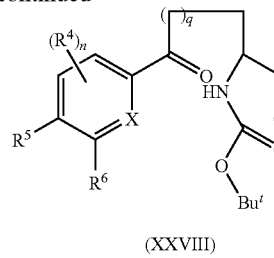

(XXVIII)

The compounds of general formula (XXIX) may be generated according to Reaction Scheme 34 by reacting the appropriate compound of general formula (XXX) with magnesium metal in THF. Typical reaction conditions comprise reaction at a temperature ranging from room temperature to 65° C., in a suitable solvent (such as ether or THF).

Reaction Scheme 34

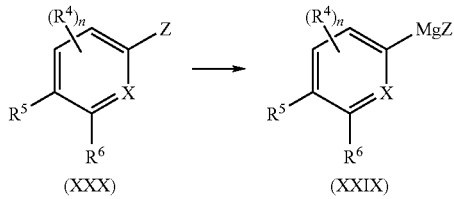

Compounds of general formula (XXX), are either commercially available or may be synthesized following the procedures described in Reaction Scheme 35 by reacting compounds of formula (XX) as above defined with the appropriate benzyl bromide (XXXI) in the presence of a suitable base (such as potassium carbonate) in a suitable solvent (such as acetone) at a temperature ranging from room temperature to reflux.

Reaction Scheme 35

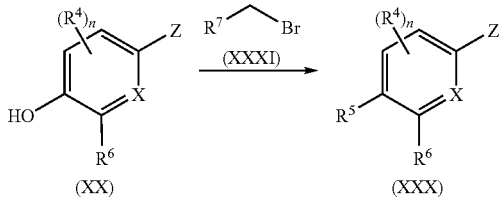

It will be appreciated that compounds of formula (XXX) where $R^6$ is —$CH_2OR^7$, may be prepared by analogous methods starting from the hydroxy compound corresponding to compound of formula (XX).

Compounds of general formula (XX) or (XXXI) are commercially available or may be prepared by procedures known to the skilled person.

The compounds of general formula (IIf), i.e. a compound of formula (II) wherein $R^3$ is not $CH_2OH$, may be generated according to Reaction Scheme 36 by reacting compounds of formula (XXXII) with $NHR^1R^2$ or hexamethyldisilazane for $R^1$=$R^2$=H in the presence of a base (such as diisopropylethyl amine) and a suitable reagent to activate the carboxylic acid function (such as TBTU) in a aprotic solvent (such as DMF) at temperatures ranging from 0° C. to room temperature.

Reaction Scheme 36

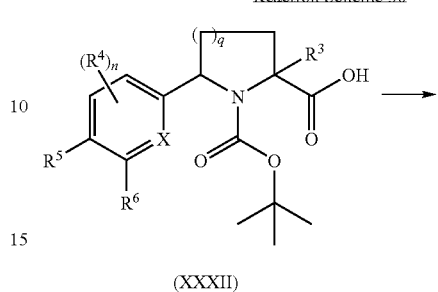

The compounds of general formula (XXXII), with $R^3$ not being $CH_2OH$, may be generated according to Reaction Scheme 37 by reacting compounds of general formula (XXXIV) wherein R is $C_1$-$C_3$ alkyl with a base (such as $LiOH.H_2O$) in a suitable solvent (such as THF) at temperatures ranging from room temperature to reflux, eventually using microwave heating.

Reaction Scheme 37

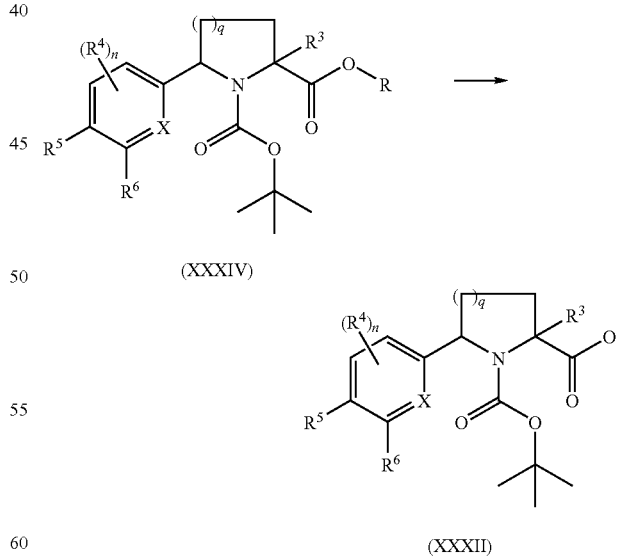

Compounds of formula (XXXIVa), i.e. a compound of formula (II) wherein $R^3$ is $C_1$-$C_3$ alkyl, may be generated according to Reaction Scheme 38 by reacting compounds of formula (XXXV) with a suitable base (such as sodium hydride) followed by treatment with a compound of formula R'—Y (wherein R' is a lower alkyl ($C_1$-$C_3$) and Y is a suitable leaving group, such as I) in an aprotic solvent (such as DMF) at a temperature ranging from 0° C. to room temperature.

Reaction Scheme 38

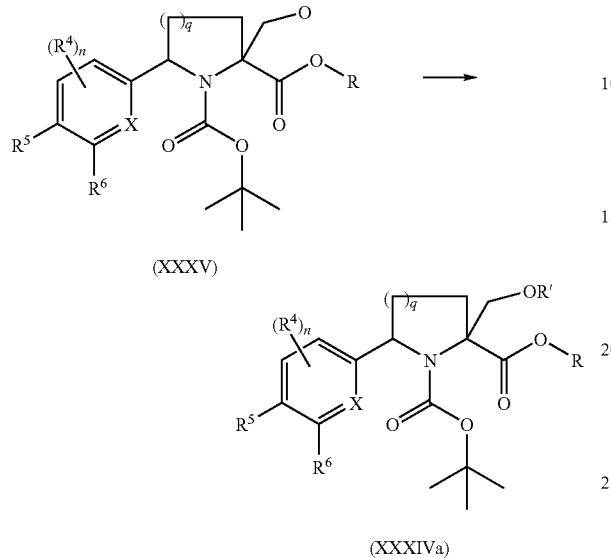

(XXXV)

(XXXIVa)

Compounds of formula (XXXV) may be generated according to Reaction Scheme 39 by reacting compounds (XXV) with a base (such as LiHMDS) in an aprotic solvent (such as THF) at low temperatures (such as −40° C.) followed by treatment with a suitable acylation agent (such as ethylformate). The resulting compound, after a suitable workup is applied, may be immediately dissolved in an alcoholic solvent (such as methanol, ethanol or isopropylalcohol) followed by treatment with a suitable reducing agent (such as $NaBH_4$) at temperatures ranging from 0° C. to room temperature.

Reaction Scheme 39

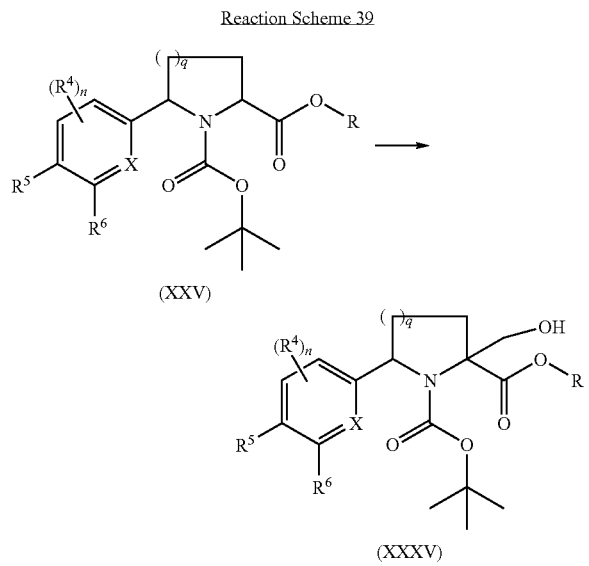

(XXV)

(XXXV)

Compounds of general formula (XXXIV) may be generated according to Reaction Scheme 40 by treating compounds of general formula (XXV) with a suitable base (such as LiHMDS) in an aprotic solvent (such as THF), followed by addition of an alkylating agent such as $R^3$—Y (whereas $R^3$ is not $(CH_2)_qOH$ and Y is a suitable leaving group such as I) at very low temperatures such as −78° C.

Reaction Scheme 40

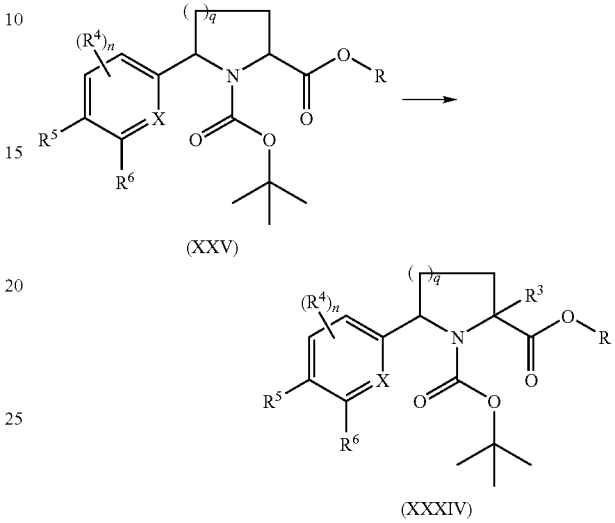

(XXV)

(XXXIV)

Compounds of general formula (If), i.e. a compound of formula (I) wherein $R^3$ is —$CH_2OH$, may be prepared according to Reaction Scheme 41 by treating compounds of general formula (XXXVI), wherein P is a suitable silicon protecting group (such as tert-butyldimethylsilyl), with tetrabutylammonium fluoride in a suitable solvent (such as THF) at room temperature.

Reaction Scheme 41

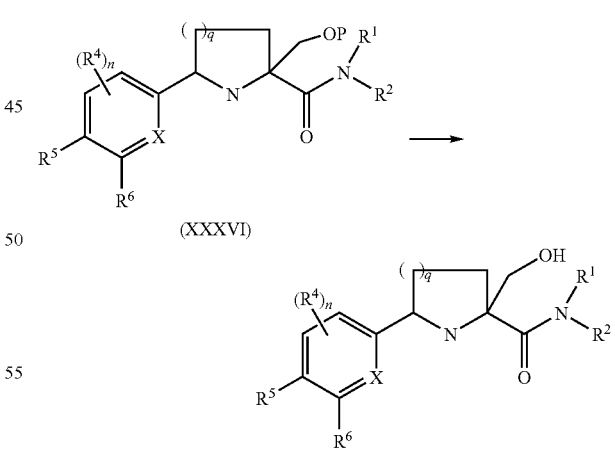

(XXXVI)

(If)

Compounds of general formula (XXXVI) may be generated according to Reaction Scheme 42 by treating compounds of general formula (XXXVII) dissolved in a polar protic solvent (such as methanol) in the presence of a catalyst (such as palladium on charcoal) in a hydrogen atmosphere (1 atm) at room temperature.

Reaction Scheme 42

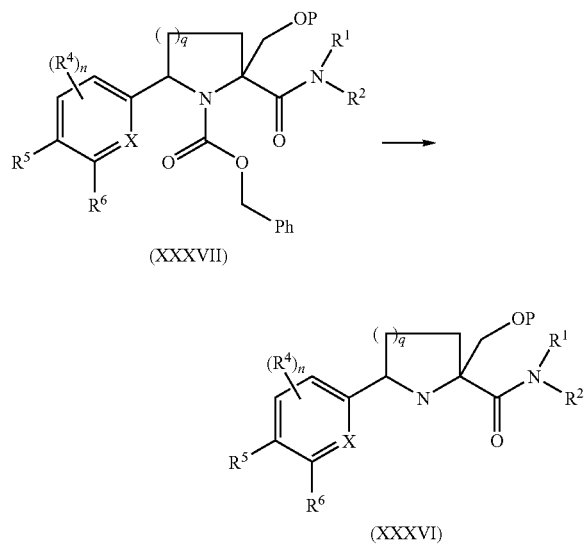

(XXXVII)

(XXXVI)

The compounds of general formula (XXXVII) may be generated according to Reaction Scheme 43 by reacting compounds of formula (XXXVIII) with $NHR^1R^2$ or hexamethyldisilazane when $R^1=R^2=H$ in the presence of a base (such as diisopropylethyl amine) and a suitable reagent to activate the carboxylic acid function (such as TBTU) in an aprotic solvent (such as DMF) at temperatures ranging from 0° C. to room temperature.

Reaction Scheme 43

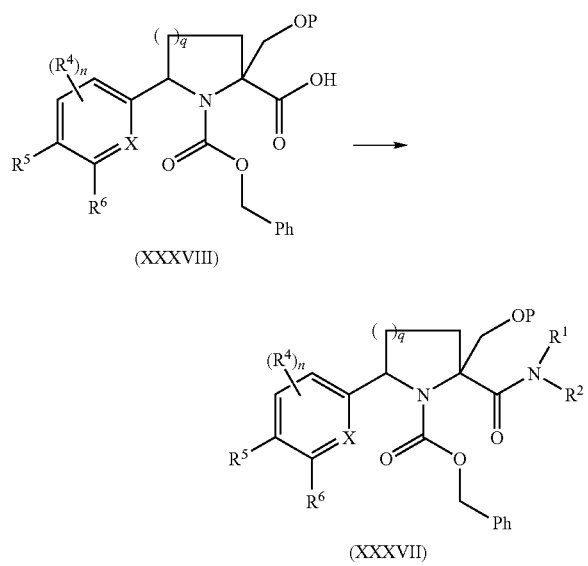

(XXXVIII)

(XXXVII)

The compounds of general formula (XXXVIII) may be generated according to Reaction Scheme 44 by reacting compounds of general formula (XXXIX) with a base (such as $LiOH.H_2O$) in a suitable solvent (such as THF) at temperatures ranging from room temperature to reflux eventually using microwave heating.

Reaction Scheme 44

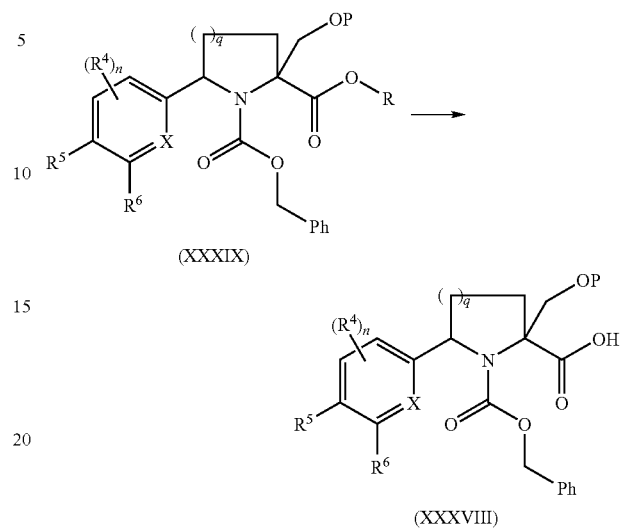

(XXXIX)

(XXXVIII)

Compounds of general formula (XXXIX) may be generated according to Reaction Scheme 45 by reacting compounds of general formula (XL) with a suitable silyl chloride (such as tert-butyldimethyl silyl chloride) in the presence of a suitable base (such as imidazole) in a polar aprotic solvent (such as DMF) at room temperature.

Reaction Scheme 45

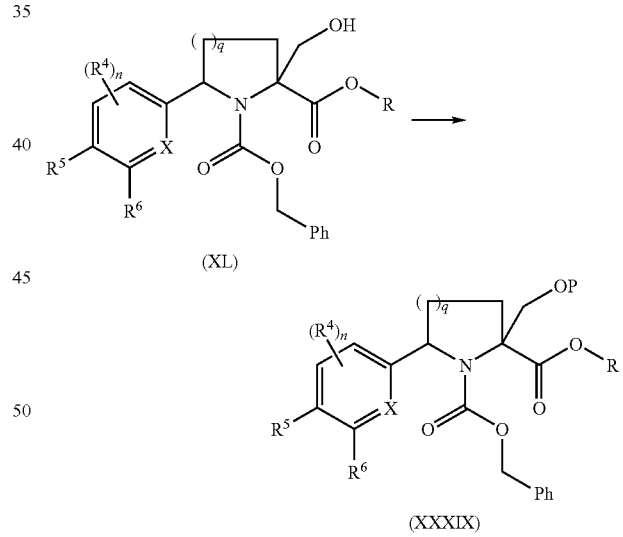

(XL)

(XXXIX)

Compounds of formula (XL) may be generated according to Reaction Scheme 46 by reacting compounds (XLI) with a base (such as LiHMDS) in a aprotic solvent (such as THF) at low temperatures (such as −40° C.) followed by treatment with a suitable acylation agent (such as ethyl formiate). The resulting compound, after a suitable workup is applied, may be immediately dissolved in an alcoholic solvent (such as methanol, ethanol or isopropylalcohol) followed by treatment with a suitable reducing agent (such as $NaBH_4$) at temperatures ranging from 0° C. to room temperature.

Reaction Scheme 46

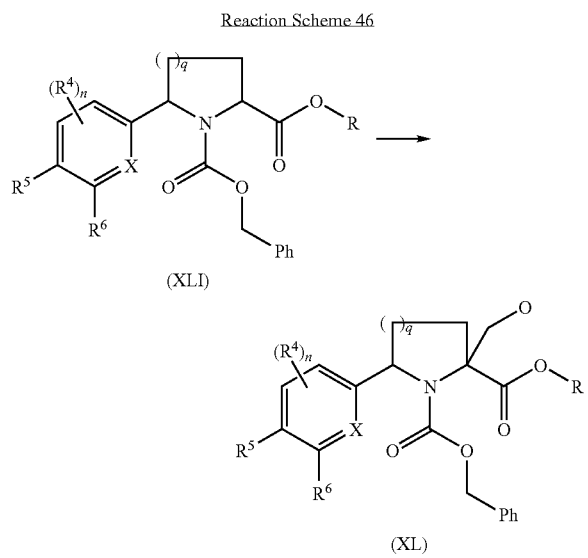

Compounds of general formula (XLI) may be generated according to Reaction Scheme 47 by reacting compounds of general formula (XXVI) with benzyl chloroformate in a chlorinated solvent (such as dichloromethane) in the presence of a suitable base (such as diisopropylethyl amine) at 0° C. to room temperature.

Reaction Scheme 47

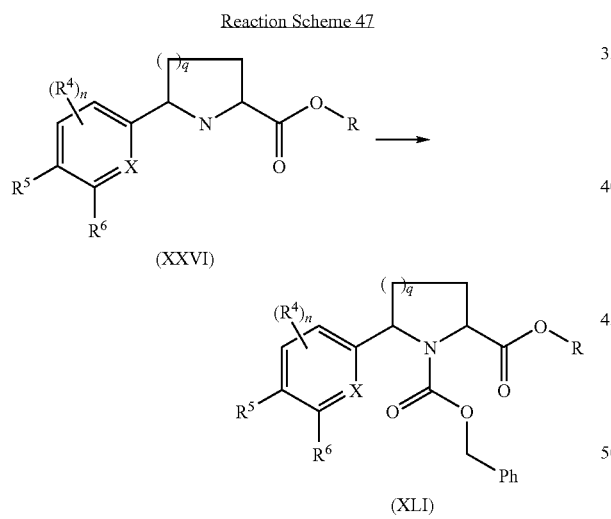

Compounds of general formula (Ig), ie. a compound of formula (I), wherein $R^5$ is —$CH_2OR^7$, and $R^1$ and $R^3$ together with the interconnecting atoms to which they are attached form an unsaturated 7-membered ring, may be generated according to Reaction Scheme 48 by dissolving compounds of general formula (XLII) in a solution of ammonia (for example 7M ammonia) in a suitable solvent. The resulting mixture, after a suitable workup, may be cooled to low temperature, for example 0° C., and a suitable acid (such as trifluoroacetic acid) in a suitable solvent (for example DCM) may be added to remove the protecting group. After a suitable work up of the reaction mixture, cyclization may be achieved through reaction in a suitable solvent (such as methanol) in the presence of a suitable base (such as NaOMe) at refluxing temperature.

Reaction Scheme 48

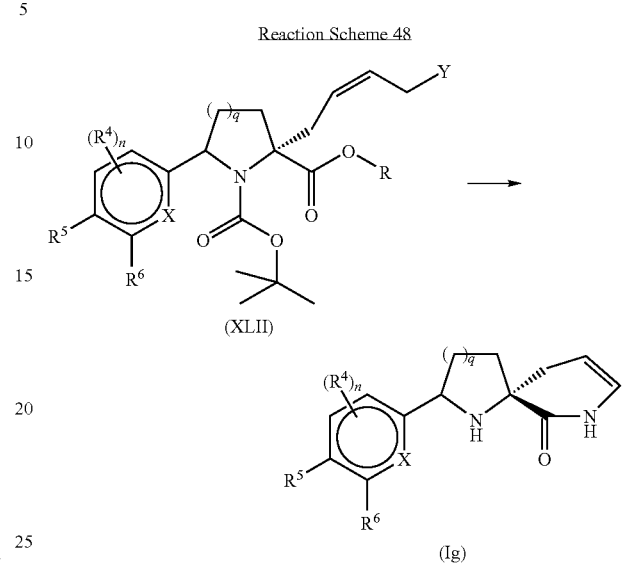

Compounds of general formula (XLII) may be prepared according to Reaction Scheme 49 by reacting a compound of formula (XXV) with the compound $CH_3CH=CHCH_2Y$, wherein Y is a suitable leaving group. Typical reaction conditions involve dissolving the compound $CH_3CH=CHCH_2Y$, in a suitable solvent, such as THF, in the presence of a strong base, such as LiHMDS, in an aprotic solvent (eg THF) at low temperature, for example –30° C.

Reaction Scheme 49

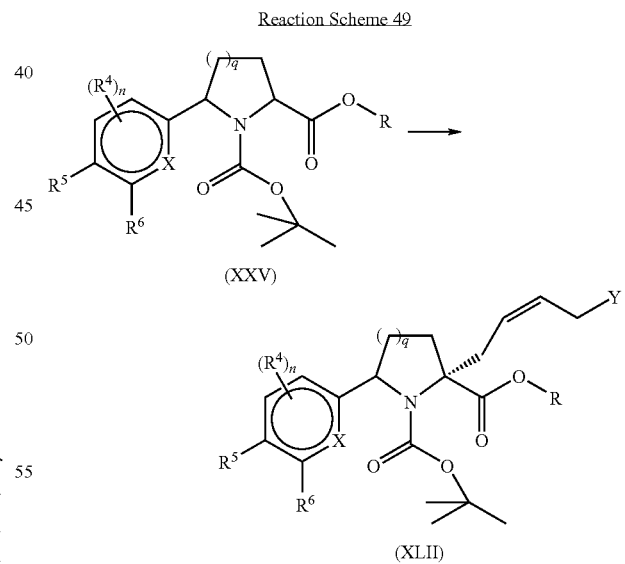

Compounds of general formula (XXV) may be prepared according to the reaction outlined in Reaction Scheme 30.

4-Methylbenzensulfonate salts of compounds of formula (I) may be prepared according to Reaction Scheme 50 by treatment of compounds of formula (I) with p-toluenesulfonic acid monohydrate in the appropriate solvent (such as acetone).

Reaction Scheme 50

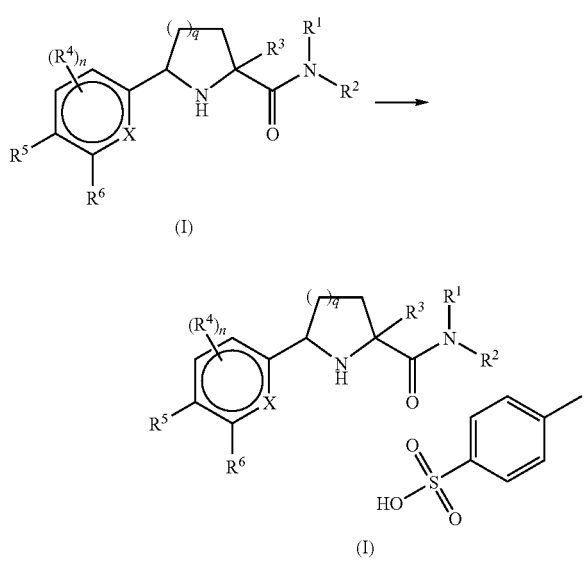

(I)

Alternatively, compounds of general formula (Im), i.e. compounds of formula (I) wherein R¹ and R² are hydrogen, may be prepared according to Reaction Scheme 51 by reacting compounds of formula (XLIII) with a solution of ammonia in a suitable solvent. Typical reaction conditions comprise reaction with ammonia in methanol at a suitable concentration (for example 7N or 11.2 M solution) and at the appropriate temperature (for example room temperature).

Reaction Scheme 51

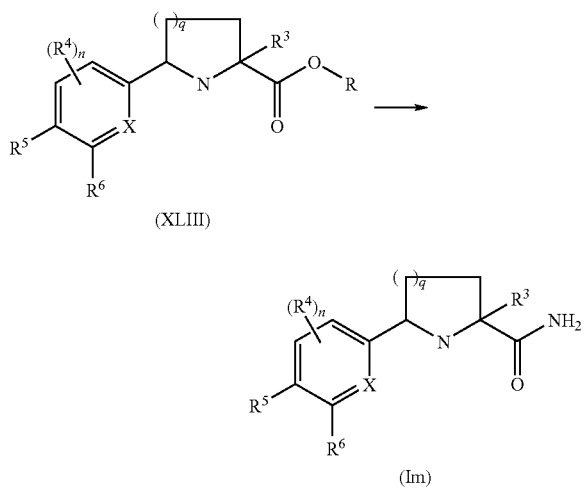

Compounds of general formula (XLIII), wherein R is a $C_{1-3}$ alkyl, may be prepared according to Reaction Scheme 52 by treatment of compounds of formula (XXXIV) under appropriate conditions to remove t-butoxycarbonyl protecting group. Typical reaction conditions are known to the man skilled in the art and may comprise reaction of the compound in a suitable solvent (such as DCM or IPA/MeOH) in the presence of an appropriate acid (such as TFA or HCl).

Reaction Scheme 52

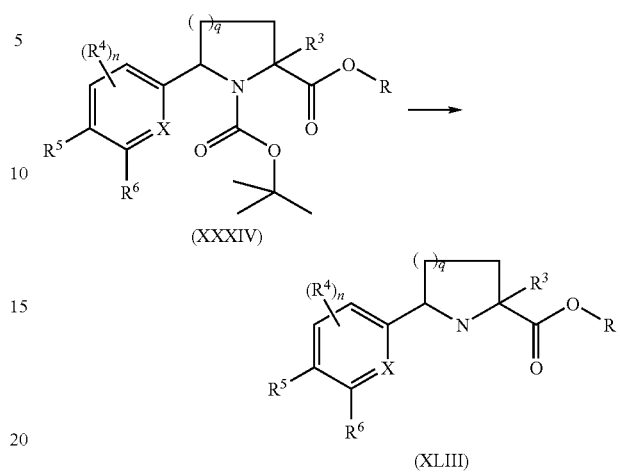

Compounds of general formula (XXXIV) may be prepared according to the reaction outlined in Reaction Scheme 38 or 40.

As discussed hereinabove, it is believed that compounds of the invention may be useful for the treatment of diseases and conditions mediated by modulation of voltage-gated sodium channels.

Therefore, according to a further aspect, the invention provides compounds of the invention for use as a medicament, preferably a human medicament.

According to a further aspect the invention provides the use of compounds of the invention in the manufacture of a medicament for treating or preventing a disease or condition mediated by modulation of voltage-gated sodium channels.

Without wishing to be bound by theory, diseases or conditions that may be mediated by modulation of voltage-gated sodium channels are selected from the list consisting of [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90);

ii) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

iii) Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

iv) Substance-related disorders including Substance Use Disorders such as Substance Dependence, Substance Craving and Substance Abuse; Substance-Induced Disorders such as Substance Intoxication, Substance Withdrawal, Substance-induced Delirium, Substance-Induced Persisting Dementia, Substance-Induced Persisting Amnestic Disorder, Substance-induced Psychotic Disorder, Substance-Induced Mood Disorder, Substance-Induced Anxiety Disorder, Substance-Induced Sexual Dysfunction, Substance-induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-induced Persisting Amnestic Disorder, Alcohol-Induced Psychotic Disorder, Alcohol-induced Mood Disorder, Alcohol-Induced Anxiety Disorder, Alcohol-induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-induced Sexual Dysfunction, Amphetamine-induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic- Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

v) Enhancement of cognition including the treatment of cognition impairment in other diseases such as schizophrenia, bipolar disorder, depression, other psychiatric disorders and psychotic conditions associated with cognitive impairment, e.g. Alzheimer's disease:

vi) Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

vi) Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):

vii) Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

viii) Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

ix) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9): and x) Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

xi) "Impulse control disorder" including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

In another embodiment, diseases or conditions that may be mediated by modulation of voltage gated sodium channels are depression or mood disorders In another embodiment, diseases or conditions that may be mediated by modulation of voltage gated sodium channels are substance related disorders.

In a further embodiment, diseases or conditions that may be mediated by modulation of voltage gated sodium channels are Bipolar Disorders (including Bipolar I Disorder, Bipolar II Disorder (i.e. Recurrent Major Depressive Episodes with Hypomanic Episodes) (296.89), Cyclothymic Disorder (301.13) or Bipolar Disorder Not Otherwise Specified (296.80)).

In a still further embodiment, diseases or conditions that may be mediated by modulation of voltage gated sodium channels are Nicotine-Related Disorders such as Nicotine Dependence (305.1), Nicotine Withdrawal (292.0) or Nicotine-Related Disorder Not Otherwise Specified (292.9).

In an embodiment, compounds of the invention may be useful as analgesics. For example they may be useful in the treatment of chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention may be useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention may also be useful in the amelioration of inflammatory disorders, for example in the treatment of skin conditions (e.g. sunburn, burns, eczema, dermatitis, psoriasis); ophthalmic diseases; lung disorders (e.g. asthma, bronchitis, emphysema, allergic rhinitis, non-allergic rhinitis, cough, respiratory distress syndrome, pigeon fancier's disease, farmer's lung, chronic obstructive pulmonary disease, (COPD); gastrointestinal tract disorders (e.g. Crohn's disease, ulcerative colitis, coeliac disease, regional ileitis, irritable bowel syndrome, inflammatory bowel disease, gastroesophageal reflux disease); other conditions with an inflammatory component such as migraine, multiple sclerosis, myocardial ischemia.

Compounds of the invention may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Compounds of the invention may also be useful in the treatment of bladder hyperrelexia following bladder inflammation.

Compounds of the invention may also be useful in the treatment of neurodegenerative diseases and neurodegeneration such as dementia, particularly degenerative dementia (including senile dementia, Alzheimer's disease, Pick's disease, Huntington's chorea, Parkinson's disease and Creutzfeldt-Jakob disease, motor neuron disease); The compounds may also be useful for the treatment of amyotrophic lateral sclerosis (ALS) and neuroinflamation.

Compounds of the invention may also be useful in neuroprotection and in the treatment of neurodegeneration following stroke, cardiac arrest, pulmonary bypass, traumatic brain injury, spinal cord injury or the like.

Compounds of the invention may also be useful in the treatment of tinnitus, and as local anaesthetics.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may be used in combination with other [antithrombotic drugs such as thrombin inhibitors, thromboxane receptor antagonists, prostacyclin mimetics, phosphodiesterase inhibitors, fibrinogen antagonists, thrombolytic drugs such as tissue plaminogen activator and streptokinase, non-steroidal anti-inflammatory drugs such as aspirin, and the like].

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor, agonist/ opioid kappa receptor antagonist for example buprenorphine; ii) opioid receptor antagonists for example naltrexone; and iii) vasodilatory antihypertensives for example lofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstral agents for example pyridoxine and progesterones.

The compounds of the invention may be used in combination with the following agents totreat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstral agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, pheneizine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

It will be appreciated that references herein to "treatment" extend to prophylaxis, prevention of recurrence and suppression or amelioration of symptoms (whether mild, moderate or severe) as well as the treatment of established conditions.

The compound of the invention may be administered as the raw chemical but the active ingredient is preferably presented as a pharmaceutical formulation.

According to a further aspect, the invention provides a pharmaceutical composition comprising a compound of the invention, in association with one or more pharmaceutically acceptable carrier(s), diluents(s) and/or excipient(s). The carrier, diluent and/or excipient must be "acceptable" in the sense of being compatible with the other ingredients of the composition and not deleterious to the recipient thereof.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter-sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit will for example contain from 5-1000 mg of the active ingredient. The dosage as employed for adult human treatment may range from 10 to 3000 mg per day depending on the route and frequency of administration. For oral administration a typical dose may be in the range of 50 to 1500 mg per day, for example 120 to 1000 mg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The embodiments described for the first aspect similarly apply to these further aspects. The diseases and conditions described above extend, where appropriate, to these further aspects:

i) A compound of the invention for use in treating or preventing a disease or condition mediated by modulation of voltage-gated sodium channels.
ii) A method of treatment or prevention of a disease or condition mediated by modulation of voltage-gated sodium channels in a mammal comprising administering an effective amount of a compound of the invention.
iii) Use of a compound of the invention in the manufacture of a medicament to treat or prevent a disease or condition mediated by modulation of voltage-gated sodium channels.
iv) Use of a compound of the invention to treat or prevent a disease or condition mediated by modulation of voltage-gated sodium channels.

EXAMPLES

The invention is illustrated by the Examples described below.

In the procedures that follow, after each starting material, reference to a Description or Example by number is typically provided. This is provided merely for assistance to the skilled chemist. The starting material may not necessarily have been prepared from the batch referred to.

The compounds described in the Examples described hereinafter have all been prepared as a first step from stereochemically pure methyl 5-oxo-L-prolinate or ethyl 5-oxo-D-prolinate, for example 99% ee. The stereochemistry of the compounds of the Descriptions and Examples have been assigned on the assumption that the pure configuration of 5-oxo-prolinate is maintained throughout any subsequent reaction conditions.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

The absolute configuration of the stereocenter at the 2-position as shown below the has been assigned on the basis of NOE $^1$H NMR experiments, by determining the relative stereochemistry of this stereocenter with respect to the one at the 5-position.

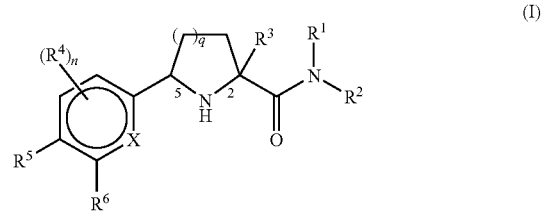

(I)

Compounds are named using ACD/Name PRO6.02 chemical naming software (Advanced Chemistry Development Inc., Toronto, Ontario, M5H2L3, Canada).

Proton Magnetic Resonance (NMR) spectra are typically recorded either on Varian instruments at 300, 400 or 500 MHz, or on a Bruker instrument at 300 and 400 MHz. Chemical shifts are reported in ppm (δ) using the residual solvent line as internal standard. Splitting patterns are designed as s, singlet; d, doublet; t, triplet; q, quartet; m, multiplet; b, broad. The NMR spectra were recorded at a temperature ranging from 25 to 90° C. When more than one conformer was detected the chemical shifts for the most abundant one is reported.

HPLC analysis indicated by $R_t$(HPLC): x min, was performed on an Agilent 1100 series instrument using a Luna 3 u C18(2) 100 A (50×2.0 mm) column (mobile phase: 100% [water+0.05% TFA] to 95% [acetonitrile+0.05% TFA] in 8 min, flux=1 ml/min, detection wavelength 220 nm.

Mass spectra (MS) are typically taken on a 4 II triple quadrupole Mass Spectrometer (Micromass UK) or on a Agilent MSD 1100 Mass Spectrometer, operating in ES (+) and ES (−) ionization mode or on an Agilent LC/MSD 1100 Mass Spectrometer, operating in ES (+) and ES (−) ionization mode coupled with HPLC instrument Agilent 1100 Series LC/MS—ES (+):analysis performed on a Supelcosil ABZ+ Plus (33×4.6 mm, 3 µm) (mobile phase: 100% [water+0.1% $HCO_2H$] for 1 min, then from 100% [water+0.1% $HCO_2H$] to 5% [water+0.1% $HCO_2H$] and 95% [$CH_3CN$] in 5 min, finally under these conditions for 2 min; T=40° C.; flux=1 mL/min; LC/MS—ES (−):analysis performed on a Supelcosil ABZ+Plus (33×4.6 mm, 3 µm) (mobile phase: 100% [water+0.05% $NH_3$] for 1 min, then from 100% [water+0.05% $NH_3$ to 5% [water+0.05% $NH_3$] and 95% [$CH_3CN$] in 5 min, finally under these conditions for 2 min; T=40° C.; flux=1 mL/min]. In the mass spectra only one peak in the molecular ion cluster is reported.

Total ion current (TIC) and DAD UV chromatographic traces together with MS and UV spectra associated with the peaks are typically taken also on a HPLC/MS Acquity™ system equipped with 2996 PDA detector and coupled to a Waters Micromass ZQ™ mass spectrometer operating in positive or negative electrospray ionisation mode. [LC/MS—ES (+/−): analyses performed using an Acquity™ HPLC BEH C18 column (50×21 mm, 1.7 μm particle size), column temperature 40° C. (mobile phase: A-water+0.1% HCOOH/B—MeCN+0.075% HCOOH, Flow rate: 1.0 mL/min, Gradient: t=0 min 3% B, t=0.05 min 6% B, t=0.57 min 70% B, t=1.4 min 99% B, t=1.45 min 3% B)]. The usage of this methodology is indicated by "UPLC" in the analytic characterization of the described compounds.

For reactions involving microwave irradiation, a Personal Chemistry Emrys™ Optimizer was used.

Flash silica gel chromatography was carried out on silica gel 230-400 mesh (supplied by Merck AG Darmstadt, Germany) or over Varian Mega Be-Si pre-packed cartridges or over pre-packed Biotage silica cartridges.

SPE-SCX cartridges are ion exchange solid phase extraction columns supplied by Varian. The eluent used with SPE-SCX cartridges is methanol followed by 2N ammonia solution in methanol.

In a number of preparations, purification was performed using either Biotage manual flash chromatography (Flash+) or automatic flash chromatography (Horizon) systems. All these instruments work with Biotage Silica cartridges.

SPE-Si cartridges are silica solid phase extraction columns supplied by Varian.

CUNO filters are carbon filters of type CUNO PLAQ. R55SP B0501 ref. code 2730943.

It will be recognised that spectra and diffraction data will vary slightly according to various factors such as the temperature, concentration and instrumentation used. The skilled person will recognise that XRPD peak positions are affected by differences in sample height. The peak positions quoted herein are thus subject to a variation of +/−0.15 degrees 2-theta.

X-Ray Powder Diffraction

X Ray Powder Diffraction (XRPD) analysis was performed on Bruker D5005, using Sol-X detector. The acquisition conditions were: radiation: Cu Kα, generator tension: 40 kV, generator current: 50 mA, start angle: 2.0°2θ, end angle: 45.0°2θ, step size: 0.02°2θ, time per step: 1 seconds. The sample was prepared on zero background sample holder.

Differential Scanning Calorimetry (DSC): It should be recognized that the endotherm peak as measured is dependent under a number of factors including the machine employed, the rate of heating, the calibration standard, humidity and the purity of the sample used.

Melting points reported in the experimentals are estimated on the basis of the onset of endotherm peaks registered during DSC analysis.

The following table lists the used abbreviations:
AcCl—acetyl chloride
DCM—dichloromethane
DMAP—dimethylaminopyridine
DMF—dimethylformamide
HMDS—1,1,1,3,3,3-hexamethyldisilazane
LiHMDS—lithium bis(trimethylsilyl)amide
TBTU—O-(benzotriazol-1-yl)-N,N,N'N'-tetramethyluronium tetrafluoroborate
TEA—triethylamine
THF—tetrahydrofuran
MTBE—Methyl-t-butyl-ether
EtOAc—Ethyl Acetate
NMO—N-methyl-morpholine-N-oxide
Et$_2$O—Diethyl ether
IPA—Isopropyl alcohol
DIPEA—Diisopropylethyl amine Description 1: 1-(1,1-Dimethylethyl) 2-methyl (2S)-5-oxo-1,2-pyrrolidine-dicarboxylate (D1)

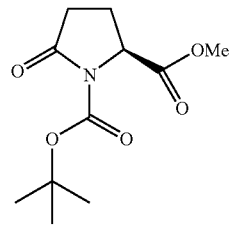

To a solution of commercially available methyl 5-oxo-L-prolinate (Sigma Aldrich Ltd.) (20 g, 140 mmol) in DCM (200 ml) were added TEA (19.6 ml, 140 mmol), 4-DMAP (17.2 g, 140 mmol) and finally dropwise a solution of di-tert-butyl dicarbonate (61 g, 280 mmol) in DCM (100 ml). The resulting red mixture was stirred at room temperature for 2 hours. After the reaction was finished, as shown by TLC, the solvent was removed in vacuo and the crude material was purified by chromatography on silica gel eluting with cyclohexane/ethyl acetate (7:3 to 4:6) to afford (after a trituration in hexane/diethylether 1:1) the title compound as a white solid (32.4 g, 96%); R$_f$(cyclohexanes:ethyl acetate=65:35): 0.21; $^1$H NMR (300 MHz, CDCl$_3$) δ(ppm): 4.62 (dd, 1H), 3.78 (s, 3H), 2.68-2.58 (m, 1H), 2.52-2.45 (m, 1H), 2.37-2.27 (m, 1H), 2.08-1.97 (m, 1H), 1.48 (s, 9H).

Description 2: Methyl (2S)-2-({[(1,1-dimethylethyl)oxy]carbonyl}amino)-5-oxo-5-{4-[(phenylmethyl)oxy]phenyl}pentanoate (D2)

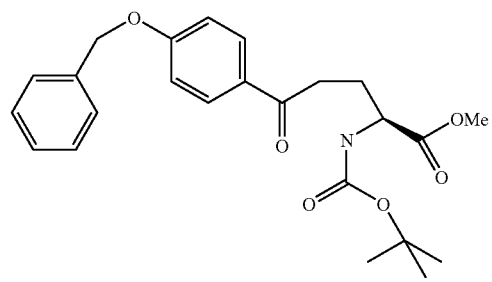

To a solution of commercially available (Sigma Aldrich Ltd.) 1-bromo-4-[(phenylmethyl)oxy]benzene (390 mg, 1.48 mmol) in dry THF (2 ml) at −78° C., under nitrogen atmosphere, was added dropwise n-butyllithium 1.6M solution in hexanes (0.88 ml, 1.4 mmol). The resulting suspension was stirred at −78° C. for 40 minutes and then it was added dropwise to a solution of 1-(1,1-dimethylethyl) 2-methyl (2S)-5-oxo-1,2-pyrrolidinedicarboxylate (D1, 300 mg, 1.23 mmol) in dry THF (2.4 ml) previously cooled to −78° C. The mixture was stirred at −78° C. for 40 minutes and at −40° C. for 1 h, then it was quenched at −40° C. with a saturated aqueous ammonium chloride solution. The mixture was diluted with water and extracted with ethyl acetate. The organic phase was then washed with brine, dried (Na$_2$SO$_4$), and evaporated under vacuo to give the crude material, which was then purified by chromatography on silica gel eluting with cyclohexane:ethyl acetate (95:5), thus affording the title compound as a white solid (170 mg, 32%); R$_f$(cyclohexane:

ethyl acetate 8:2): 0.30; $^1$H NMR (300 MHz, CDCl$_3$) δ(ppm): 7.95 (d, 2H), 7.50-7.33 (m, 5H), 7.03 (d, 2H), 5.20 (bs, 1H), 5.15 (s, 2H), 4.45-4.35 (m, 1H), 3.78 (s, 3H), 3.15-2.95 (m, 2H), 2.36-2.26 (m, 1H), 2.16-2.02 (m, 1H), 1.45 (s, 9H).

Description 3: Methyl (2S)-5-{4-[(phenylmethyl)oxy]phenyl}-3,4-dihydro-2H-pyrrole-2-carboxylate (D3)

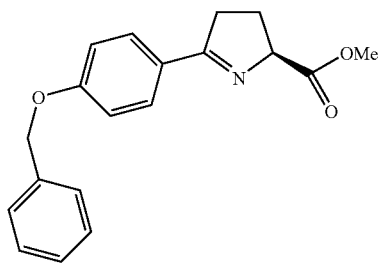

To a solution of methyl (2S)-2-({[(1,1-dimethylethyl)oxy]carbonyl}amino)-5-oxo-5-{4-[(phenylmethyl)oxy]phenyl}pentanoate (D2, 323 mg, 0.75 mmol) in dry DCM (4 ml) at 0° C., under nitrogen atmosphere, was added trifluoroacetic acid (1 ml) dropwise. The resulting pale pink solution was allowed to warm to room temperature over 1 hour, then it was evaporated under vacuum, affording the title compound (D3, 291 mg, 0.68 mmol, 91%) as a greenish oil which may be used in the next step without further purification; MS: (ES/+) m/z: 310 [MH]); C19H19NO3 requires 309; R$_t$ (HPLC): 3.69 min.

Description 4: Methyl (5R)-5-{4-[(phenylmethyl)oxy]phenyl}-L-prolinate (D4)

Description 5: Methyl (5S)-5-{4-[(phenylmethyl)oxy]phenyl}-L-prolinate (D5)

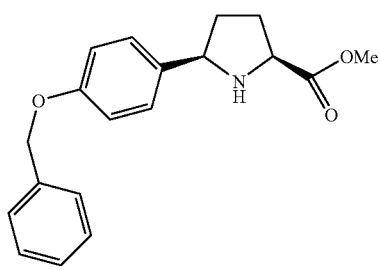

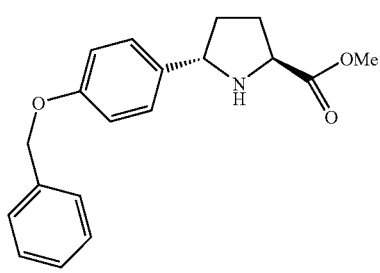

To a solution of methyl (2S)-5-{4-[(phenylmethyl)oxy]phenyl}-3,4-dihydro-2H-pyrrole-2-carboxylate (D3, 13.7 g, 32.4 mmol) in methanol (200 ml, 6 ml/mmol of substrate) was added PtO$_2$ (240 mg, 7.4 mg/mmol of substrate) and the mixture was stirred under hydrogen (2 atmospheres) for 6 hours. Then the catalyst was filtered off and the solvent removed under reduced pressure to give a red oil which was dissolved in ethyl acetate and washed with aqueous NaHCO$_3$. The resulting crude material was purified by chromatography on silica gel eluting with cyclohexane/ethyl acetate (9:1 to 8:2) to afford the title compounds. D4 4.15 g, 13.3 mmol, yield 41%; R$_t$ (HPLC): 3.80 min; R$_f$ (cyclohexane:ethyl acetate=7:3): 0.18; MS: (ES/+) m/z: 312 [MH$^+$]; C19H21NO3 requires 311; $^1$H NMR (500 MHz, CDCl$_3$) δ(ppm): 7.40 (d, 2H); 7.35 (t, 2H); 7.33 (d, 2H); 7.29 (t, 1H); 6.93 (d, 2H); 5.03 (s, 2H); 4.23 (dd, 1H); 4.00 (dd, 1H); 3.71-3.79 (m, 3H); 2.18-2.30 (m, 1H); 2.09-2.18 (m, 2H); 1.67-1.78 (m, 1H); NOE between the proton at C2 and the proton at C5 could be observed. D5, 0.6 g, 1.9 mmol, yield 6%; R$_t$ (HPLC): 3.73 min; R$_f$ (cyclohexane:ethyl acetate=7:3): 0.32; MS: (ES/+) m/z: 312 [MH$^+$]; C19H21NO3 requires 311; $^1$H NMR (500 MHz, CDCl$_3$) δ(ppm): 7.40 (d, 2H); 7.35 (t, 2H); 7.29 (d, 2H); 7.28 (t, 1H); 6.91 (d, 2H); 4.97-5.07 (m, 2H); 4.29 (dd, 1H); 4.09 (dd, 1H); 3.71-3.75 (m, 3H); 2.29-2.42 (m, 1H); 2.09-2.20 (m, 1H); 1.90-2.02 (m, 1H); 1.69-1.82 (m, 1H); NOE between the proton at C2 and the proton at C5 was not observed.

Description 6: 1-(1,1-Dimethylethyl) 2-methyl (2S, 5R)-5-{4-[(phenylmethyl)oxy]phenyl}-1,2-pyrrolidinedicarboxylate (D6)

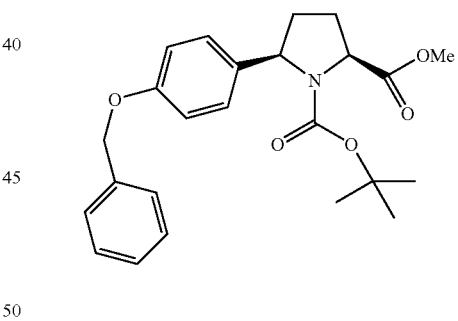

To a solution of methyl (5R)-5-{4-[(phenylmethyl)oxy]phenyl}-L-prolinate (D4, 2.6 g, 8.35 mmol) in DCM (30 ml) was added di-tert-butyl dicarbonate (2.0 g, 9.18 mmol). After stirring for 1 h at room temperature, the mixture was evaporated and the residue was purified by chromatography on silica gel using cyclohexane/ethyl acetate (9:1 to 85:15) to afford the title compound (3.29 g, 96%) as a white foam; R$_t$ (HPLC): 6.55 min; MS: (ES/+) m/z: 434 [M+Na$^+$], 312 [M-BOC]; C$_{24}$H$_{29}$NO$_5$ requires 411; $^1$H NMR (400 MHz, CDCl$_3$) δ (ppm): 7.52-7.43 (m, 4H); 7.43-7.37 (m, 2H); 7.37-7.30 (m, 1H); 6.96 (d, 2H); 5.09 and 5.06 (s, s, 2H); 4.99-4.93 and 4.52-4.44 (m, 1H); 4.76-4.68 and 4.39-4.32 (m, m, 1H); 3.82 (s, 3H); 2.36-2.26 (m, 1H); 2.26-2.15 (m, 1H); 2.12-2.01 (m, 1H); 2.01-1.88 (m, 1H); 1.42 and 1.17 (s, s, 9H).

Description 7: 1,1-Dimethylethyl(2S,5R)-2-methoxylcarbonyl-2-methyl-5-{4-[(phenylmethyl)oxy]phenyl}-1-pyrrolidinecarboxylate (D7)

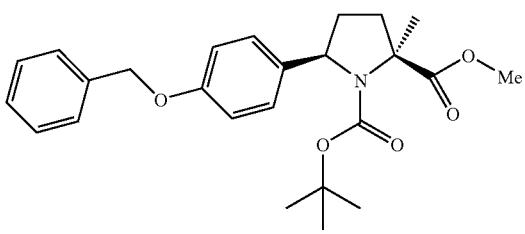

To a solution of 1-(1,1-dimethylethyl) 2-methyl (2S,5R)-5-{4-[(phenylmethyl)oxy]phenyl}-1,2-pyrrolidinedicarboxylate (D6, 1.52 g, 3.7 mmol) in dry THF (27 ml) at −78° C. was added LiHMDS (4.0 ml, 4.0 mmol, 1M solution in THF). The mixture was allowed to warm to −20° C. and was stirred for 40 min at that temperature. Then the mixture was again cooled to −78° C. and methyl iodide (3.15 g, 22.1 mmol) was added. The mixture was left stirring for another 30 min at the same temperature. After standard work up, the organic layer was evaporated. The crude material was purified by chromatography on silica gel using cyclohexanes and ethyl acetate (1:0 to 9:1) affording the title compound (1.23 g, 78%); $R_t$ (HPLC): 6.76 min; MS: (ES/+) m/z: 448 [M+Na+]; C25H31NO5 requires 425; $^1$H NMR (400 MHz, CDCl$_3$) δ(ppm): 7.45-7.38 (m, 4H); 7.35 (t, 2H); 7.29 (t, 1H); 6.90 (d, 2H); 5.04 and 5.01 (s, s, 2H); 4.98 and 4.79 (d, d, 1H); 3.79 (s, 3H); 2.50-2.35 (m, 1H); 2.34-2.22 (m, 1H); 1.87-1.73 (m, 2H); 1.58 and 1.55 (s, s, 3H); 1.37 and 1.09 (s, s, 9H). NOE between the methyl group and the proton at C5 could be observed.

Description 8: (5R)-1-{[(1,1-Dimethylethyl)oxy]carbonyl}-2-methyl-5-{4-[(phenylmethyl)oxy]phenyl}-L-proline (D8)

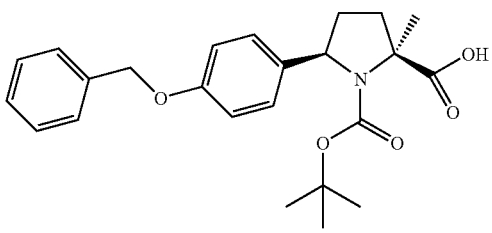

A solution of 1,1-dimethylethyl (2S,5R)-2-(aminocarbonyl)-2-methyl-5-{4-[(phenylmethyl)oxy]phenyl}-1-pyrrolidinecarboxylate (D7, 0.977 g, 2.29 mmol) and LiOH.H$_2$O (192 mg, 4.59 mmol, dissolved in 7 ml H$_2$O) in methanol (7 ml) was heated in a microwave synthesizer for 1 hour at 100° C. After evaporation of methanol, the aqueous phase was acidified to pH 3 with 1M HCl and extracted with ethyl acetate. The organic layer was dried (Na$_2$SO$_4$), filtered and evaporated affording the title compound (white solid, 880 mg, 93%); $R_f$ (cyclohexane:ethyl acetate=6:4): 0.24; $R_t$ (HPLC): 6.07 min. MS: (ES/−) m/z: 410 [M−H]; C24H29NO5 requires 411; $^1$H NMR (500 MHz, DMSO-d$_6$) δ(ppm): 12.92-12.23 (br. s, 1H); 7.48-7.40 (m, 4H); 7.40-7.33 (m, 2H); 7.31 (t, 1H); 6.92 (t, 2H); 5.08 and 5.06 (s, s, 2H); 4.85 and 4.76 (d, d, 1H); 2.48-2.34 (m, 1H); 2.19-2.05 (m, 1H); 1.81-1.72 (m, 1H); 1.64-1.57 (m, 1H); 1.46 and 1.43 (s, s, 3H); 1.32 and 1.03 (s, s, 9H).

Description 9: 1,1-Dimethylethyl (2S,5R)-2-(aminocarbonyl)-2-methyl-5-{4-[(phenylmethyl)oxy]phenyl}-1-pyrrolidinecarboxylate (D9)

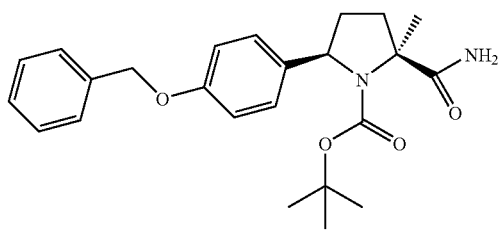

A solution of (5R)-1-{[(1,1-dimethylethyl)oxy]carbonyl}-2-methyl-5-{4-[(phenylmethyl)oxy]phenyl}-L-proline (D8, 870 mg, 2.11 mmol), diisopropylethyl amine (0.74 ml, 4.22 mmol) and TBTU (814 mg, 2.53 mmol) in dry DMF (8 ml) was stirred for 15 min at room temperature. HMDS (0.70 ml, 3.17 mmol) was added and stirring was continued at room temperature overnight. The mixture was cooled to 0° C. and saturated aqueous NaHCO$_3$ solution was added. The mixture was extracted with ethyl acetate and washed three times with ice cold brine. The organic layer was dried (Na$_2$SO$_4$), filtered and evaporated. The residue was purified by chromatography on silica gel using cyclohexane and ethyl acetate (7:3) to afford the title compound (857 mg, 99%); $R_t$ (HPLC): 5.85 min; MS: (ES/+) m/z: 433 [M+Na$^+$]; C24H30N2O4 requires 410; $R_f$ (cyclohexane:ethyl acetate=6:4): 0.32.

Description 10: 1,1-Dimethylethyl (2S,5R)-2-(aminocarbonyl)-5-(4-hydroxyphenyl)-2-methyl-1-pyrrolidinecarboxylate (D10)

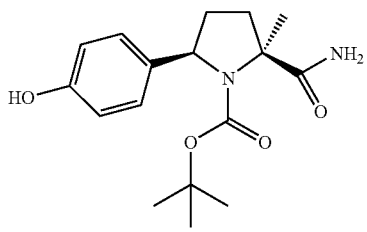

To a solution of 1,1-dimethylethyl (2S,5R)-2-(aminocarbonyl)-2-methyl-5-{4-[(phenylmethyl)oxy]phenyl}-1-pyrrolidinecarboxylate (D9, 850 mg, 2.07 mmol) in methanol (10 ml) was added Pd/C 10% wt (85 mg, 10 wt %) and the mixture was stirred under hydrogen (1 atmosphere) for 5 hours. The catalyst was filtered off and the solvent removed under reduced pressure to give the title compound as a white solid (D10, 623 mg, 94%); $R_t$ (HPLC): 4.00 min; $^1$H NMR (500 MHz, DMSO-d$_6$) δ (ppm): 9.16 (s, 1H), 7.28-7.42 (m, 1H), 7.16-7.26 (m, 2H), 7.02-7.14 (m, 1H), 6.59-6.68 (m, 2H), 4.56-4.85 (m, 1H), 2.07-2.41 (m, 2H), 1.52-1.77 (m, 2H), 1.51 (s, 3H), 1.31 and 1.05 (s, s, 9H).

Description 11: 1,1-Dimethylethyl (2S,5R)-2-(aminocarbonyl)-5-(4-{[(2-fluorophenyl)methyl]oxy}phenyl)-2-methyl-1-pyrrolidinecarboxylate (D11)

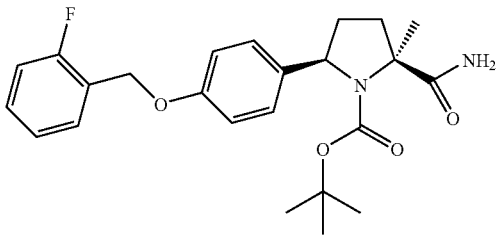

To a solution of 1,1-dimethylethyl (2S,5R)-2-(aminocarbonyl)-5-(4-hydroxyphenyl)-2-methyl-1-pyrrolidinecarboxylate (D10, 300 mg, 0.936 mmol) and potassium carbonate (194 mg, 1.4 mmol) in acetonitrile (4 ml) was added 1-(bromomethyl)-2-fluorobenzene (Sigma Aldrich Ltd.) (170 µl, 1.4 mmol) and the mixture was stirred overnight at room temperature. After the reaction was finished, as shown by TLC, ethyl acetate and water were added. The organic phase was then washed with brine, dried, filtered and evaporated. The crude material was purified by chromatography on silica gel using cyclohexane/ethyl acetate (8:2 to 7:3) to afford the title compound (306 mg, 72%); R (HPLC): 5.88 min; $R_f$(cyclohexane:ethyl acetate=1:1): 0.51; $^1$H NMR (300 MHz, DMSO-d6) δ(ppm): 7.60-7.49 (t, 2H); 7.46-7.32 (m, 2H); 7.29-7.15 (m, 3H); 7.13-7.02 (m, 1H); 6.98-6.88 (m, 2H); 5.11 (s, 2H); 4.87-4.62 (m, 1H); 2.41-2.16 (m, 2H); 1.78-1.64 (m, 1H); 1.64-1.56 (m, 1H); 1.52 (s, 3H); 1.32 and 1.03 (s, s, 9H).

Description 12: 1,1-Dimethylethyl (2S,5R)-2-(aminocarbonyl)-5-(4-{[(2-cyanophenyl)methyl]oxy}phenyl)-2-methyl-1-pyrrolidinecarboxylate (D12)

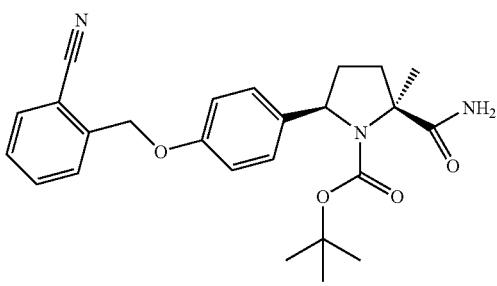

The title compound was prepared using a similar procedure as set out earlier in Description 11 replacing 1-(bromomethyl)-2-fluorobenzene with 1-(bromomethyl)-2-cyanobenzene; $R_t$ (HPLC): 5.50 min; $R_f$(cyclohexane:ethyl acetate=7:3): 0.07; MS: (ES/+) m/z: 458 [M+Na$^+$]; C25H29N3O4 requires 435.

Description 13: 1,1-Dimethylethyl (2S,5R)-2-(aminocarbonyl)-5-{4-[(2-cyanophenyl)oxy]phenyl}-2-methyl-1-pyrrolidinecarboxylae (D13)

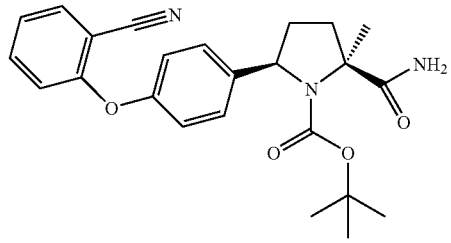

A solution of 1,1-dimethylethyl (2S,5R)-2-(aminocarbonyl)-5-(4-hydroxyphenyl)-2-methyl-1-pyrrolidinecarboxylate (D10, 60 mg, 0.187 mmol), 2-fluorobenzonitrile (45 mg, 0.374 mmol) and potassium carbonate (39 mg, 0.280 mmol) in DMF (2 ml) was heated under microwave irradiation for 30 min to 120° C. Water and ethyl acetate were added to the mixture, and the organic layer was washed with ice cold water. The solution was dried (Na$_2$SO$_4$) and evaporated. The crude material was purified by chromatography on silica gel using cyclohexane/ethyl acetate (7:3 to 6:4) to afford the title compound (78 mg); $R_t$ (HPLC): 5.44 min; $R_f$(cyclohexane: ethyl acetate=1:1): 0.21; MS: (ES/+) m/z: 444 [M+Na$^+$]; C24H27N3O4 requires 421.

Description 14: 1-(1,1-Dimethylethyl) 2-ethyl (2R)-5-oxo-1,2-pyrrolidinedicarboxylate (D14)

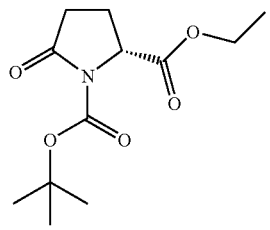

The title compound was prepared using a similar procedure as set out earlier in Description 1 starting from commercially available ethyl 5-oxo-D-prolinate (12 g, 75.6 mmol); $R_t$ (HPLC) 3.94 min; $^1$H NMR (400 MHz, CDCl$_3$) δ (ppm): 4.61 (dd, 1H); 4.25 (q, 2H); 2.58-2.69 (m, 1H); 2.44-2.55 (m, 1H); 2.26-2.38 (m, 1H); 2.00-2.08 (m, 1H); 1.50 (s, 9H); 1.31 (t, 3H).

Description 15: Ethyl (2R)-2-({[(1,1-dimethylethyl)oxy]carbonyl}amino)-5-oxo-5-{4-[(phenylmethyl)oxy]phenyl}pentanoate (D15)

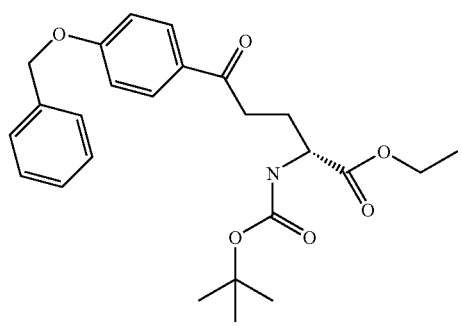

The title compound was prepared (2.9 g, 16%) using a similar procedure as set out earlier in Description 2 starting from 1-(1,1-dimethylethyl) 2-ethyl (2R)-5-oxo-1,2-pyrrolidinedicarboxylate (D14, 10.5 g 40.8 mmol) and 4-iodophenyl phenylmethyl ether (13.34 g, 43 mmol); $R_t$ (HPLC): 6.37 min; MS: (ES/+) 464 m/z: [M+Na$^+$]; C25H31NO6 requires 441; $^1$H NMR (400 MHz, CDCl$_3$) δ (ppm): 7.92 (d, 2H); 7.29-7.45 (m, 5H); 6.99 (d, 2H); 5.18 (bs, 1H); 5.12 (s, 2H); 4.29-4.4 (bm, 1H); 4.20 (q, 2H); 2.94-3.16 (m, 2H); 2.22-2.33 (m, 1H); 2.00-2.15 (m, 1H); 1.39 (s, 9H); 1.28 (t, 3H).

Description 16: Ethyl (2R)-5-{4-[(phenylmethyl)oxy]phenyl}-3,4-dihydro-2H-pyrrole-2-carboxylate (D16)

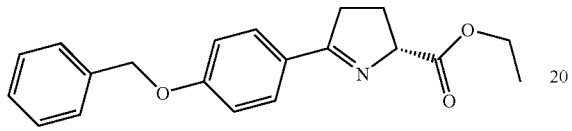

The title compound was prepared using a similar procedure as set out earlier in Description 3 starting from ethyl (2R)-2-({[(1,1-dimethylethyl)oxy]carbonyl}amino)-5-oxo-5-{4-[(phenylmethyl)oxy]phenyl}pentanoate (D15, 2.9 g, 6.57 mmol). The crude material may be used unpurified in the next step; $R_t$ (HPLC): 3.80 min; MS: (ES/+) 324 m/z: [MH$^+$]; C20H21NO3 requires 323.

Description 17: Ethyl (5S)-5-{4-[(phenylmethyl)oxy]phenyl}-D-prolinate (D17

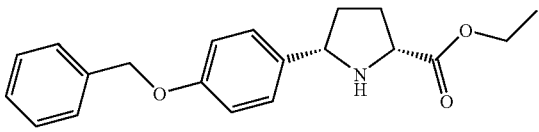

The title compound was prepared (1.84 g, 86% over two steps) using a similar procedure as set out earlier in Description 4 using the crude material obtained from Description 16; $R_t$ (HPLC): 4.03 min; MS: (ES/+) m/z: 326 [MH$^+$]; C20H23NO3 requires 325; $^1$H NMR (500 MHz, CDCl$_3$) δ(ppm): 7.30-7.47 (m, 7H), 6.96 (d, 2H), 5.06 (s, 2H), 4.23 (q, 2H), 4.15 (dd, 1H), 3.90 (dd, 1H), 2.17-2.28 (m, 1H), 2.07-2.17 (m, 2H), 1.61-1.76 (m, 1H), 1.31 (t, 3H).

Description 18: 1-(1,1-Dimethylethyl) 2-ethyl (2R, 5S)-5-{4-[(phenylmethyl)oxy]phenyl}-1,2-pyrrolidinedicarboxylate (D18)

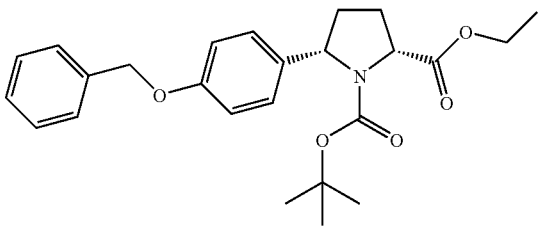

The title compound was prepared (1.85 g, 79%) using a similar procedure as set out earlier in Description 6 using ethyl (5S)-5-{4-[(phenylmethyl)oxy]phenyl}-D-prolinate (D17, 1.5 g, 4.61 mmol); $R_t$ (HPLC): 6.79 min; MS: (ES/+) m/z: 448 [M+Na$^+$]); C25H31NO5 requires 425; $^1$H NMR (400 MHz, CDCl$_3$) δ(ppm): 7.47-7.52 (m, 2H); 7.42-7.47 (m, 2H); 7.36-7.42 (m, 2H); 7.30-7.36 (m, 1H); 6.95 (d, 2H); 5.06, 5.08 (s, s, 2H); 4.40-4.52, 4.91-5.00 (m, m, 1H); 4.34, 4.71 (t, t, 1H); 4.21-4.31 (m, 2H); 2.14-2.36 (m, 2H); 1.87-2.13 (m, 2H); 1.17, 1.43 (s, s, 9H); 1.30-1.39 (m, 3H).

Description 19: 1-(1,1-Dimethylethyl) 2-ethyl (2R, 5S)-2-methyl-5-{4-[(phenylmethyl)oxy]phenyl}-1,2-pyrrolidinedicarboxylate (D19)

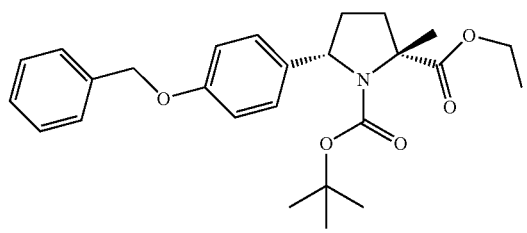

The title compound was prepared (375 mg, 43%) using a similar procedure as set out earlier in Description 7 using 1-(1,1-dimethylethyl) 2-ethyl (2R,5S)-5-{4-[(phenylmethyl)oxy]phenyl}-1,2-pyrrolidinedicarboxylate (D18, 850 mg, 2 mmol); $R_t$ (HPLC): 6.99 min; MS: (ES/+) m/z: 462 [M+Na$^+$]; C26H33NO5 requires 439; $^1$H-NMR (300 MHz, CDCl$_3$) δ(ppm); 7.28-7.52 (br.m., 7H); 6.89-6.97 (br.m., 2H); 4.80-5.10 (m, 3H); 4.18-4.38 (m, 2H); 2.38-2.52 (br.m., 1H); 2.25-2.37 (br.m., 1H); 1.76-1.90 (br.m., 2H); 1.54-1.63 (m, 3H); 1.31-1.47 (br.m., 9H); 1.09-1.16 (m, 3H).

Description 20: (5S)-1-{[(1,1-Dimethylethyl)oxy]carbonyl}-2-methyl-5-{4-[(phenylmethyl)oxy]phenyl}-D-proline (D20)

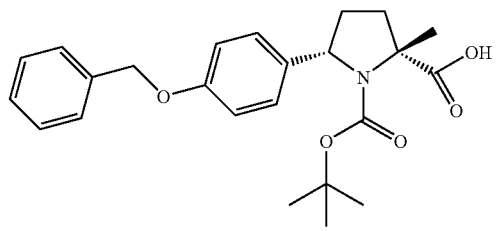

The title compound was prepared (300 mg, 87%) using a similar procedure as set out earlier in Description 8 using 1-(1,1-dimethylethyl) 2-ethyl (2R,5S)-2-methyl-5-{4-[(phenylmethyl)oxy]phenyl}-1,2-pyrrolidinedicarboxylate (D19, 370 mg, 0.84 mmol); R$_t$ (HPLC): 6.02 min; MS: (ES/+) m/z: 434 [M+Na$^+$]; C24H29NO5 requires 411; $^1$H-NMR (300 MHz, DMSO-d$_6$) δ(ppm): 12.57 (br.s., 1H); 7.28-7.49 (m, 7H); 6.89-6.97 (m, 2H); 5.08, 5.09 (s, s, 2H); 4.77, 4.87 (d, d, 1H); 2.38-2.49 (m, 1H); 2.07-2.21 (m, 1H); 1.73-1.83 (m, 1H); 1.60-1.73 (m, 1H); 1.45, 1.48 (s, s, 3H); 1.05, 1.34 (s, s, 9H).

Description 21: 1,1-Dimethylethyl (2R,5S)-2-(aminocarbonyl)-2-methyl-5-{4-[(phenylmethyl)oxy]phenyl}-1-pyrrolidinecarboxylate (D21)

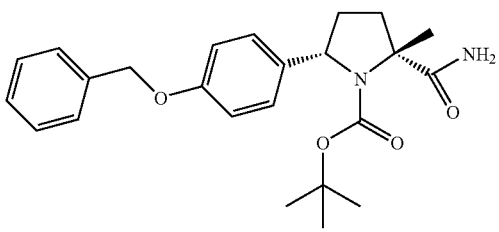

The title compound was prepared (220 mg, 73%) using a similar procedure as set out earlier in Description 9 using (5S)-1-{[(1,1-dimethylethyl)oxy]carbonyl}-2-methyl-5-{4-[(phenylmethyl)oxy]phenyl}-D-proline (D20, 300 mg, 0.73 mmol); R$_t$ (HPLC): 5.83 min; MS: (ES/+) 433 m/z: [M+Na$^+$]; C24H30N2O4 requires 410; R$_f$ (cyclohexane:ethyl acetate=7:3): 0.23.

Description 22: 1,1-Dimethylethyl (2S,5R)-2-(aminocarbonyl)-5-(4-hydroxyphenyl)-2-methyl-1-pyrrolidinecarboxylate (D22)

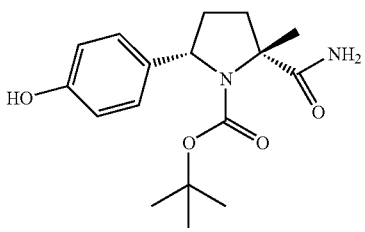

The title compound was prepared (140 mg, 90%) using a similar procedure as set out earlier in Description 10 using 1,1-dimethylethyl (2R,5S)-2-(aminocarbonyl)-2-methyl-5-{4-[(phenylmethyl)oxy]phenyl}-1-pyrrolidinecarboxylate (D21, 200 mg, 0.49 mmol); R$_t$ (HPLC): 3.98 min; MS: (ES/+) m/z: 343 [M+Na$^+$]; C17H24N2O4 requires 320; $^1$H NMR (500 MHz, DMSO-d$_6$) δ ppm: 9.16 (s, 1 H), 7.28-7.42 (m, 1 H), 7.16-7.26 (m, 2 H), 7.02-7.14 (m, 1 H), 6.57-6.71 (m, 2 H), 4.56-4.85 (m, 1 H), 2.07-2.41 (m, 2 H), 1.52-1.77 (m, 2 H), 1.44-1.57 (m, 3 H), 0.87-1.45 (m, 9 H).

Description 23: 1,1-Dimethylethyl (2R,5S)-2-(aminocarbonyl)-5-(4-{[(2-fluorophenyl)methyl]oxy}phenyl)-2-methyl-1-pyrrolidinecarboxylate (D23)

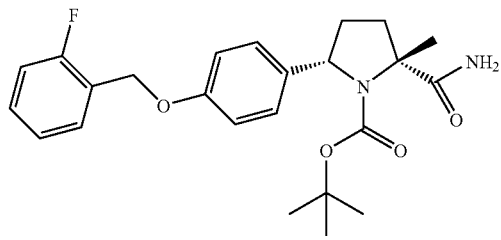

The title compound was prepared (80 mg) using a similar procedure as set out earlier in Description 11 starting from 1,1-dimethylethyl (2S,5R)-2-(aminocarbonyl)-5-(4-hydroxyphenyl)-2-methyl-1-pyrrolidinecarboxylate (D22, 55 mg, 0.17 mmol)) and 2-fluorobenzyl bromide; R$_t$ (HPLC): 5.87 min; MS: (ES/+) 451 m/z: [M+Na$^+$]; C24H29FN2O4 requires 428.

Description 24: 1-(1,1-Dimethylethyl) 2-methyl (2R,5R)-2-(cyanomethyl)-5-{4-[(phenylmethyl)oxy]phenyl}-1,2-pyrrolidinedicarboxylate (D24)

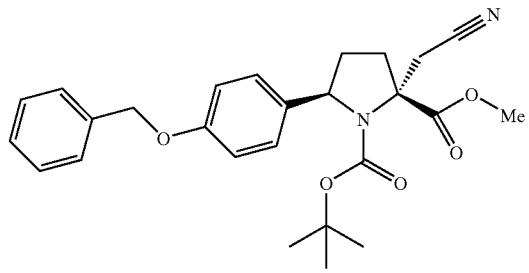

The title compound was prepared (2.71 g, 76%) using a similar procedure t as set out earlier in Description 7 using crude 1-(1,1-dimethylethyl) 2-methyl (2S,5R)-5-{4-[(phenylmethyl)oxy]phenyl}-1,2-pyrrolidinedicarboxylate (D6, 3.25 g, 7.89 mmol) and bromoacetonitrile (3.3 ml, 47.38 mmol in 40 ml THF); R$_t$ (HPLC): 6.4 min; R$_f$(cyclohexane:ethyl acetate=7:3): 0.40; MS: (ES/+) m/z: 473 [M+Na$^+$]; C26H30N2O5 requires 450; $^1$H NMR (500 MHz, DMSO-d$_6$) δ(ppm): 7.46-7.24 (m, 7H); 6.94 (d, 2H); 5.11 (s, 2H); 4.94-4.78 (m, 1H); 3.78 (s, 3H); 3.33 (d, 1H); 3.22 (d, 1H); 2.66-2.52 (m, 1H); 2.42-2.29 (m, 1H); 2.29-2.16 (m, 1H); 1.92-1.77 (m, 1H); 1.38-0.97 (br. s, 9H); NOE between the aromatic protons and the methyl ester could be observed.

Description 25: 1,1-Dimethylethyl (2R,5R)-2-(4-hydroxyphenyl)-6-oxo-1,7-diazaspiro[4.4]nonane-1-carboxylate (D25)

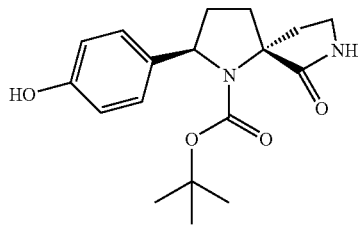

To a solution of 1-(1,1-dimethylethyl) 2-methyl (2R,5R)-2-(cyanomethyl)-5-{4-[(phenylmethyl)oxy]phenyl}-1,2-pyrrolidinedicarboxylate (D24, 2.7 g, 5.99 mmol): in methanol (50 ml) was added Raney Nickel (slurry in water) and the mixture was stirred under a hydrogen atmosphere (7 atmospheres) for 14 hours. The catalyst was filtered off, the solvent removed under reduced pressure, and the solid residue was treated with toluene (3×20 ml) and dried under vacuum. The dry white solid obtained was refluxed in methanol (40 ml) for five hours until cyclization was complete. The solvent was removed under reduced pressure and the crude material purified by chromatography on silica gel using dichloromethane/methanol (95:5 to 90:10) to afford the title compound as a white solid (1.35 g, 68%); $R_t$ (HPLC): 3.91 min; $R_f$ (dichloromethane:methanol=9:1): 0.41; MS: (ES/+) m/z: 665 [M+Na+], 355 [M+Na+]; C18H24N2O4 requires 332; $^1$H NMR (400 MHz, DMSO-$d_6$) δ(ppm): 9.11 (s, 1H); 7.76 and 7.66 (s, s, 1H); 7.43 (dd, 2H); 6.66 (dd, 2H); 4.81-4.70 (m, 1H); 3.29-3.20 (m, 1H); 3.19-3.09 (m, 1H); 2.47-2.20 (m, 2H); 2.08-1.85 (m, 2H); 1.84-1.74 (m, 1H); 1.68-1.52 (m, 1H); 1.33 and 1.08 (s, s, 9H).

Description 26: 1,1-Dimethylethyl (2R,5R)-2-(4-{[(2-fluorophenyl)methyl]oxy}phenyl)-6-oxo-1,7-diazaspiro[4.4]nonane-1-carboxylate (D26)

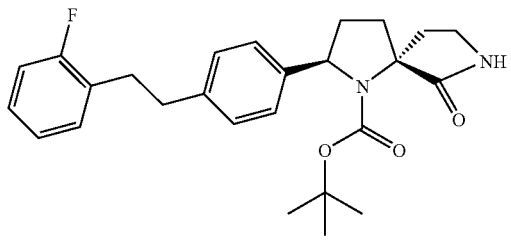

Method a):

The title compound was prepared using a similar procedure as set out earlier in Description 11 starting from 1,1-dimethylethyl (2R,5R)-2-(4-hydroxyphenyl)-6-oxo-1,7-diazaspiro[4.4]nonane-1-carboxylate (D25, 850 mg, 2.55 mmol) and 2-fluorobenzyl bromide (0.5 ml, 3.83 mmol); $R_t$ (HPLC): 5.72 min; $R_f$ (cyclohexane:ethyl acetate=3:7): 0.45; MS: (ES/+) m/z: 463 [M+Na+]. C25H29FN2O4 requires 440; $^1$H NMR (400 MHz, CDCl$_3$) δ(ppm): 7.61 (d, 2H); 7.56-7.49 (m, 1H); 7.35-7.28 (m, 1H); 7.20-7.13 (m, 1H); 7.12-7.05 (m, 1H); 7.00-6.94 (dd, 2H); 5.64 and 5.61 (s, s, 1H); 5.14 and 5.12 (s, s, 2H); 5.08 and 4.88 (d, d, 1H); 3.58-3.40 (m, 1H); 3.38-3.24 (m, 1H); 2.82-2.56 (m, 1H); 2.43-2.21 (m, 2H); 2.15-2.00 (m, 1H); 1.95-1.75 (m, 2H), 1.45 and 1.17 (s, s, 9H).

Method b):

To a solution of 1-(1,1-dimethylethyl) 2-methyl (2R,5R)-2-(cyanomethyl)-5-(4-{[(2-fluorophenyl)methyl]oxy}phenyl)-1,2-pyrrolidinedicarboxylate (D85, 51.3 g) in MeOH (~500 mL) was added CoCl$_2$.6H$_2$O (13.04 g). To the resulting purple solution were added three batches of NaBH$_4$ (8.29 g, 8.299 and 4.145 g respectively; exothermic addition) portionwise every 30 minutes. The reaction mixture was cooled down to ambient temperature, filtered and the resulting solution was heated to reflux overnight. Then the mixture was cooled down and filtered. NH$_4$Cl saturated solution (513 mL) was added and MeOH evaporated in vacuo. The aqueous phase was extracted with EtOAc (2×500 mL) and the combined organic phase was evaporated to dryness and the crude material was purified by chromatography on silica gel pad using cyclohexane and ethyl acetate (1:1, 4:6, 3:7) affording the title compound (22.1 g) as a white solid.

1H NMR (400 MHz, CHCl$_3$-d) δ(ppm): 7.61 (m, 2H), 7.53 (m, 1H), 7.31 (m, 1H), 7.16 (m, 1H), 7.09 (m, 1H), 6.97 (m, 2H), 5.58 (s, 1H), 5.14 (m, 2H), 5.04-4.86 (m, 1H), 3.58-3.42 (m, 1H), 3.32 (m, 1H), 2.80-2.58 (m, 1H), 2.32 (m, 2H), 2.07 (m, 1H), 1.93-1.78 (m, 2H), 1.45 (s, 3H), 1.17 (s, 6H).

Description 27: 1,1-Dimethylethyl (2R,5R)-2-(4-{[(2-cyanophenyl)methyl]oxy}phenyl) 6-oxo-1,7-diazaspiro[4.4]nonane-1-carboxylate (D27)

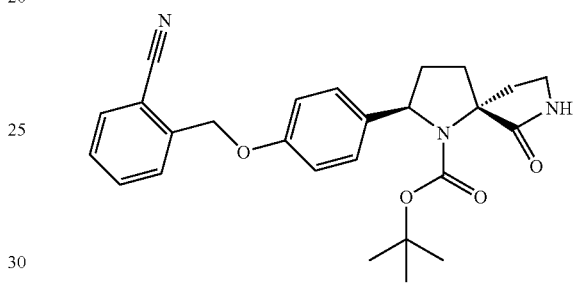

The title compound (102 mg, 90%) was prepared using a similar procedure as set out earlier in Description 11 starting from 1,1-dimethylethyl (2R,5R)-2-(4-hydroxyphenyl)-6-oxo-1,7-diazaspiro[4.4]nonane-1-carboxylate (D25, 84 mg, 0.252 mmol) and 2-cyanobenzyl bromide (74 mg, 1.5 eq); $R_t$ (HPLC): 5.37 min; $R_f$ (cyclohexane:ethyl acetate=1:1): 0.07; MS: (ES/+) m/z: 470 [M+Na+]. C26H29N3O4 requires 447.

Description 28: 1,1-Dimethylethyl (2R,5R)-2-{4-[(2-cyanophenyl)oxy]phenyl}-6-oxo-1,7-diazaspiro[4.4]nonane-1-carboxylate (D28)

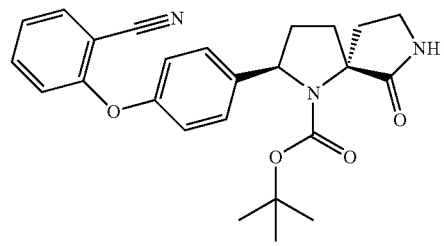

1,1-Dimethylethyl (2R,5R)-2-{4-[(2-cyanophenyl)oxy]phenyl}-6-oxo-1,7-diazaspiro[4.4]nonane-1-carboxylate (D28, 58 mg, 66%) was synthesized using a similar procedure as set out earlier in Description 13 using 1,1-dimethylethyl (2S,5R)-2-(aminocarbonyl)-5-(4-hydroxyphenyl)-2-methyl-1-pyrrolidinecarboxylate (D25, 66 mg, 0.198 mmol) and 2-fluoro-benzonitrile; $R_t$ (HPLC): 5.34 min; MS: (ES/+) m/z: 456 [M+Na+]; C25H27N3O4 requires 433.

Description 29: 1,1-Dimethylethyl (2R,5R)-2-(4-{[(2-fluorophenyl)methyl]oxy}phenyl)-7-methyl-6-oxo-1,7-diazaspiro[4.4]nonane-1-carboxylate (D29)

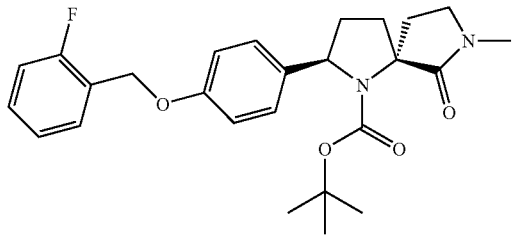

To a solution of 1,1-dimethylethyl (2R,5R)-2-(4-{[(2-fluorophenyl)methyl]oxy}phenyl)-6-oxo-1,7-diazaspiro[4.4]nonane-1-carboxylate (D26) (70 mg, 0.159 mmol) in dry DMF (1 ml) at 0° C. was added NaH 60% wt dispersion in mineral oil (10 mg, 0.238 mmol); after 15 minutes of stirring at room temperature, iodomethane (30 μl, 0.477 mmol) was added and the resulting mixture was stirred at room temperature for 2.5 hours. The mixture was cooled to 0° C., and water (4 ml) and ethyl acetate (10 ml) were added, the organic layer was washed with ice cold brine (3×10 ml), dried over $Na_2SO_4$ and evaporated. The crude material was purified by chromatography on silica gel using cyclohexanes/ethyl acetate (7:3) to afford the title compound as a white solid (63 mg, 88%); $R_t$ (HPLC): 5.99 min; $R_f$ (cyclohexane:ethyl acetate=1:1): 0.28; MS: (ES/+) m/z: 477 [M+Na$^+$]; C26H31FN2O4 requires 454. $^1$H NMR (400 MHz, CDCl$_3$) δ(ppm): 7.66 (d, 2H); 7.56-7.49 (m, 1H); 7.35-7.25 (m, 1H); 7.20-7.13 (m, 1H); 7.12-7.04 (m, 1H); 6.97 (dd, 2H); 5.14 and 5.12 (s, s, 2H); 5.02 and 4.88 (d, d, 1H); 3.52-3.45 and 3.41-3.22 (m, m, 2H); 2.96 and 2.92 (s, s, 3H); 2.67-2.56 and 2.53-2.42 (m, m, 1H); 2.40-2.22 (m, 2H); 2.08-1.79 (m, 2H); 1.77-1.68 (m, 1H), 1.40 and 1.16 (s, s, 9H).

Description 30: 1-{[(4-Bromophenyl)oxy]methyl}-2-fluorobenzene 4-bromophenyl (2-fluorophenylmethyl ether (D30)

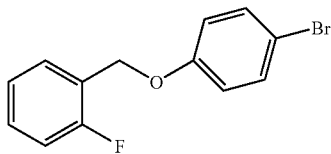

4-Bromophenol (1200 g) was dissolved in acetone (15000 mL), $K_2CO_3$ (1362 g) was first added and then benzylbromide (1250 g). The mixture was refluxed for about 2 hrs. The reaction mixture was then cooled at 25° C., filtered and washed with MTBE (2500 mL). The organic solution was concentrated to 2500 mL, 10000 mL of MTBE were added and then it was washed with NaOH 1M (3500 mL), with brine (3125 mL) and concentrated to dryness. THF (6250 mL) was added and the solvent was removed under reduced pressure to afford the title compound (1784 g).

$^1$H NMR (400 MHz, DMSO-d$_6$) δ(ppm): 7.54 (td, 1H); 7.46 (d, 2H); 7.42 (m, 1H); 7.23 (m, 2H); 7.01 (d, 2H); 5.13 (s, 2H).

Description 31: Methyl (2S)-2-({[(1,1-dimethylethyl)oxy]carbonyl}amino)-5-(4-{[(2-fluorophenyl)methyl]oxy}phenyl)-5-oxopentanoate (D31)

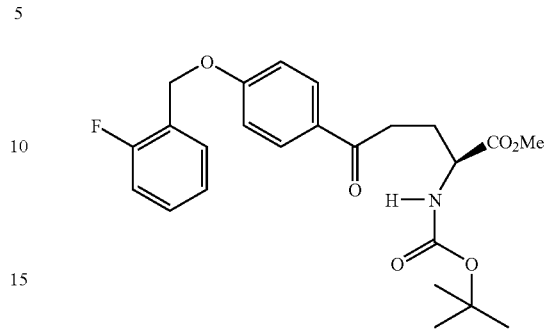

To a stirring suspension of Mg (120 g) in dry THF (800 mL) under $N_2$ at room temperature, was added 12 (0.4 g). The mixture was heated to an internal temperature of 63±2° C. A solution of 1-{[(4-bromophenyl)oxy]methyl}-2-fluorobenzene 4-bromophenyl (2-fluorophenyl)methyl ether (D30, 924 g) in THF (2000 mL) was added as according to the following procedure: a first batch of the solution (60 mL) was added; then the remaining solution (~2900 mL) was added dropwise. After the end of the addition the reaction was maintained at reflux for 1 h. After this time, the reaction was cooled to room temperature. A solution of 1-(1,1-dimethylethyl) 2-methyl (2S)-5-oxo-1,2-pyrrolidinedicarboxylate (400 g) in THF (2000 mL) was cooled at −60° C. The organomagnesium solution previously prepared as above described was added over the solution of 1-(1,1-dimethylethyl) 2-methyl (2S)-5-oxo-1,2-pyrrolidinedicarboxylate slowly, and maintaining the internal temperature below −60° C. The addition was completed in 3 h and 20 min. The reaction was stirred for 1 h after the addition of the organomagnesium solution was completed. IPA (400 mL) was added dropwise to the solution, and the temperature was maintained below −45° C. Then a solution of $NH_4Cl$ sat/NaCl sat=2/1 (1200 mL) was added maintaining the temperature at −45° C. Water (800 mL) was added to dissolve the yellow precipitate. The collected organics were washed with NaCl aq 13% (800 mL) and concentrated to dryness. EtOAc (6000 mL) was then added and the solution was evaporated under reduced pressure to remove water. The residue was partially dissolved in EtOAc (~400 mL) leading to a crop that was isolated by filtration (273 g). The liquors were concentrated to dryness; EtOAc (~200 mL) and cyclohexane (~400 mL) were added leading to a suspension that was filtered giving a second crop (66 g). $^1$H NMR (600 MHz, DMSO-d$_6$) δ(ppm): 7.93 (d, 2H); 7.57 (td, 1H); 7.44 (m, 1H); 7.27 (m, 3H); 7.14 (d, 2H); 5.24 (s, 2H); 4.04 (m, 1H); 3.61 (s, 3H); 3.03 (m, 2H); 1.94 (m, 2H); 1.38 (s, 9H).

Description 32: Methyl (2S)-5-(4-{[(2-fluorophenyl)methyl]oxy}phenyl)-3,4-dihydro-2H-pyrrole-2-carboxylate (D32)

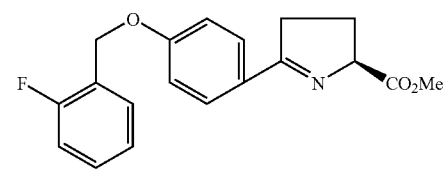

To a solution of methyl (2S)-2-({[(1,1-dimethylethyl)oxy]carbonyl}amino)-5-(4-{[(2-fluorophenyl)methyl]oxy}phenyl)-5-oxopentanoate (D31, 339 g) in dry DCM (3390 mL), at 0° C., was added trifluoroacetic acid (TFA) (640 mL) dropwise. The mixture was allowed to warm to room temperature and stirred for 2 hrs. Solvent and excess TFA were removed under vacuum and the resulting dark oil was stripped with EtOAc (1700 mL) and left overnight under high vacuum. The title compound was obtained as a red oil (818 g). $^1$H NMR (400 MHz, DMSO-$d_6$) δ(ppm): 8.16 (m, 2H); 7.60 (td, 1H); 7.46 (m, 1H); 7.34 (m, 2H); 7.27 (m, 2H); 5.32 (s, 2H); 5.25 (m, 1H); 3.77 (s, 3H); 3.57 (m, 2H); 2.60 (m, 1H); 2.34 (m, 1H).

Description 33: Methyl (5R)-5-(4-{[(2-fluorophenyl)methyl]oxy}phenyl)-L-prolinate (D33)

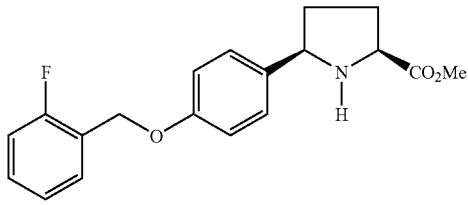

Methyl (2S)-5-(4-{[(2-fluorophenyl)methyl]oxy}phenyl)-3,4-dihydro-2H-pyrrole-2-carboxylate (D32) was split in three batches. The first batch of methyl (2S)-5-(4-{[(2-fluorophenyl)methyl]oxy}phenyl)-3,4-dihydro-2H-pyrrole-2-carboxylate (D32, 10 g) was dissolved with EtOAc (100 mL) in a hydrogenation reactor. Pt/C Degussa type F101 RA/W (5% of Pt on C, moisture content ca. 50%, 0.7 g) was added, then the reactor was filled with $H_2$, pressurizing to 2 atm. The reaction was started by switching the stirrer on, and left for ca. 2 hours under stirring. The reactor was vented, the spent catalyst was filtered off through Celite, and washed with EtOAc (2×50 mL). This solution was treated with a 13% w/w solution of $Na_2CO_3$ (50 mL). The mixture was stirred for at least 10 minutes, and phases were then allowed to separate. The aqueous phase was removed. The resulting solution was concentrated to dryness (3.329). The second batch of methyl (2S)-5-(4-{[(2-fluorophenyl)methyl]oxy}phenyl)-3,4-dihydro-2H-pyrrole-2-carboxylate (D32, 300 g) was dissolved with EtOAc (3000 mL) in a hydrogenation reactor. Pt/C Degussa type F101 RA/W (5% of Pt on C, moisture content ca. 50%, 21 g) was added, then the reactor was filled with $H_2$, pressurizing to 2 atm. The reaction was started by switching the stirrer on, and left for ca. 2 hours under stirring. The reactor was vented, the spent catalyst was filtered off through Celite, and washed with EtOAc (2×900 mL). This solution was treated with a 15% w/w solution of $Na_2CO_3$ (1500 mL). The mixture was stirred for at least 10 minutes, and phases were then allowed to separate. The aqueous phase was removed, and then the organic layer was washed once with NaCl 20% w/w (1500 mL). The resulting solution was concentrated to dryness (127 g). The third batch of methyl (2S)-5-(4-{[(2-fluorophenyl)methyl]oxy}phenyl)-3,4-dihydro-2H-pyrrole-2-carboxylate (D32, 360 g) was dissolved with EtOAc (3600 mL) in a hydrogenation reactor. Pt/C Degussa type F101 RA/W (5% of Pt on C, moisture content ca. 50%, 25.29) was added, then the reactor was filled with $H_2$, pressurizing to 2 atm. The reaction was started by switching the stirrer on, and left for ca. 1.5 hours under stirring. The reactor was vented, the spent catalyst was filtered off through Celite, and washed with EtOAc (2×720 mL). This solution was treated with a 15% w/w solution of $Na_2CO_3$ (1800 mL). The mixture was stirred for at least 10 minutes, and phases were then allowed to separate. The aqueous phase was removed, and then the organic layer was washed once with NaCl 20% w/w (1800 mL). The resulting solution was concentrated to dryness (141 g). The three combined residues were purified by flash chromatography eluting with cyclohexane/ethyl acetate (from 6:4 to 4:5) to afford the title compound (186.4 g). $^1$H NMR (600 MHz, DMSO-$d_6$) δ(ppm): 7.55 (dt, 1H); 7.41 (m, 1H); 7.34 (m, 2H); 7.23 (m, 2H); 6.97 (m, 2H); 5.12 (s, 2H); 4.09 (dd, 1H); 3.83 (dd, 1H); 3.66 (s, 3H); 2.97 (bs, 1H); 2.04 (m, 2H); 1.94 (m, 1H); 1.52 (m, 1H).

Description 34: 1-(1,1-Dimethylethyl) 2-methyl (2S, 5R)-5-(4-{[(2-fluorophenyl)methyl]oxy}phenyl)-1,2-pyrrolidinedicarboxylate (D34)

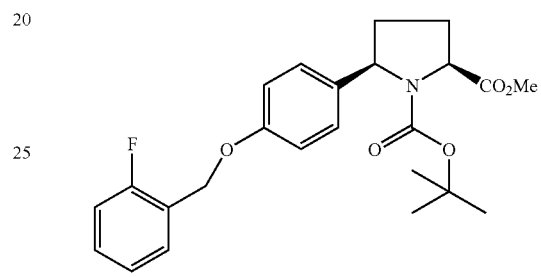

Methyl (5R)-5-(4-{[(2-fluorophenyl)methyl]oxy}phenyl)-L-prolinate (D33, 175 g) was dissolved in EtOAc (1000 mL) and cooled to 0° C. A solution of di-tert-butyl-dicarbonate (127.5 g) in EtOAc (750 mL) was added dropwise in about 1 hour maintaining the temperature at about 0° C. Then the temperature was increased to 25° C. and the reaction stirred at 25° C. for 2 hours. 28% w/w Racemic malic acid (350 mL) was added and the mixture stirred for about 10 min. The organic phase was washed with saturated NaHCO₃ (700 mL). Aqueous pH was ~8. The organic phase was concentrated to a low volume then stripped with cyclohexane (3×350 mL) to afford the title compound (240.8 g). $^1$H NMR (400 MHz, CDCl₃) δ(ppm): 7.54 (m, 1H); 7.50 (d, 2H), 7.33 (m, 1H); 7.18 (dt, 1H); 7.11 (m, 1H); 6.98 (d, 2H); 5.16 (2s, 2H); 4.97-4.46 (2bm, 1H); 4.73-4.37 (2t, 1H); 3.83 (s, 3H); 2.32 (m, 1H); 2.21 (m, 1H); 2.08 (m, 1H); 1.96 (m, 1H); 1.43-1.18 (2bs, 9H).

Description 35: 1-(1,1-Dimethylethyl) 2-methyl (2R, 5R)-5-(4-{[(2-fluorophenyl)methyl]oxy}phenyl)-2-(2-propen-1-yl)-1,2-pyrrolidinedicarboxylate (D35)

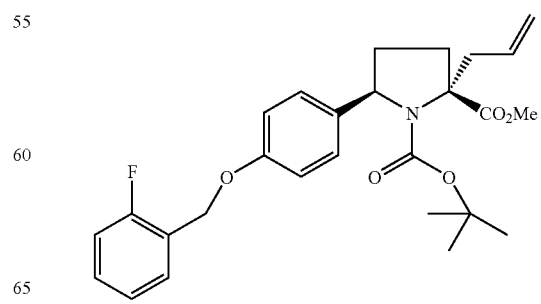

The previous crude of 1-(1,1-dimethylethyl) 2-methyl (2S, 5R)-5-(4-{[(2-fluorophenyl)methyl]oxy}phenyl)-1,2-pyrrolidinedicarboxylate (D34) was split in two batches. The first one (100 g) was dissolved in dry THF (1000 mL) then allyl bromide (42.25 g) was added, finally the mixture was cooled to −30° C. 1M LiHMDS in THF (439 mL) was added dropwise in about 1.5 hours maintaining the temperature at about −30° C. Water (100 mL) was added and temperature allowed to reach 0° C. Saturated NH$_4$Cl (500 mL) was added followed by water (400 mL) and EtOAc (500 mL). The reaction was warmed to 25° C. and the aqueous layer was removed. The organic layer was concentrated to about 700 mL and washed with NaHCO$_3$ saturated solution (200 mL). Organic layer was dried over Na$_2$SO$_4$ and concentrated to afford the title compound as an oil (119.8 g). The second batch (135 g) was similarly reacted using dry THF (1350 mL), allyl bromide (57.04 g) and 1M LiHMDS in THF (471.5 mL). After workup, the title compound was isolated as an oil (179 g). $^1$H NMR (400 MHz, DMSO-d$_6$) δ(ppm): 7.53 (m, 1H); 7.39 (m, 3H); 7.22 (m, 2H); 6.95 (m, 2H); 5.82 (m, 1H); 5.12 (m, 4H); 4.80-4.59 (2m, 1H); 3.74-3.71 (2s, 3H); 3.01-1.52 (m, 6H); 1.29-0.98 (2s, 9H).

Description 36: 1-(1,1-Dimethylethyl) 2-methyl (2R, 5R)-2-(2,3-dihydroxypropyl)-5-(4 {[(2-fluorophenyl)methyl]oxy}phenyl)-1,2-pyrrolidinedicarboxylate (D36)

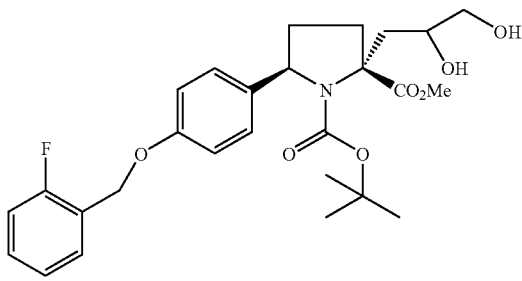

The reaction was performed on the two separated batches of 1-(1,1-dimethylethyl) 2-methyl (2R,5R)-5-(4-{[(2-fluorophenyl)methyl]oxy}phenyl)-2-(2-propen-1-yl)-1,2-pyrrolidinedicarboxylate obtained from the previous step (D35). The first batch (119.8 g) was dissolved in a mixture of 10/1 acetone/water (1200 mL). K$_2$OsO$_4$.2H$_2$O (4.7 g) was added followed by NMO (41.4 g) after a few minutes. The mixture was stirred for 7.5 hours. The reaction mixture was treated with EtOAc (1200 mL) and washed with saturated NH$_4$Cl (1200 mL) then with saturated NaHCO$_3$ (1200 mL). The organic layer was filtered through a celite/activated charcoal pad and concentrated to low volume. EtOAc (500 mL) was added and the solution was washed with brine (300 mL) and the organic dried over Na$_2$SO$_4$, and evaporated to dryness, EtOAc (300 mL) was added and filtered through CUNO filter and washed with EtOAc (50 mL). The organic was concentrated to dryness to afford the title compound (135 g). The second batch (179 g) was dissolved in a mixture of 10/1 acetone/water (1800 mL). K$_2$OsO$_4$.2H$_2$O (5.5 g) was added followed by NMO (56.8 g) after a few minutes. The mixture was stirred overnight at room temperature. The reaction mixture was treated with EtOAc (900 mL) and washed with saturated NH$_4$Cl (2×900 mL) then with saturated NaHCO$_3$ (900 mL). The organic layer was filtered through a celite pad and concentrated to low volume to afford the title compound (250 g). $^1$H NMR (400 MHz, DMSO-d$_6$) δ(ppm): 7.54 (m, 1H); 7.40 (m, 3H); 7.22 (m, 2H); 6.95 (m, 2H); 5.11 (m, 2H); 4.95-4.25 (m, 3H); 3.70 (bm, 3H); 3.50-3.10 (m, 3H); 2.50-1.50 (m, 6H); 1.30-0.95 (4bs, 9H).

Description 37: 1-(1,1-Dimethylethyl) 2-methyl (2R, 5R)-5-(4-{[(2-fluorophenyl)methyl]oxy}phenyl)-2-(2-oxoethyl)-1,2-pyrrolidinedicarboxylate (D37)

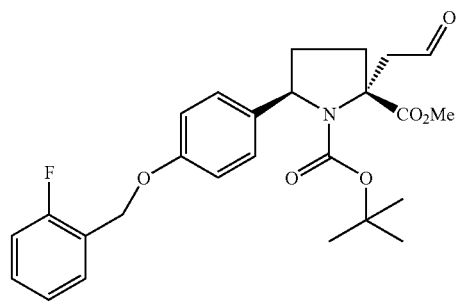

Procedure 1: The reaction was performed on the two separated batches of 1-(1,1-dimethylethyl) 2-methyl (2R,5R)-2-(2,3-dihydroxypropyl)-5-(4-{[(2-fluorophenyl)methyl]oxy}phenyl)-1,2-pyrrolidinedicarboxylate obtained from the previous step (D36). The first batch (135 g) was dissolved in a mixture of 10/1 acetone/water (2000 mL) and NaIO$_4$ (74.54 g) was added. The solution turned from brown to yellow and a suspension was formed. The mixture was stirred overnight at 25° C. Further NaIO$_4$ (2×5.73 g) was added and stirred for further 24 hours. EtOAc (1000 mL) was added followed by water (1000 mL). After mixing the aqueous phase was removed. The organic phase was concentrated to a yellow oil and stripped with EtOAc (250 mL) to afford the title compound (109 g). The second batch (250 g) was dissolved in a mixture of 10/1 acetone/water (1900 mL) and NaIO$_4$ (1069) was added. The solution turned from brown to yellow and a suspension was formed. The mixture was stirred for 6 hours then further NaIO$_4$ (8.15 g) was added and stirred overnight. EtOAc (1000 mL) was added followed by water (2000 mL). After mixing the aqueous phase was removed. The organic phase was concentrated to a yellow oil and stripped with EtOAc (300 mL) to afford the title compound (180 g).

$^1$H NMR (400 MHz, DMSO-d$_6$) δ(ppm): 9.72 (m, 1H); 7.56 (m, 1H); 7.42 (m, 3H); 7.24 (m, 2H); 6.99 (m, 2H); 5.14 (m, 2H) 4.90-4.79 (2m, 1H); 3.80-3.77 (2s, 3H); 3.02 (m, 1H); 2.83 (m, 1H); 2.55-1.55 (m, 4H); 1.32-1.03 (2s, 9H).

D37 was also obtained through the alternative procedure described below:

Procedure 2: A solution of 1-(1,1-dimethylethyl) 2-methyl (2R,5R)-5-(4-{[(2-fluorophenyl)methyl]oxy}phenyl)-2-(2-propen-1-yl)-1,2-pyrrolidinedicarboxylate (D35, 15 g) in methanol (200 ml) was cooled to −10° C. Ozone gas was passed through the solution for 2 hours, then the mixture was warmed to 0-5° C., Dimethylsulphide (7.04 ml) was added and the mixture stirred for 1 hours at 0-5° C., then at room temperature for 3 hours. The mixture was then concentrated under vacuum at 35-50° C. to give a residue. This was treated with water (45 ml), then extracted with DCM (2×37.5 ml). The combined extracts were stirred with a mixture of 60-120 mesh silica gel (45 g, DCM (75 ml) and 10% oxalic acid (6 ml) for 4 hours. The mixture was then filtered and washed with DCM (75 ml). The combined filtrates were washed with water (75 ml) and 10% sodium bicarbonate (75 ml) and water (75 ml). The solution was then dried over sodium sulphate and evaporated, then dried under vacuum to give the title compound as a brownish yellow pasty mass (12.7 g).

Description 38: 1-(1,1-Dimethylethyl) 2-methyl (2R, 5R)-5-(4-{[(2-fluorophenyl)methyl]oxy}phenyl)-2-[2-(methylamino)ethyl]-1,2-pyrrolidinedicarboxylate (D38)

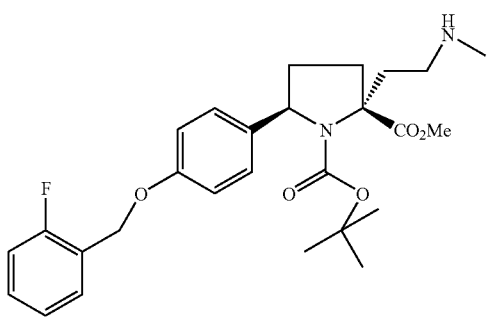

The reaction was performed on the two separated batches of 1-(1,1-dimethylethyl) 2-methyl (2R,5R)-5-(4-{[(2-fluorophenyl)methyl]oxy}phenyl)-2-(2-oxoethyl)-1,2-pyrrolidinedicarboxylate obtained from the previous step (D37, Procedure 1). The first batch (109 g) was dissolved in MeOH (440 mL) and MeNH$_2$ in MeOH 2M solution (347 mL) was added. AcOH (11 mL) was added. NaBH(OAc)$_3$ (49 g) was added portion wise after 10 minutes. More NaBH(OAc)$_3$ (14.7 g) was added portion wise at 25° C. The reaction mixture was quenched with 28% aqueous malic acid (200 mL) followed by AcOEt (1000 mL). K$_2$CO$_3$ was added up to pH~9. Organic phase was concentrated to dryness, re-dissolved in EtOAc (500 mL) and extracted with 20% citric acid (4×300 mL). The combined aqueous phases were treated with EtOAc (500 mL) and solid K$_2$CO$_3$ was added until pH~9. The phases were separated and the organic phase was dried under Na$_2$SO$_4$ and evaporated to dryness to afford the title compound (80 g). The second batch (180 g) was dissolved in MeOH (628 mL) and MeNH$_2$ in MeOH 2M solution (300 mL) was added. AcOH (31 mL) was added. NaBH(OAc)$_3$ (78.8 g) was added portionwise at 0° C. after 10 minutes. The reaction mixture was quenched with saturated NH$_4$Cl (890 mL) and EtOAc (890 mL). The phases were separated and the aqueous was extracted with EtOAc (4×300 mL). The organic phase was dried over Na$_2$SO$_4$, concentrated to dryness, re-dissolved in EtOAc (500 mL) and extracted with 20% citric acid (6×150 mL). The combined aqueous phases were treated with EtOAc (600 mL) and solid K$_2$CO$_3$ was added until pH 8/9. The Phases were separated and the organic phase dried over Na$_2$SO$_4$ and evaporated to dryness to afford the title compound (78 g). $^1$H NMR (400 MHz, DMSO-d$_6$) δ(ppm): 7.55 (m, 1H); 7.42 (m, 3H); 7.25 (m, 2H); 6.98 (m, 2H); 5.14 (m, 2H); 4.85-4.69 (2m, 1H); 3.75-3.73 (2s, 3H); 2.36 (bs, 3H) 2.80-2.25 (m, 2H); 2.20-2.00 (m, 3H); 1.70 (m, 1H); 1.32-1.00 (2s, 9H).

Description 39: 3-Bromophenyl phenylmethyl ether (D39)

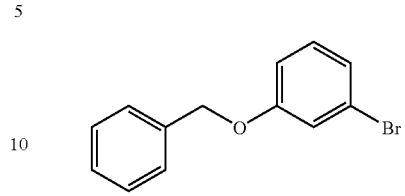

The title compound was synthesized (4.8 g, quant.) following a similar procedure as set out earlier in Description 54 starting from 3-bromophenol (3 g, 17.3 mmol) and benzylbromide (2.1 ml); R$_t$ (HPLC): 6.42 min.

Description 40: Methyl (2S)-2-({[(1,1-dimethylethyl)oxy]carbonyl}amino)-5-oxo-5-{3-[(phenylmethyl)oxy]phenyl}pentanoate (D40)

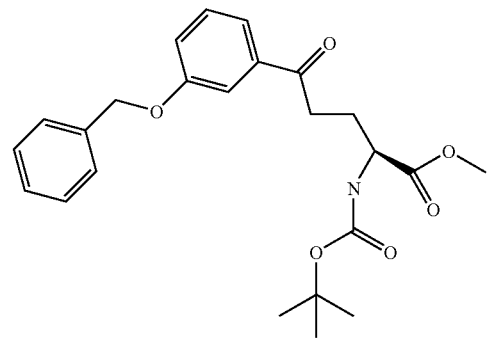

The title compound was synthesized (420 mg, 6%) following a similar procedure as set out earlier in Description 2 starting from 1-(1,1-dimethylethyl) 2-methyl (2S)-5-oxo-1,2-pyrrolidinedicarboxylate (D1, 3.69 g, 15.2 mmol) and 3-bromophenyl phenylmethyl ether (D39); R$_t$ (HPLC): 6.2 min.

Description 41: Methyl (2S)-5-{3-[(phenylmethyl)oxy]phenyl}-3,4-dihydro-2H-pyrrole-2-carboxylate (D41)

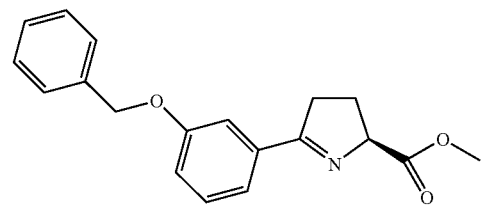

The title compound was synthesized (666 mg) following a similar procedure as set out earlier in Description 3 starting from methyl (2S)-2-({[(1,1-dimethylethyl)oxy]carbonyl}amino)-5-oxo-5-{3-[(phenylmethyl)oxy]- phenyl}pentanoate (D40, 420 mg, 1 mmol). The crude material was used in the next step without further purification. $R_t$ (HPLC): 3.99 min.

Description 42: Methyl (5R)-5-{3-[(phenylmethyl)oxy]phenyl}-L-prolinate (D42)

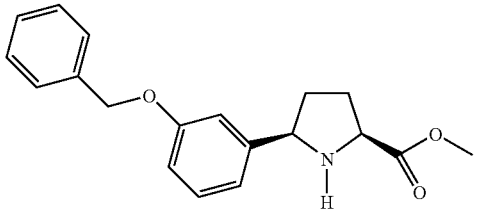

The title compound was synthesized (270 mg, 87%) following a similar method as set out earlier in Description 4 from methyl (2S)-5-{3-[(phenylmethyl)oxy]phenyl}-3,4-dihydro-2H-pyrrole-2-carboxylate (D41, 666 mg). $R_t$ (HPLC): 3.70 min; MS: (ES/+) m/z: 312 [MH$^+$], C19H21NO3 requires 311; $^1$H NMR (400 MHz, CHCl3-d) δ (ppm): 7.41 (d, 2H); 7.35 (t, 2H); 7.26-7.32 (m, 1H); 7.19-7.25 (m, 1H); 7.09 (t, 1H); 7.00 (d, 1H); 6.84 (dd, 1H); 5.04 (s, 2H); 4.17 (dd, 1H); 3.94 (dd, 1H); 3.74 (s, 3H); 2.01-2.24 (m, 3H); 1.63-1.75 (m, 1H).

Description 43: 1-(1,1-Dimethylethyl) 2-methyl (2S, 5R)-5-{3-[(phenylmethyl)oxy]phenyl}-1,2-pyrrolidinedicarboxylate (D43)

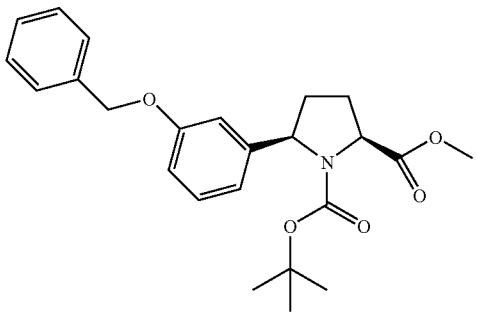

The title compound was synthesized (2.6 g, quant.) following a similar method as set out earlier in Description 6 starting from methyl (5R)-5-{3-[(phenylmethyl)oxy]phenyl}L-prolinate (D42, 1.66 g, 5.33 mmol). The crude material was used in the next step without further purification; $R_t$ (HPLC): 6.55 min.

Description 44: 1-(1,1-Dimethylethyl) 2-methyl (2R, 5R)-2-(cyanomethyl)-5-{3-[(phenylmethyl)oxy]phenyl}-1,2-pyrrolidinedicarboxylate (D44)

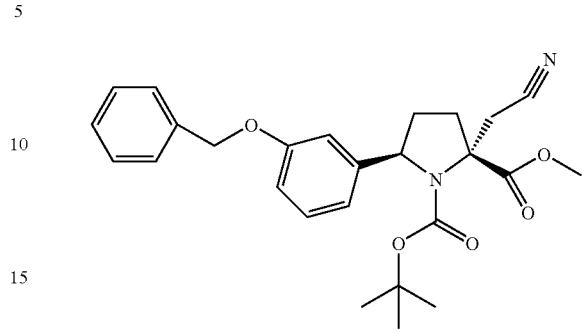

To a solution of 1-(1,1-dimethylethyl) 2-methyl (2S,5R)-5-{3-[(phenylmethyl)oxy]phenyl}-1,2-pyrrolidinedicarboxylate (D43, 1.93 g, 4.7 mmol) in dry THF (20 mL) at −78° C. was added LiHMDS (5.2 mL of a 1M solution in THF, 5.2 mmol). The mixture was allowed to warm to −30° C. and stirred for 30 min at this temperature. Then the yellow slurry was cooled to −78° C. and bromoacetonitrile (2.2 mL, 30.9 mmol) was added. The reaction mixture was left under stirring for 1 h and then quenched with a saturated ammonium chloride solution. The aqueous layer was extracted with ethyl acetate, dried (Na$_2$SO$_4$), filtered and evaporated. The crude material was purified by chromatography on silica gel using cyclohexane/ethyl acetate (9:1) affording the title compound (1.15 g, 54%); $^1$H NMR (400 MHz, CDCl$_3$) δ(ppm): 2/1 mixture of rotamers; 7.31-7.47 (m, 5H); 7.22-7.28 (m, 2H); 7.07-7.12 (m, 1H); 6.85-6.91 (m, 1H); 5.05-5.17 (m, 3H major+3H minor); 4.94 (bs, 1H major); 3.88 (br. s, 3H); 3.79 (br. s, 1H minor); 3.52 (d, 1H major); 3.05-2.28 (m, 1H major+1H minor); 2.62-2.77 (m, 1H); 2.39-2.57 (m, 1H); 2.23-2.33 (m, 1H); 1.92-2.08 (m, 1H); 1.44 (s, 9H minor); 1.14 (s, 9H major).

Description 45: 1,1-Dimethylethyl (2R,5R)-2-(3-hydroxyphenyl)-6-oxo-1,7-diazaspiro[4.4]nonane-1-carboxylate (D45)

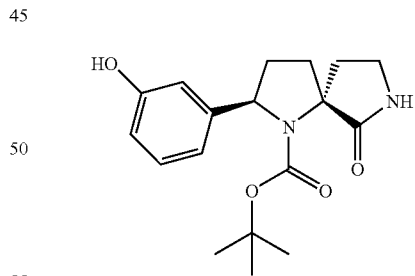

To a solution of 1-(1,1-dimethylethyl) 2-methyl (2R,5R)-2-(cyanomethyl)-5-{3-[(phenylmethyl)oxy]phenyl}-1,2-pyrrolidinedicarboxylate (D44, 1.15 g, 2.55 mmol) in methanol (40 mL) was added Raney Nickel (slurry in water, 10 g) and the mixture was stirred under a hydrogen atmosphere (7 atm) for 4 hours. The catalyst was filtered off, the solvent removed under reduced pressure, and the solid residue was treated with toluene (3×20 mL) and dried under vacuum. The crude oil obtained was refluxed in methanol (100 mL) for 7 hours until a complete cyclization was observed. The solvent was removed under reduced pressure and the crude material purified by chromatography on silica gel using dichloromethane/methanol (100:0 to 95:5) to afford the title compound (0.41 g, 48%).

Description 46: 1,1-Dimethylethyl (2R,5R)-2-(3-{[(2-fluorophenyl)methyl]oxy}phenyl)-6-oxo-1,7-diazaspiro[4.4]nonane-1-carboxylate (D46)

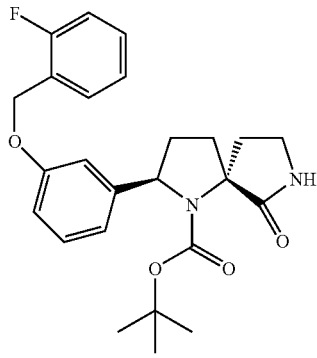

The title compound (0.420 g, 78%) was prepared from 1,1-dimethylethyl (2R,5R)-2-(3-hydroxyphenyl)-6-oxo-1,7-diazaspiro[4.4]nonane-1-carboxylate (D45, 410 mg, 1.23 mmol) and 2-fluorobenzyl bromide using a similar procedure to that set out earlier in Description 11.

Description 47: 1,1-Dimethylethyl (2R,5R)-2-(3-{[(2-fluorophenyl)methyl]oxy}phenyl)-7-methyl-6-oxo-1,7-diazaspiro[4.4]nonane-1-carboxylate (D47)

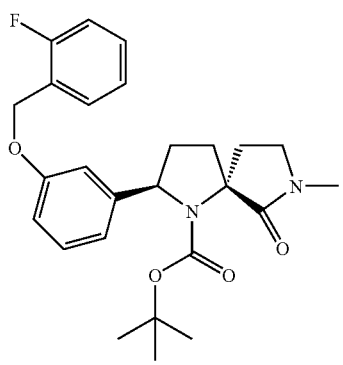

To a solution of 1,1-dimethylethyl (2R,5R)-2-(3-{[(2-fluorophenyl)methyl]oxy}phenyl)-6-oxo-1,7-diazaspiro[4.4]nonane-1-carboxylate (D46, 60 mg, 0.14 mmol) in DMF (1 mL) cooled at 0° C., was added NaH (8 mg of a 60% dispersion in mineral oil, 0.20 mmol) in one portion. The ice-bath was removed and the reaction mixture left under stirring for 15 min. Methyl iodide (25 μL, 0.41 mmol) was added to the mixture and after 1 h the reaction was quenched with water. The aqueous layer was extracted with ethyl acetate, dried ($Na_2SO_4$) and evaporated. The crude material was purified by chromatography on silica gel using cyclohexane/ethyl acetate (7:3) affording the title compound (70 mg, quant.); $R_t$ (HPLC): 6.03 min; MS: (ES/+) m/z: 477 [M+Na+]; $C_{26}H_{31}FN_2O_4$ requires 454.

Description 48: 1-(1,1-Dimethylethyl) 2-methyl (2R,5R)-2-[(2Z)-4-bromo-2-buten-1-yl]-5-(4-{[(2-fluorophenyl)methyl]oxy}phenyl)-1,2-pyrrolidinedicarboxylate (D48)

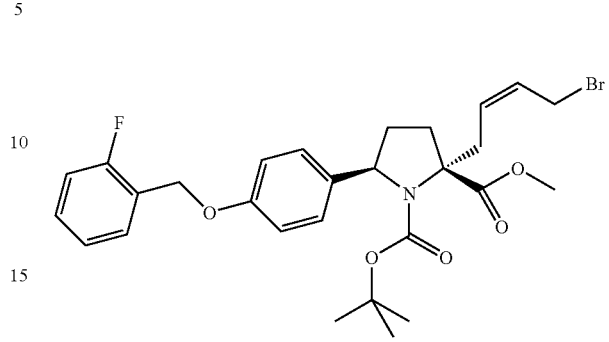

To a solution of 1-(1,1-dimethylethyl) 2-methyl (2S,5R)-5-(4-{[(2-fluorophenyl)methyl]oxy}phenyl)-1,2-pyrrolidinedicarboxylate (D34, 0.2 g, 0.47 mmol) in dry THF (2 mL) at −78° C. was added LiHMDS (0.51 mL of a 1M solution in THF, 0.51 mmol). The mixture was allowed to warm to −30° C. and stirred for 30 min at this temperature. The yellow slurry was cooled to −78° C. and (2Z)-1,4-dibromo-2-butene (0.30 mL, 2.81 mmol) was added. The reaction mixture was left under stirring for 40 min and then quenched with a saturated ammonium chloride solution. The aqueous layer was extracted with ethyl acetate, dried ($Na_2SO_4$) and evaporated. The crude material was purified by chromatography on silica gel using cyclohexane/ethyl acetate (9:1) affording the title compound (101 mg, 38%); $R_t$ (HPLC) 7.42 min. MS: (ES/+) m/z: 462 and 464 [MH+—Boc]; $C_{28}H_{33}BrFNO_5$ requires 562.

Description 49: 1-(1,1-Dimethylethyl) 2-methyl (2R,5R)-2-(2-cyanoethyl)-5-{4-[(phenylmethyl)oxy]phenyl}-1,2-pyrrolidinedicarboxylate (D49)

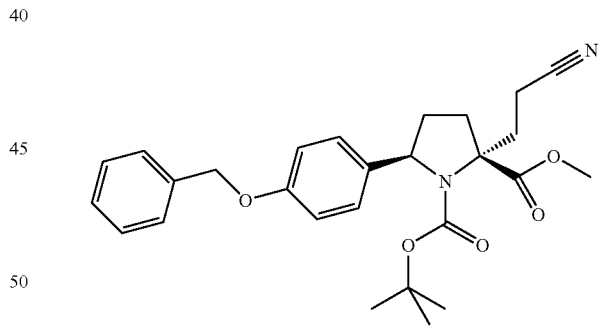

To a solution of 1-(1,1-dimethylethyl) 2-methyl (2S,5R)-5-{4-[(phenylmethyl)oxy]phenyl}-1,2-pyrrolidinedicarboxylate (D6, 200 mg, 0.49 mmol) in dry THF (2 mL) at −78° C. was added LiHMDS (0.53 mL of a 1M solution in THF, 0.53 mmol). The mixture was allowed to warm to −30° C. and stirred for 30 min at this temperature. Then the yellow slurry was cooled to −78° C. and bromopropionitrile (0.24 mL, 2.92 mmol) was added. The reaction mixture was left under stirring for 2 h and then quenched with a saturated ammonium chloride solution. The aqueous layer was extracted with ethyl acetate, dried ($Na_2SO_4$), filtered and evaporated. The crude material was purified by chromatography on silica gel using cyclohexane/ethyl acetate (9:1) affording the title compound (107 mg, 52%).

Description 50: (5S)-2-(4-Hydroxyphenyl)-1,7-diazaspiro[4.5]decan-6-one (D50)

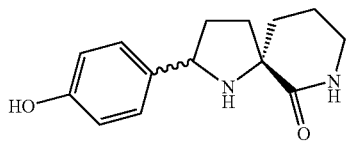

To a solution of 1-(1,1-dimethylethyl) 2-methyl (2R,5R)-2-(2-cyanoethyl)-5-{4-[(phenylmethyl)oxy]phenyl}-1,2-pyrrolidinedicarboxylate (D49, 215 mg, 0.46 mmol) in methanol (20 mL) was added Raney Nickel (slurry in water, 1 spatula) and the mixture was stirred under a hydrogen atmosphere (6 atm) for 4.5 hours. The catalyst was filtered off, the solvent removed under reduced pressure, and the residue treated with toluene (3×20 mL) and dried under vacuum. The crude oil obtained was dissolved in dichloromethane and the resulting solution cooled to 0° C. and TFA (0.2 mL) was added dropwise. After 1 h at room temperature the solvent was removed under vacuum and the residue purified by SCX column and by chromatography on silica gel using dichloromethane/methanol (95:5) to afford the title compound (22 mg, 19%) as a 66/33 mixture of epimers at the benzylic position. $R_t$ (HPLC) 2.16 min; MS: (ES/+) m/z: 247 [MH$^+$]; C14H18N2O2 requires 246.

Description 51: 1,1-Dimethylethyl (5S)-2-(4-hydroxyphenyl)-6-oxo-1,7-diazaspiro[4.5]decane-1-carboxylate (D51)

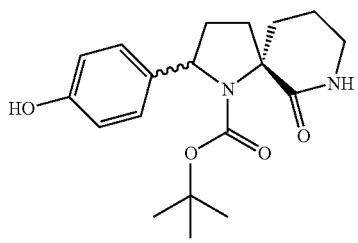

To a solution of (5S)-2-(4-hydroxyphenyl)-1,7-diazaspiro[4.5]decan-6-one (D50, 21 mg, 0.85 mmol) in THF (1 mL), 5% NaHCO$_3$ aqueous solution (1 mL) and t-butanol (1 mL) was added Boc$_2$O (372 mg, 1.70 mmol) and the mixture was stirred at room temperature for 24 hours. Extraction with ethyl acetate, followed by solvent removal gave a crude oil that was purified by chromatography on silica gel using cyclohexane/ethyl acetate (100:0, 95:5, 90:10, 80:20, 50:50: 0:100) to afford the title compound (20 mg, 68%) as a 80/20 mixture of epimers at the benzylic position. $R_t$ (HPLC) 3.69 min (minor epimers) and 4.14 min (major epimers); LC-MS: (ES/+) $R_t$ 5.23 min m/z: 693 [dimerH$^+$] minor isomer; $R_t$ 5.97 min m/z: 693 [dimerH$^+$] major isomer.

Description 52: 1,1-Dimethylethyl (2R,5S)-2-(4-{[(2-fluorophenyl)methyl]oxy}phenyl)-6-oxo-1,7-diazaspiro[4.5]decane-1-carboxylate (D52)

Description 53: 1,1-Dimethylethyl (2S,5S)-2-(4-{[(2-fluorophenyl)methyl]oxy}phenyl)-6-oxo-1,7-diazaspiro[4.5]decane-1-carboxylate (D53)

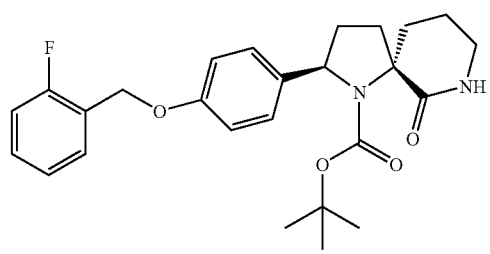

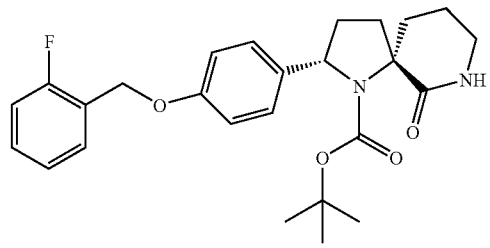

The title compounds were prepared (D52: 20 mg, 76%; D53: 3 mg, 11%) using a similar procedure to that set out earlier in Description 11 starting from 1,1-dimethylethyl (5S)-2-(4-hydroxyphenyl)-6-oxo-1,7-diazaspiro[4.5]decane-1-carboxylate (D51) and 2-fluorobenzyl bromide. D52: $R_t$ (HPLC) 5.92 min; MS: (ES/+) 909 [dimerH$^+$]. D53: $R_t$ (HPLC) 5.73 min; MS: (ES/+) 909 [dimerH$^+$].

Description 54: 4-Bromo-1-{[(2-fluorophenyl)methyl]oxy}-2-(methyloxy)benzene (D54)

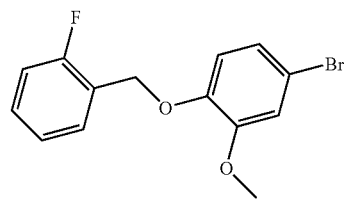

A suspension of 4-bromo-2-(methyloxy)phenol (3.0 g, 14.78 mmol), potassium carbonate (2.99 g, 22.17 mmol) and 2-fluorobenzylbromide (1.78 ml, 14.78 mmol) in acetonitrile (20 ml) was stirred at room temperature overnight. Diethylether was added. The organic phase was then washed with water and 1M NaOH, dried (Na$_2$SO$_4$), filtered and evaporated to afford the title compound (4.388 g, quant.). Rt (HPLC): 6.25 min; 1H-NMR (400 MHz, DMSO-d6) δ(ppm): 7.5 (m, 1H), 7.4 (m, 1H), 7.2 (m, 2H), 7.1 (s, 1H), 7.0 (m, 2H), 5.1 (s, 2H), 3.7 (s, 3H).

Description 55: Methyl (2S)-2-({[(1,1-dimethylethyl)oxy]carbonyl}amino)-5-[4-{[(2-fluorophenyl)methyl]oxy}-3-(methyloxy)phenyl]-5-oxopentanoate (D55)

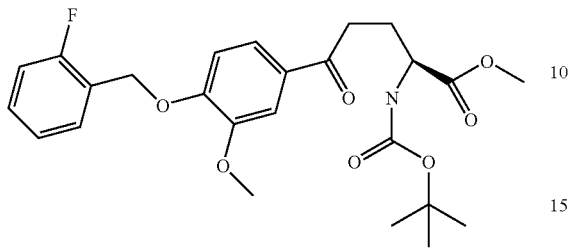

1,2-Dibromoethane (106 μL, 232 mg, 1.233 mmol) was added to a suspension of magnesium (300 mg, 12.33 mmol) in dry THF (3 mL). Then a solution of 4-bromo-1-{[(2-fluorophenyl)methyl]oxy}-2-(methyloxy)benzene (D54, 2.40 g, 8.22 mmol) in dry THF (17 ml) was added dropwise. The mixture was heated under reflux for 1.5 h. The Grignard formation was followed via HPLC (Rt(HPLC, 1-fluoro-2-{[(2-(methyloxy)phenyl]oxy}methyl)benzene): 5.59 min, $R_t$ (HPLC, D54): 6.24 min). When the reaction stopped, additional 1,2-dibromoethane (0.1 eq) was added. After Grignard formation was complete, the mixture was added dropwise to a solution of 1-(1,1-dimethylethyl) 2-methyl (2S)-5-oxo-1,2-pyrrolidinedicarboxylate (D1, 1 g, 4.11 mmol) in dry THF (20 ml) at −65° C. Stirring at −65° C. was continued for 3.5 h. Then isopropanol and diethylether were added, the organic layer was washed with aqueous ammonium chloride solution, dried (Na2SO4) and evaporated. The residue was purified with flash chromatography using a cyclohexanes/ethyl acetate (40% to 100%) gradient to afford the title compound (900 mg, 46%). MS: (ES/+) m/z: 376 [M-BOC+], C25H30FNO7 requires 475; UPLC: 0.84 min, m/z: 476 [MH+], $^1$H NMR (400 MHz, DMSO-d6) δ(ppm): 7.6 (m, 2H), 7.4 (m, 2H), 7.3-7.2 (m, 4H), 5.2 (s, 2H), 4.1 (m, 1H), 3.8 (s, 3H), 3.6 (s, 3H), 3.2-3.0 (m, 2H), 2.1-2.0 (m, 1H), 1.9 (m, 1H), 1.4 (s, 9H).

Description 56: Methyl (2S)-5-[4-{[(2-fluorophenyl)methyl]oxy}-3-(methyloxy)phenyl]-3,4-dihydro-2H-pyrrole-2-carboxylate (D56)

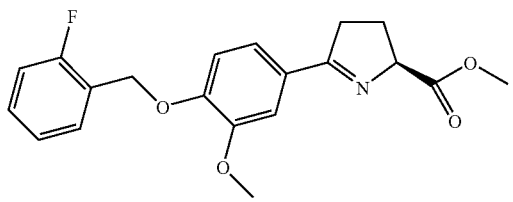

The title compound was synthesized following a similar procedure as set out earlier in Description 32 starting from methyl (2S)-2-({[(1,1-dimethylethyl)oxy]carbonyl}amino)-5-[4-{[(2-fluorophenyl)methyl]oxy}-3-methyloxy)phenyl]-5-oxopentanoate (D55, 900 mg, 1.892 mmol). The crude material (1.6 g) was used without further purification in the next step. UPLC: Rt=0.60 min, MS: (ES/+) 358 m/z: [MH+], C20H20FNO4 requires 357.

Description 57: Methyl (5R)-5-[4-{[(2-fluorophenyl)methyl]oxy}-3-(methyloxy)phenyl]-L-prolinate (D57)

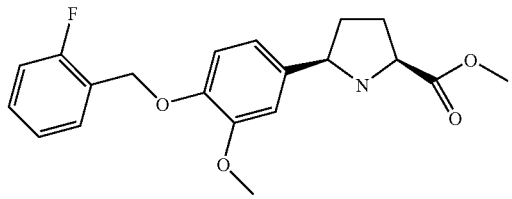

A suspension of ethyl (2R)-5-{4-[(phenylmethyl)oxy]phenyl}-3,4-dihydro-2H-pyrrole-2-carboxylate (D56, 1.6 g) and PVC Degussa type F101 RAW (5% of Pt on C, moisture content ca 50%, 80 mg) in ethyl acetate (10 ml) was stirred for 2 h under hydrogen atmosphere (1 atm). The solution was filtrated over celite, evaporated and purified using a SCX cartridge to afford the title compound (605 mg). UPLC: Rt=0.56 min, MS: (ES/+) m/z: 360 [MH+], C20H22FNO4 requires 359; 1H NMR (400 MHz, DMSO-d6) δ(ppm): 7.5 (m, 1H), 7.4 (m, 1H), 7.2 (m, 2H), 7.1 (s, 1H), 7.0 (m, 1H), 6.9 (m, 1H), 5.1 (s, 2H), 4.1 (m, 1H), 3.8 (m, 1H), 3.7 (s, 3H), 3.6 (s, 3H), 3.0 (bs, 1H), 2.1 (m, 2H), 1.9 (m, 1H), 1.5 (m, 1H).

Description 58: 1-(1,1-Dimethylethyl) 2-methyl (2S, 5R)-5-[4-{[(2-fluorophenyl)methyl]oxy}-3-(methyloxy)phenyl]-1,2-pyrrolidinedicarboxylate (D58)

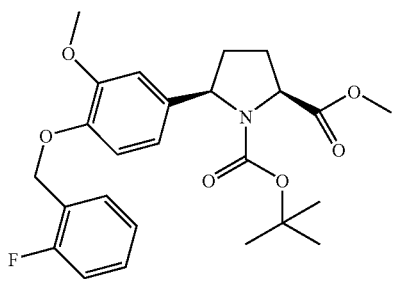

The title compound (0.58 g, 89%) was synthesized following a similar procedure as set out earlier in Description 6 using methyl (5R)-5-[4-{[(2-fluorophenyl)methyl]oxy}-3-(methyloxy)phenyl]-L-prolinate (D57, 0.51 g, 1.42 mmol). $R_t$ (HPLC): 6.35 min; MS: (ES/+) m/z: 482 [M+Na] C25H30FNO6 requires 459; 1H NMR (400 MHz, CDCl3) δ (ppm): 7.51-7.60 (m, 1H), 7.33-7.50 (m, 1H), 7.25-7.32 (m, 1H), 7.11-7.18 (m, 1H), 7.03-7.11 (m, 1H), 6.83-6.99 (m, 2H), 5.21 and 5.23 (s, s, 2H), 4.92-5.02 and 4.67-4.77 (m, m, 1H), 4.42-4.52 and 4.30-4.40 (m, m, 1H), 3.94 (s, 3H), 3.81 (s, 3H), 2.24-2.36 (m, 1H), 2.14-2.24 (m, 1H), 2.00-2.12 (m, 1H), 1.85-2.00 (m, 1H), 1.42 and 1.16 (s, s, 9H).

Description 59: 1-(1,1-Dimethylethyl) 2-methyl (2S, 5R)-5-[4-{[(2-fluorophenyl)methyl]oxy}-3-(methyloxy)phenyl]-2-methyl-1,2-pyrrolidinedicarboxylate: (D59)

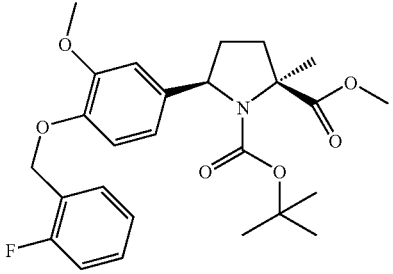

The title compound (0.16 g, 68%) was synthesized following a similar procedure as set out earlier in Description 7 using 1-(1,1-dimethylethyl) 2-methyl (2S,5R)-5-[4-{[(2-fluorophenyl)methyl]oxy}-3-(methyloxy)phenyl]-1,2-pyrrolidinedicarboxylate (D58, 0.23 g, 0.5 mmol).; $R_t$ (HPLC): 6.58 min; MS: (ES/+) m/z: 496 [M+Na] C26H32FNO6 requires 473.

Description 60: (5R)-1-{[(1,1-Dimethylethyl)oxy]carbonyl}-5-[4-{[(2-fluorophenyl)methyl]oxy}-3-(methyloxy)phenyl]-2-methyl-L-proline (D60)

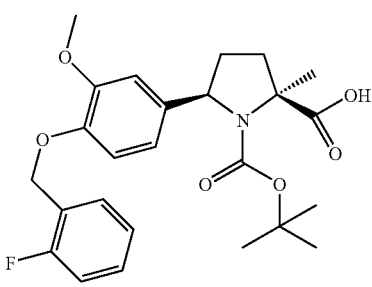

To a solution of 1-(1,1-dimethylethyl) 2-methyl (2S,5R)-5-[4-{[(2-fluorophenyl)methyl]oxy}-3-(methyloxy)phenyl]-2-methyl-1,2-pyrrolidinedicarboxylate (D59, 160 mg, 0.34 mmol) in MeOH (1 ml) was added a solution of LiOH.H2O (29 mg, 0.68 mmol) in H2O (0.5 ml) and the mixture was heated in a microwave synthesizer for 70 min at 100° C. After evaporation of methanol, the aqueous phase was acidified to pH 3.5/4 with a solution of citric acid and extracted with ethyl acetate. The organic layer was dried (Na2SO4), filtered and evaporated affording the title compound (white solid, 150 mg, 97%); $R_t$ (HPLC): 5.89 min. MS: (ES/−) m/z: 482 [M+Na] C25H30FNO6 requires 459.

Description 61: 1,1-Dimethylethyl (2S,5R)-2-(aminocarbonyl)-5-[4-{[(2-fluorophenyl)methyl]oxy}-3-(methyloxy)phenyl]-2-methyl-1-pyrrolidinecarboxylate (D61)

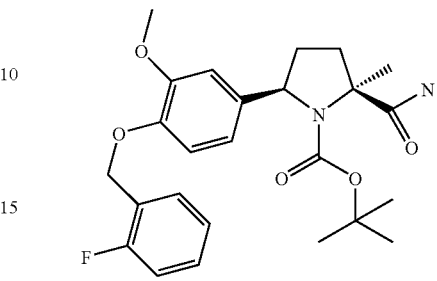

A solution of (5R)-1-{[(1,1-dimethylethyl)oxy]carbonyl}-5-[4-{[(2-fluorophenyl)methyl]oxy}-3-(methyloxy)phenyl]-2-methyl-L-proline (D60, 150 mg, 0.33 mmol), diisopropylethyl amine (0.115 ml, 0.66 mmol) and TBTU (116 mg, 0.36 mmol) in dry DMF (5 ml) was stirred for 15 min at room temperature. HMDS (0.106 ml, 0.5 mmol) was added and stirring was continued at room temperature for 2 h. The mixture was cooled to 0° C. and saturated aqueous NaHCO3 solution was added and the resulting suspension was stirred for 30 min. The mixture was extracted with ethyl acetate and washed three times with ice cold brine. The organic layer was dried (Na2SO4), filtered and evaporated. The residue was purified by chromatography on silica gel using cyclohexane and ethyl acetate (8:2 to 7:3) to afford the title compound (110 mg, 73%); $R_t$ (HPLC): 5.68 min; MS: (ES/+) m/z: 481 [M+Na] C25H31FN2O5 requires 458.

Description 62: 1-(1,1-Dimethylethyl) 2-methyl (2R, 5R)-5-[4-{[(2-fluorophenyl)methyl]oxy}-3-(methyloxy)phenyl]-2-(hydroxymethyl)-1,2-pyrrolidinedicarboxylate (D62)

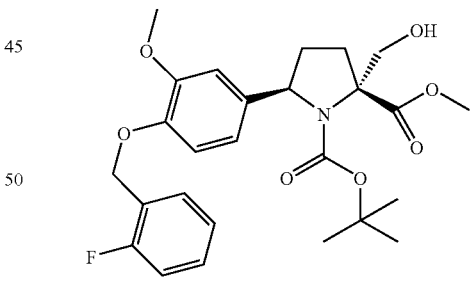

To a solution of 1-(1,1-dimethylethyl) 2-methyl (2S,5R)-5-[4-{[(2-fluorophenyl)methyl]oxy}-3-(methyloxy)phenyl]-1,2-pyrrolidinedicarboxylate (D58, 0.35 g, 0.76 mmol) in dry THF (6 ml) at −78° C. was added dropwise LiHMDS (0.80 ml, 0.80 mmol, 1M solution in THF). The mixture was allowed to warm to −40° C. and was stirred for 40 min at that temperature. Then the mixture was again cooled to −78° C. and ethyl formate (1.23 ml, 15.2 mmol) was added. The mixture was left stirring for another 8 h at the same temperature. The reaction was quenched with brine, diluted with water and extracted with ethyl acetate. The organic layer was dried (Na2SO4), filtered and evaporated. The crude material was dissolved in MeOH (5 ml) at 0° C. and NaBH$_4$ (30 mg, 0.79 mmol) was added. The mixture was stirred for 1 h at the same temperature. The reaction was quenched with a 5% solution of aqueous NaHCO$_3$, diluted with water and extracted with ethyl acetate. The organic layer was dried (Na$_2$SO$_4$), filtered and evaporated and the residue was purified by chromatography on silica gel using cyclohexane and ethyl acetate (9:1 to 75:25) to afford the title compound as a colourless oil (170 mg, 46%); R$_t$ (HPLC): 5.78 min; MS: (ES/+) m/z: 512 [M+Na] C26H32FNO7 requires 489.

Description 63: 1-(1,1-Dimethylethyl) 2-methyl (2R, 5R)-5-[4-{[(2-fluorophenyl)methyl]oxy}-3-(methyloxy)phenyl]-2-[(methyloxy)methyl]-1,2-pyrrolidinedicarboxylate (D63)

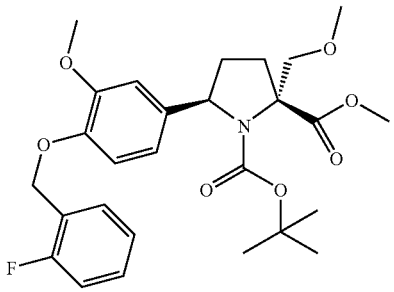

To a solution of 1-(1,1-dimethylethyl) 2-methyl (2R,5R)-5-[4-{[(2-fluorophenyl)methyl]oxy}-3-(methyloxy)phenyl]-2-(hydroxymethyl)-1,2-pyrrolidinedicarboxylate (D62, 170 mg, 0.35 mmol) and methyl iodide (44 µl, 0.70 mmol) in dry DMF (2 ml) at 0° C. was added NaH (60% dispersion in mineral oil) (21 mg, 0.52 mmol) and the mixture was stirred for 1.5 h from 0° C. to r.t. The reaction was quenched with brine and extracted with ethyl acetate. The organic layer was washed three times with ice cold brine, dried (Na$_2$SO$_4$) and evaporated and the residue was purified by chromatography on silica gel using cyclohexane/ethyl acetate (1:0 to 85:15) to afford the title compound as a colourless oil (150 mg, 86%); R$_t$ (HPLC): 6.62 min; MS: (ES/+) m/z: 526 [M+Na] C27H34FNO7 requires 503.

Description 64: (5R)-1-{[(1,1-dimethylethyl)oxy]carbonyl}-5-[4-{[(2-fluorophenyl)methyl]oxy}-3-(methyloxy)phenyl]-2-[(methyloxy)methyl]-L-proline (D64)

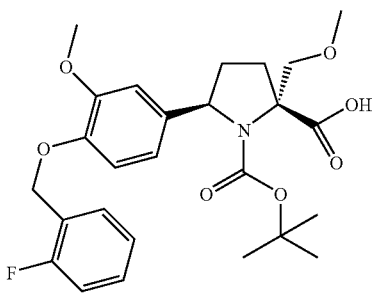

The title compound (white solid, 140 mg, 97%) was prepared by a similar procedure to that set out earlier in Description 60 using 1-(1,1-dimethylethyl) 2-methyl (2R,5R)-5-[4-{[(2-fluorophenyl)methyl]oxy}-3-(methyloxy)phenyl]-2-[(methyloxy)methyl]-1,2-pyrrolidinedicarboxylate (D63, 150 mg, 0.30 mmol). R$_t$ (HPLC): 5.96 min. MS: (ES/+) m/z: 512 [M+Na] C26H32FNO7 requires 489.

Description 65: 1,1-Dimethylethyl (2R,5R)-2-(aminocarbonyl)-5-[4-{[(2-fluorophenyl)methyl]oxy}-3-(methyloxy)phenyl]-2-[(methyloxy)methyl]-1-pyrrolidinecarboxylate (D65)

The title compound (70 mg, 50%) was prepared by a similar procedure to that set out earlier in Description 61 using (5R)-1-{[(1,1-dimethylethyl)oxy]carbonyl}-5-[4-{[(2-fluorophenyl)methyl]oxy}-3-(methyloxy)phenyl]-2-[(methyloxy)methyl]-L-proline (D64, 140 mg, 0.29 mmol). R$_t$ (HPLC): 5.85 min; MS: (ES/+) m/z: 389 [MH-Boc] C26H33FN2O6 requires 488.

Description 66: 1-(1,1-Dimethylethyl) 2-methyl (2R, 5R)-5-(4-{[(2-fluorophenyl)methyl]oxy}phenyl)-2-(hydroxymethyl)-1,2-pyrrolidinedicarboxylate: (D66)

The title compound (930 mg) was prepared by a similar procedure to that set out earlier in Description 62 using 1-(1,1-dimethylethyl) 2-methyl (2S,5R)-5-(4-{[(2-fluorophenyl)methyl]oxy}phenyl)-1,2-pyrrolidinedicarboxylate (D34, 0.80 g, 1.86 mmol), prepared with analogous procedure to that described hereinabove. R$_t$ (HPLC): 6.05 min; MS: (ES/+) m/z: 482 [M+Na] C25H30FNO6 requires 459.

Description 67: 1-(1,1-Dimethylethyl) 2-methyl (2R, 5R)-5-(4-{[(2-fluorophenyl)methyl]oxy}phenyl)-2-[(methyloxy)methyl]-1,2-pyrrolidinedicarboxylate (D67

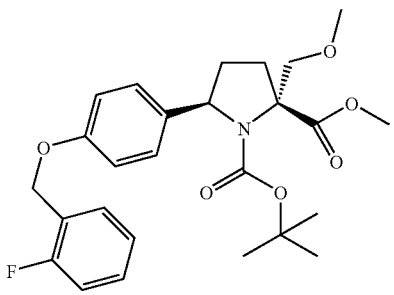

To a solution of 1-(1,1-dimethylethyl) 2-methyl (2R,5R)-5-(4-{[(2-fluorophenyl)methyl]oxy}phenyl)-2-(hydroxymethyl)-1,2-pyrrolidinedicarboxylate (D66, 480 mg, 1.04 mmol) and methyl iodide (130 μl, 2 mmol) in dry DMF (5 ml) at 0° C. was added sodium hydride (60 mg, 1.5 mmol, 60% dispersion in mineral oil) and the mixture was stirred for 1.5 h from 0° C. to r.t. A second batch of 1-(1,1-dimethylethyl) 2-methyl (2R,5R)-5-(4-{[(2-fluorophenyl)methyl]oxy}phenyl)-2-(hydroxymethyl)-1,2-pyrrolidinedicarboxylate (D62, 46 mg, 0.1 mmol) was dissolved in dry DMF (0.5 ml) and methyl iodide was added. The mixture was cooled at 0° C. and sodium hydride (6 mg, 0.15 mmol, 60% dispersion in mineral oil) was added and the mixture was stirred for 1.5 h from 0° C. to r.t. The reactions were quenched with brine/ice and the two mixtures were combined and extracted with ethyl acetate. The organic layer was washed three times with ice cold brine, dried ($Na_2SO_4$) and evaporated to afford the title compound as a colourless oil (540 mg); $R_t$ (HPLC): 6.89 min; MS: (ES/+) m/z: 496 [M+Na] C26H32FNO6 requires 473; $^1$H NMR (400 MHz, CDCl$_3$) δ(ppm): 7.48-7.59 (m, 1H); 7.42-7.48 (m, 2H); 7.28-7.36 (m, 1H); 7.13-7.21 (m, 1H); 7.03-7.13 (m, 1H); 6.89-7.00 (m, 2H); 5.13 and 5.16 (s, s, 2H); 4.94-5.06 and 4.74-4.83 (m, m, 1H); 4.09-4.19 (m, 1H); 3.78-3.96 (m, 1H); 3.83 (s, 3H); 3.41 (s, 3H); 2.44-2.70 (m, 1H); 2.17-2.36 (m, 2H); 1.69-1.87 (m, 1H); 1.11 and 1.40 (s, s, 9H).

Description 68: (5R)-1-{[(1,1-Dimethylethyl)oxy]carbonyl}-5-(4-{[(2-fluorophenyl)methyl]oxy}phenyl)-2-[(methyloxy)methyl]-L-proline (D68)

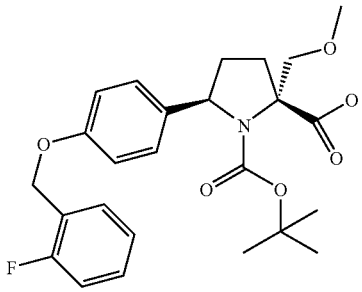

The title compound (white solid, 510 mg, 97%) was prepared by a similar procedure to that set out earlier in Description 60 using 1-(1,1-dimethylethyl) 2-methyl (2R,5R)-5-(4-{[(2-fluorophenyl)methyl]oxy}phenyl)-2-[(methyloxy)methyl]-1,2-pyrrolidinedicarboxylate (D67, 540 mg, 1.14 mmol). $R_t$ (HPLC): 6.17 min. MS: (ES/−) m/z: 482 [M+Na] C25H30FNO6 requires 459; $^1$H NMR (400 MHz, DMSO-d$_6$) δ(ppm): 12.57-12.98 (br.s, 1H); 7.50-7.61 (m, 1H); 7.34-7.49 (m, 3H); 7.16-7.30 (m, 2H); 6.88-7.01 (m, 2H); 5.11 and 5.13 (s, s, 2H); 4.63-4.72 and 4.78-4.86 (m, m, 1H); 3.92 and 4.03 (d, d, 1H); 3.65 and 3.72 (d, d, 1H); 3.29 (s, 3H); 2.35-2.46 and 2.53-2.60 (m, m, 1H); 2.05-2.24 (m, 2H); 1.49-1.71 (m, 1H); 1.02 and 1.33 (s, s, 9H).

Description 69: 1,1-Dimethylethyl (2R,5R)-2-(aminocarbonyl)-5-(4-{[(2-fluorophenyl)methyl]oxy}phenyl)-2-[(methyloxy)methyl]-1-pyrrolidinecarboxylate: (D69)

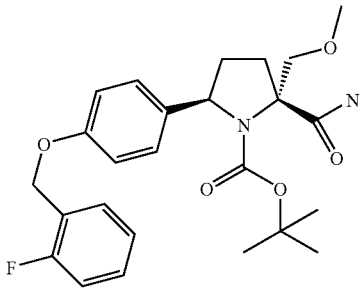

The title compound (400 mg, 78%) was prepared by a similar procedure to that set out earlier in Description 61 using (5R)-1-{[(1,1-dimethylethyl)oxy]carbonyl}-5-(4-{[(2-fluorophenyl)methyl]oxy}phenyl)-2-[(methyloxy)methyl]-L-proline (D68, 510 mg, 1.11 mmol). $R_t$ (HPLC): 6.07 min; MS: (ES/+) m/z: 481 [M+Na] C25H31FN2O5 requires 458.

Description 70: 2-Methyl 1-(phenylmethyl)(2S,5R)-5-(4-{[(2-fluorophenyl)methyl]oxy}phenyl)-1,2-pyrrolidinedicarboxylate (D70)

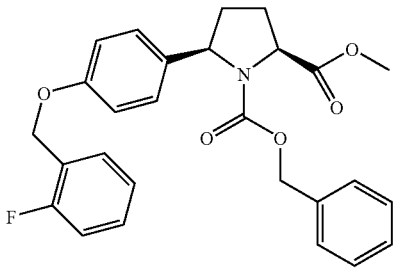

To a solution of methyl (5R)-5-(4-{[(2-fluorophenyl)methyl]oxy}phenyl)-L-prolinate (D33, 2.5 g, 7.6 mmol), and diisopropylethyl amine (2 ml, 11.4 mmol) in dry DCM (25 ml) at 0° C. was added dropwise benzyl chloroformate (1.3 ml, 9.1 mmol) and the mixture was stirred for 1 h from 0° C. to r.t. The mixture was washed with a 20% solution of citric acid and after with brine. The organic layer was dried ($Na_2SO_4$), filtered and evaporated. The residue was purified by chromatography on silica gel using cyclohexane and ethyl acetate (85:15) to afford the title compound (3.4 g, 97%) as a white solid.; $R_t$ (HPLC) 6.56 min; $^1$H NMR (400 MHz, CDCl$_3$) δ (ppm): 7.42-7.60 (m, 3H); 7.29-7.42 (m, 3H); 7.15-7.25 (m, 3H); 7.06-7.15 (m, 1H); 6.86-7.03 (m, 3H); 5.10 and 5.15 (s, s, 2H); 4.84-5.04 (m, 3H); 4.48 and 4.55 (m, m, 1H); 3.69 and 3.84 (s, s, 3H); 2.27-2.39 (m, 1H); 2.16-2.27 (m, 1H); 2.03-2.16 (m, 1H); 1.91-2.03 (m, 1H).

Description 71: 2-Methyl 1-(phenylmethyl)(2R,5R)-5-(4-{[(2-fluorophenyl)methyl]oxy}phenyl)-2-(hydroxymethyl)-1,2-pyrrolidinedicarboxylate: (D71)

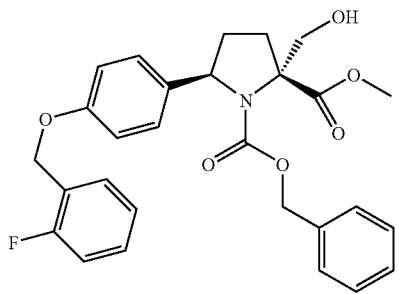

The title compound (1.19 g, 46%) was prepared with a similar procedure to that set out earlier in Description 62 using 2-methyl 1-(phenylmethyl)(2S,5R)-5-(4-({[(2-fluorophenyl)methyl]oxy}phenyl)-1,2-pyrrolidinedicarboxylate (D70, 2.0 g, 4.31 mmol). $R_t$ (HPLC): 6.06 min; MS: (ES/+) m/z: 494 [MH]+ C28H28FNO6 requires 493.

Description 72: 2-Methyl 1-(phenylmethyl)(2R,5R)-2-({[(1,1-dimethylethyl)(dimethyl)silyl]oxy}methyl)-5-(4-{[(2-fluorophenyl)methyl]oxy}phenyl)-1,2-pyrrolidinedicarboxylate (D72)

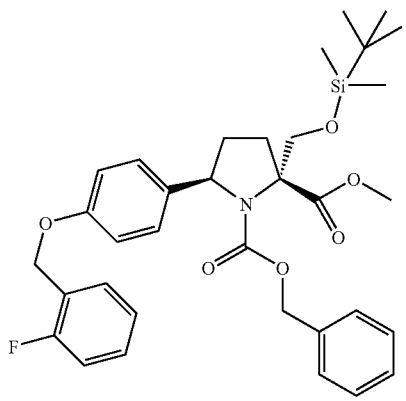

To a solution of 2-methyl 1-(phenylmethyl)(2R,5R)-5-(4-{[(2-fluorophenyl)methyl]oxy}phenyl)-2-(hydroxymethyl)-1,2-pyrrolidinedicarboxylate (D71, 200 mg, 0.4 mmol) and imidazole (60 mg, 0.88 mmol) in dry DMF (1 ml) was added tert-butyl dimethylsilyl chloride and the mixture was stirred for 36 hours. The reaction was quenched with brine, diluted with water and extracted with ethyl acetate. The organic layer was washed with ice cold brine, dried (Na$_2$SO$_4$), filtered and evaporated. The residue was purified by chromatography on silica gel using cyclohexane and ethyl acetate (1:0 to 9:1) to afford the title compound as a colourless oil (180 mg, 74%);

$R_t$ (HPLC): 8.50 min; MS: (ES/+) m/z: 608 [MH]+ C34H42FNO6Si requires 607.

Description 73: (5R)-2-({[(1,1-Dimethylethyl)(dimethyl)silyl]oxy}methyl)-5-(4-{[(2-fluorophenyl)methyl]oxy}phenyl)-1-{[(phenylmethyl)oxy]carbonyl}-L-proline (D73)

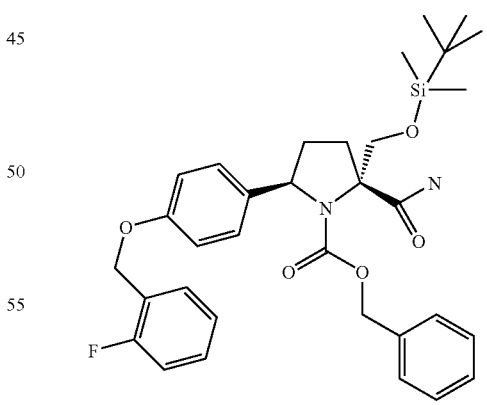

The title compound (white solid, 120 mg, 67%) was prepared by a similar procedure to that set out earlier in Description 60 using 2-methyl 1-(phenylmethyl)(2R,5R)-2-({[(1,1-dimethylethyl)(dimethyl)silyl]oxy}methyl)-5-(4-{[(2-fluorophenyl)methyl]oxy}phenyl)-1,2-pyrrolidinedicarboxylate (D72, 180 mg, 0.3 mmol). $R_t$ (HPLC): 7.98 min. MS: (ES/+) m/z: 594 [MH]+ C33H40FNO6Si requires 593.

Description 74: Phenylmethyl (2R,5R)-2-(aminocarbonyl)-2-({[(1,1-dimethylethyl)(dimethyl)silyl]oxy}methyl)-5-{4-[(2-fluorophenyl)methyl]oxy}phenyl)-1-pyrrolidinecarboxylate (D74)

The title compound (85 mg, 70%) was prepared by a similar procedure to that set out earlier in description 61 using (5R)-2-({[(1,1-dimethylethyl)(dimethyl)silyl]oxy}methyl)-5-(4-{[(2-fluorophenyl)methyl]oxy}phenyl)-1-{[(phenylmethyl)oxy]carbonyl}-L-proline (D73, 120 mg, 0.20 mmol). $R_t$ (HPLC): 7.82 min; MS: (ES/+) m/z: 593 [MH]+ C33H41FN2O5Si requires 592.

Description 75: (5R)-2-({[(1,1-Dimethylethyl)(dimethyl)silyl]oxy}methyl)-5-(4-{[(2 fluorophenyl)methyl]oxy}phenyl)-L-prolamide (D75)

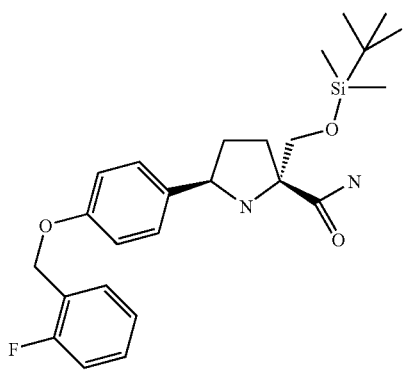

To a solution of phenylmethyl (2R,5R)-2-(aminocarbonyl)-2-({[(1,1-dimethylethyl)(dimethyl)silyl]oxy}methyl)-5-(4-{[(2-fluorophenyl)methyl]oxy}phenyl)-1-pyrrolidinecarboxylate (D74, 85 mg, 0.14 mmol) in methanol (2 ml) was added palladium (10 mg, 10 wt. % dry basis on activated carbon) and the mixture was stirred under hydrogen atmosphere (1 atm) for 30 min. The catalyst was filtered off, the solvent removed under reduced pressure and the crude material purified by chromatography on silica gel using cyclohexane and ethyl acetate (9:1 to 75:25) to afford the title compound (50 mg, 79%) as a colourless oil; $R_t$ (HPLC): 5.00 min; MS: (ES/+) m/z: 459 [MH]+ C25H35FN2O3Si requires 458.

Description 76: 1-(1,1-Dimethylethyl) 2-methyl (2S, 5S)-5-{4-[(phenylmethyl)oxy]phenyl}-1,2-pyrrolidinedicarboxylate (D76)

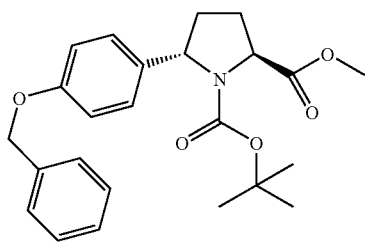

The title compound (1.35 g, 82%) was prepared by a similar procedure to that set out earlier in Description 6 using methyl (5S)-5-{4-[(phenylmethyl)oxy]phenyl}-L-prolinate (D5, 1.24 g, 3.98 mmol. $R_t$ (HPLC): 6.45 min, MS: (ES/+) m/z: 434 [M+Na]C24H29NO5 requires 411; 1H NMR (400 MHz, CDCl3) δ (ppm): 7.21-7.53 (m, 5H); 7.05-7.16 (m, 2H); 6.91-6.98 (m, 2H); 5.00 and 5.16 (d, d, 1H); 5.05 and 5.07 (s, s, 2H); 4.51 and 4.63 (d, d, 1H); 3.77 and 3.78 (s, s, 3H); 2.37-2.53 (m, 1H); 2.22-2.37 (m, 1H); 1.89-2.00 (m, 1H); 1.72-1.85 (m, 1H); 1.22 and 1.42 (s, s, 9H).

Description 77: 1-(1,1-Dimethylethyl) 2-methyl (2S, 5S)-2-(cyanomethyl)-5-{4-[(phenylmethyl)oxy]phenyl}-1,2-pyrrolidinedicarboxylate (D77)

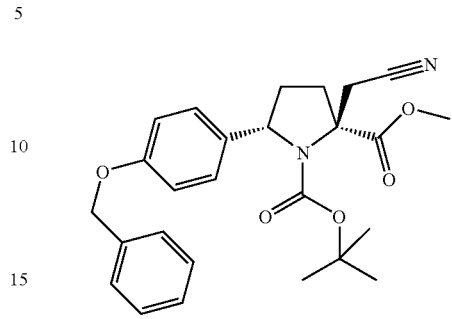

The title compound (0.5 g, 41%) was prepared by a similar procedure to that set out earlier in Description 7 using 1-(1,1-dimethylethyl) 2-methyl (2S,5S)-5-{4-[(phenylmethyl)oxy]phenyl}-1,2-pyrrolidinedicarboxylate (D76, 1.12 g, 2.72 mmol). $R_t$ (HPLC): 6.39 min; MS: (ES/+) m/z: 473 [M+Na] C26H30N2O5 requires 450; 1H NMR (400 MHz, CDCl3) δ(ppm): 7.30-7.49 (m, 7H); 6.91-7.00 (m, 2H); 5.10 (s, 2H); 4.91 and 5.08 (m, m, 1H); 3.88 and 3.90 (s, s, 3H); 3.04-3.59 (m, 2H); 2.55-2.74 (m, 1H); 2.36-2.51 (m, 1H); 2.21-2.36 (m, 1H); 1.90-2.07 (m, 1H); 1.12 and 1.42 (s, s, 9H).

Description 78: 1,1-Dimethylethyl (2S,5S)-2-(4-hydroxyphenyl)-6-oxo-1,7-diazaspiro[4.4]nonane-1-carboxylate (D78)

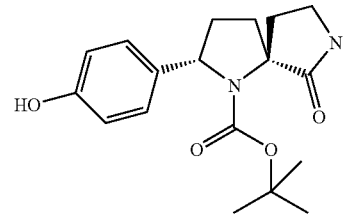

To a solution of 1-(1,1-dimethylethyl) 2-methyl (2S,5S)-2-(cyanomethyl)-5-{4-[(phenylmethyl)oxy]phenyl}-1,2-pyrrolidinedicarboxylate (D77, 500 mg, 1.11 mmol) in methanol (30 ml) was added Raney Nickel (slurry in water, 1 spatula) and the mixture was stirred under a hydrogen atmosphere (6 atm) for 6 hours. The catalyst was filtered off, the solvent removed under reduced pressure, and the solid residue was treated two times with toluene and dried under vacuum. The dry white solid obtained was refluxed in methanol (30 ml) for six hours until cyclization was complete. The solvent was removed under reduced pressure and the crude material purified by chromatography on silica gel using dichloromethane/methanol (1:0 to 92:8) to afford the title compound as a white solid (130 mg, 35%); Rt (HPLC): 3.89 min; Rf (dichloromethane/methanol=9:1): 0.41; MS: (ES/+) m/z: 665 [2M+Na+], 355 [M+Na+]; C18H24N2O4 requires 332; 1H NMR (400 MHz, DMSO-d6) δ(ppm): 9.11 (s, 1H); 7.76 and 7.66 (s, s, 1H); 7.43 (dd, 2H); 6.66 (dd, 2H); 4.81-4.70 (m, 1H); 3.29-3.20 (m, 1H); 3.19-3.09 (m, 1H); 2.47-2.20 (m, 2H); 2.08-1.85 (m, 2H); 1.84-1.74 (m, 1H); 1.68-1.52 (m, 1H); 1.33 and 1.08 (s, s, 9H).

Description 79: 1,1-Dimethylethyl (2S,5S)-2-(4-{[(2-fluorophenyl)methyl]oxy}phenyl)-6-oxo-1,7-diazaspiro[4.4]nonane-1-carboxylate (D79):

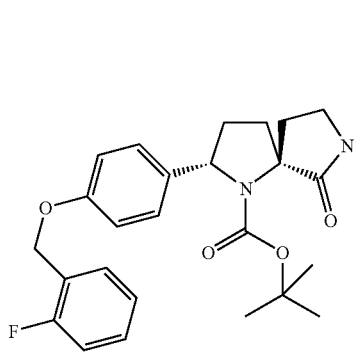

The title compound (130 mg, 76%) was prepared by a similar procedure to that set out earlier in Description 11 using 1,1-dimethylethyl (2S,5S)-2-(4-hydroxyphenyl)-6-oxo-1,7-diazaspiro[4.4]nonane-1-carboxylate (D78, 130 mg, 0.39 mmol). Rf (HPLC): 5.71 min; $R_f$ (cyclohexane/ethyl acetate=3:7): 0.45; MS: (ES/+) m/z: 463 [M+Na+]. C25H29FN2O4 requires 440; 1H NMR (400 MHz, DMSO-d6) δ(ppm): 7.66 and 7.83 (s, s, 1H); 7.50-7.65 (m, 3H); 7.35-7.49 (m, 1H); 7.16-7.32 (m, 2H); 6.86-7.04 (m, 2H); 5.11 and 5.12 (s, s, 2H); 4.79 and 4.84 (m, m, 1H); 3.06-3.28 (m, 2H); 2.18-2.43 (m, 2H); 1.85-2.09 (m, 2H); 1.75-1.85 (m, 1H); 1.51-1.72 (m, 1H); 1.33 and 1.36 (s, s, 9H).

Description D80: Methyl 6-(4-hydroxyphenyl)-2-pyridinecarboxylate (D80)

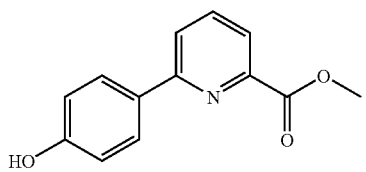

A mixture of methyl 6-bromo-2-pyridinecarboxylate (1.35 g, 6.22 mmol, 1 eq), (4-hydroxyphenyl)boronic acid (0.945 g, 6.85 mmol, 1.1 eq), Pd(PPh3)4 (0.718 g, 0.06 mmoles, 0.01 eq) and K2CO3 (1.7 g, 12.4 mmoles, 2 eq) in dioxane (15 mL) and water (8 mL) was heated at 100° C. for 2 h. Then AcOEt was added and the organic phase was washed with water, dried over Na2SO4, filtered and evaporated to dryness. The crude compound was purified on flash chromatography on 50 g silica gel cartridge using a gradient of cyclohexane/ethyl acetate 10/0 to 7/3 as an eluent. Solvents were removed under reduced pressure to give the title compound as a yellow solid (650 mg, 46%). 1H-NMR (CDCl3, 400 MHz): δ 4.03 (3H, s), 5.28 (1H, s), 6.90-7.03 (2H, m), 7.80-7.98 (2H, m), 8.0-8.06 (3H, m). MS: (ES/+) m/z: 230 (M+H)+. C13H11NO3 requires 229.

Description D81: Methyl 6-(4-{[(2-fluorophenyl)methyl]oxy}phenyl)-2-pyridinecarboxylate (D81)

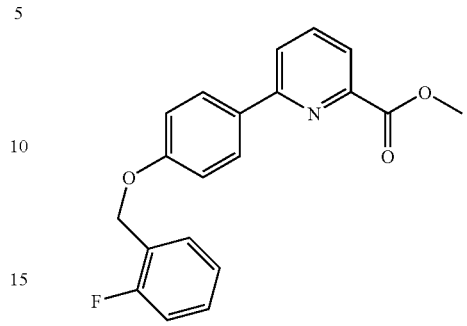

To a solution of methyl 6-(4-hydroxyphenyl)-2-pyridinecarboxylate (D80, 650 mg, 2.84 mmol) in acetone (8 ml) were added K2CO3 (780 mg, 5.67 mmol) and 1-(bromomethyl)-2-fluorobenzene (805 mg, 4.26 mmol). The mixture was stirred at 60° C. under nitrogen atmosphere for 6 h. Solvent was removed under reduced pressure and the residue was dissolved in AcOEt. The organic phase was washed with water, dried over Na2SO4, filtered and evaporated to dryness. The crude compound was purified by flash chromatography on 25 g silica gel cartridge, using a gradient of cyclohexane/ethylacetate 10/0 to 8/2 as eluent, to give the title compound (700 mg, 73%).

LC-MS [Supelcosil ABZ+Plus, 33×4.6 mm, 3 μm, gradient: A: H2O+0.1% HCOOH/B: CH3CN: 0% to 95% B in 3 min., 95% B for 1 min., 95% B to 0% B in 0.1 min., flow rate: 2 mL/min]. $R_t$=2.90 min (100%) (m/z=338 (M+H)+). C20H16FNO3 requires 337.

Description D82: Methyl (2S,6R)-6-(4-{[(2-fluorophenyl)methyl]oxy}phenyl)-2-piperidinecarboxylate, methyl (2R,6S)-6-(4-{[(2-fluorophenyl)methyl]oxy}phenyl)-2-piperidinecarboxylate (D82)

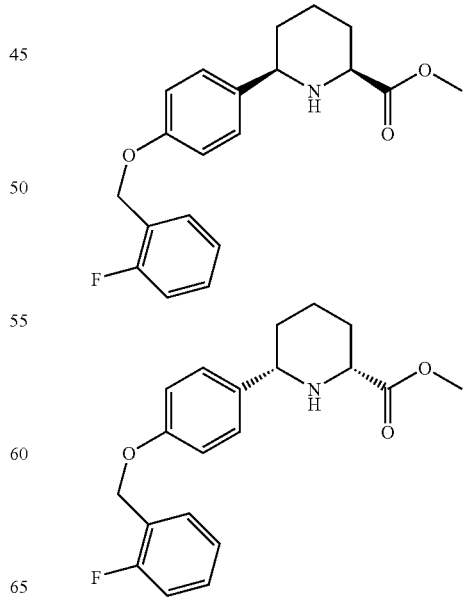

To a solution of methyl 6-(4-{[(2-fluorophenyl)methyl]oxy}phenyl)-2-pyridinecarboxylate (D81, 700 mg, 2.1 mmol, 1 eq) in acetic acid (35 ml) was added PtO$_2$ (200 mg, 30% w/w). The mixture was hydrogenated at 4 atm for 6 h. Solvent was removed under reduced pressure. A solution of NaOH 1M was added, then AcOEt was added and the organic phase obtained was dried over Na$_2$SO$_4$, filtered and evaporated to dryness. The crude compound was purified by flash chromatography on 20 g silica gel cartridge, using a gradient of DCM/MeOH 10/0 to 9.5/0.5 as an eluent, to give the title compound (420 mg, 47%) as a racemate. ES-MS: m/z: 344 (M+H)$^+$. C20H22FNO3 requires 343.

Description D83: 2-Methyl 1-(phenylmethyl)(2S,6R)-6-(4-{[(2-fluorophenyl)methyl]oxy}phenyl)-1,2-piperidinedicarboxylate, 2-methyl 1-(phenylmethyl)(2R,6S)-6-(4-{[(2-fluorophenyl)methyl]oxy}phenyl)-1,2-piperidinedicarboxylate (D83)

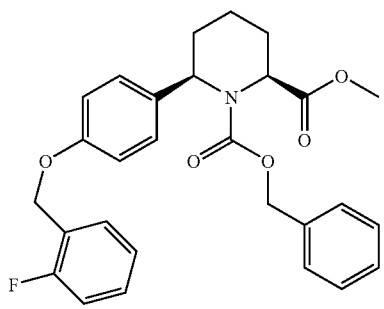

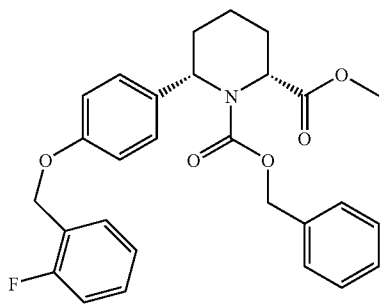

To a solution of racemic methyl (2S,6R)-6-(4-{[(2-fluorophenyl)methyl]oxy}phenyl)-2-piperidinecarboxylate (D82, 420 mg, 1.22 mmol, 1 eq) and DIPEA (320 μL, 1.80 mmol, 1.5 eq) in DCM (9 ml) was added, at 0° C., phenylmethyl chloridocarbonate (213 μL, 1.47 mmol, 1.2 eq). The mixture was allowed to reach RT and was stirred under nitrogen atmosphere for 1 h. The reaction was quenched with water. The organic phase was separated and evaporated to dryness. The resulting crude compound was purified by flash chromatography on 20 g silica gel cartridge, using a gradient of cyclohexanes/ethyl acetate 10/0 to 8/2 as eluent to give the title compound (525 mg, 89%) as a racemate. 1H-NMR (CDCl$_3$, 400 MHz): δ(ppm): 1.60-1.79 (2H, m), 1.80-2.02 (2H, m), 2.04-2.29 (2H, m), 3.22 (3H, s), 4.88 (1H, t), 5.13 (2H, s), 5.21 (2H, s), 5.39 (1H, t), 6.89 (2H, d), 7.08-7.19 (2H, m), 7.24-7.40 (8H, m), 7.47 (1H, t).

Description D84: 2-Methyl 1-(phenylmethyl)(2R,6R)-2-(cyanomethyl)-6-(4-{[(2-fluorophenyl)methyl]oxy}phenyl)-1,2-piperidinedicarboxylate, 2-methyl 1-(phenylmethyl)(2S,6S)-2-(cyanomethyl)-6-(4-{[(2-fluorophenyl)methyl]oxy}phenyl)-1,2-piperidinedicarboxylate (D84):

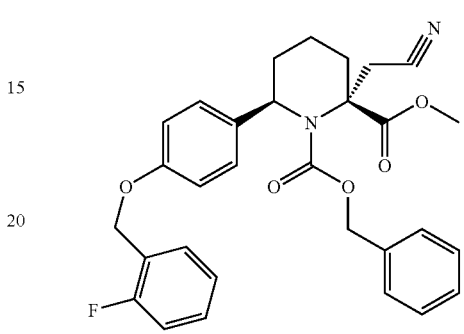

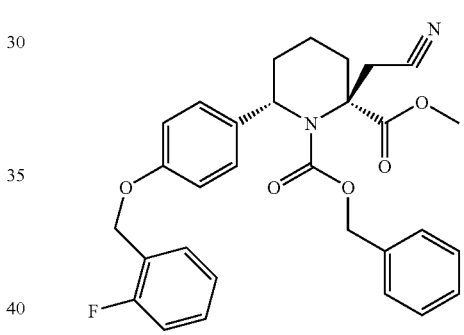

A solution of racemic 2-methyl 1-(phenylmethyl)(2S,6R)-6-(4-{[(2-fluorophenyl)methyl]oxy}phenyl)-1,2-piperidinedicarboxylate (D83, 525 mg, 1.10 mmol, 1.1 eq) in dry THF (6 mL) was cooled to −78° C. and LiHMDS (1.2 ml, 1M in THF) was added dropwise. The reaction mixture was stirred for 30 min at −40° C. under a nitrogen atmosphere. Then the temperature was cooled to −78° C. and a solution of bromoacetonitrile (460 μl, 6.6 mmol, 6 eq) in THF (2 mL) was added. The reaction was stirred at −78° C. under a nitrogen atmosphere for 1 h. The reaction was quenched with a saturated solution of NH$_4$Cl and AcOEt was added. The organic phase was separated, dried over Na$_2$SO$_4$, filtered and evaporated to dryness. The resulting crude compound was purified by flash chromatography on 20 g silica gel cartridge, using a gradient of cyclohexanes/ethyl acetate 10/0 to 7/3 as eluent to give the title compound (524 mg, 92%). 1H-NMR (CDCl$_3$, 400 MHz): δ 1.82 (2H, m), 2.01 (2H, m), 2.20 (1H, m), 2.38 (1H, m), 2.95 (1H, d), 3.52 (1H, d), 3.70 (3H, s), 5.10 (2H, s), 5.13 (2H, s), 5.25 (1H, t), 6.96 (2H, d), 7.11 (2H, t), 7.19 (2H, t), 7.27-7.38 (4H, m), 7.45 (2H, d), 7.55 (1H, t); R$_t$ (HPLC)= 6.65 min.

Description 85: 1-(1,1-Dimethylethyl) 2-methyl (2R, 5R)-2-(cyanomethyl)-5-(4-{[(2-fluorophenyl)methyl]oxy}phenyl)-1,2-pyrrolidinedicarboxylate (D85)

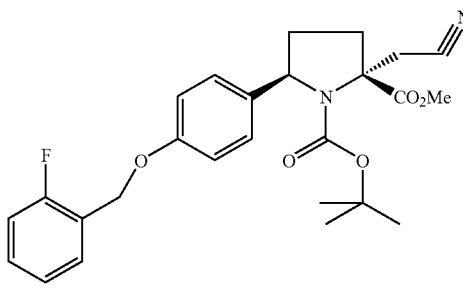

To a solution of 1-(1,1-dimethylethyl) 2-methyl (2S,5R)-5-(4-{[(2-fluorophenyl)methyl]oxy}phenyl)-1,2-pyrrolidinedicarboxylate (D34, 45 g) in dry THF (450 mL) previously cooled to −65° C., was added 1M LiHMDS in THF (115 mL) dropwise. The resulting solution was stirred at −35° C. for 30 minutes. Then the mixture was again cooled to −65° C. and bromoacetonitrile (22 mL) dissolved in dry THF (180 mL) was added. The mixture was left stirring for a further 30 min at the same temperature. The reaction was quenched with saturated ammonium chloride solution (675 mL), THF was evaporated in vacuo and the crude mixture was extracted with EtOAc (2×675 mL). The organic layer was evaporated and the crude material was purified by chromatography on silica gel using cyclohexanes and ethyl acetate (8:2) affording the title compound (51.3 g) as a yellow thick oil.

1H NMR (400 MHz, CDCl$_3$-d) δ(ppm): 7.53 (t, 1H), 7.43 (d, 2H), 7.29-7.37 (m, 1H), 7.17 (t, 1H), 7.07-7.13 (m, 1H), 6.97 (d, 2H), 5.16 (s, 2H), 4.88-4.95 (m, 1H), 3.90 (s, 3H), 3.52 (d, 1H), 3.15 (d, 1H), 2.57-2.70 (m, 1H), 2.38-2.50 (m, 1H), 2.23-2.34 (m, 1H), 1.92-2.06 (m, 1H), 1.44 (s, 9H).

Description 86: 1-(1,1-dimethylethyl) 2-methyl (2R, 5R)-5-(4-{[(2-fluorophenyl)methyl]oxy}phenyl)-2-[2-(methylamino)ethyl]-1,2-pyrrolidinedicarboxylate and 1,1-dimethylethyl (2R,5R)-2-(4-{[(2-fluorophenyl)methyl]oxy}phenyl)-7-methyl-6-oxo-1,7-diazaspiro[4.4]nonane-1-carboxylate (D86)

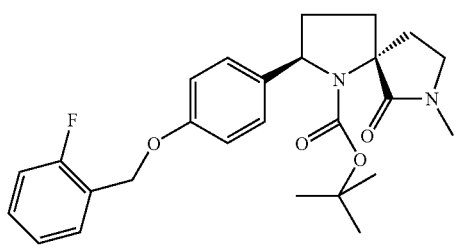

-continued

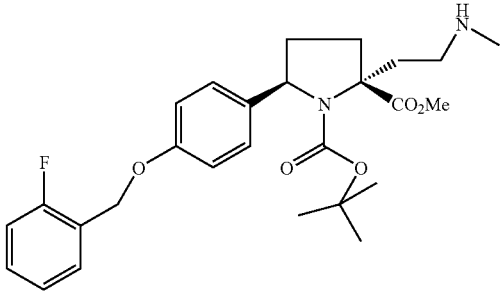

A solution of 1-(1,1-dimethylethyl) 2-methyl (2R,5R)-5-(4-{[(2-fluorophenyl)methyl]oxy}phenyl)-2-(2-oxoethyl)-1,2-pyrrolidinedicarboxylate (D37, 9.5 g) in methanol (38 ml) was cooled to 5-10° C. Methylamine in methanol (12.79 of a 24.7% solution) was added and the mixture stirred at 5-10° C. for 1 hour. Acetic acid (7.6 ml) was added to give a pH of approximately 7, and then the temperature was raised to 20-25° C. Sodium triacetoxyborohydride (6.4 g) was added in portions over 1 hour, then the mixture stirred at 20-25° C. for a further 2 hours. Methanol was distilled off under vacuum, then the mixture treated with ethyl acetate (50 ml) and water (50 ml). The layers were separated and the aqueous layer re-extracted with ethyl acetate (25 ml). The combined ethyl acetate solutions were extracted with 28% citric acid solution (4×50 ml), then the combined aqueous layers were treated with 30% sodium carbonate solution (150 ml) and ethyl acetate to pH 9. The aqueous layer was re-extracted with ethyl acetate (25 ml), then the combined ethyl acetate solution was dried over sodium sulphate and evaporated to give the title compound as a crude (6.6 g) also containing the compound 1,1-dimethylethyl (2R,5R)-2-(4-{[(2-fluorophenyl)methyl]oxy}phenyl)-7-methyl-6-oxo-1,7-diazaspiro[4.4]nonane-1-carboxylate.

MS: (ES/+) m/z: 455 [MH$^+$] (cyclised product)

EXAMPLES

Example 1

(5R)-5-(4-{[(2-Fluorophenyl)methyl]oxy}phenyl)-2-methyl-L-prolinamide hydrochloride (E1)

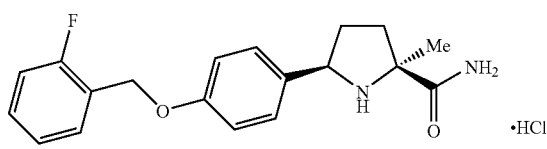

To a solution of 1,1-dimethylethyl (2S,5R)-2-(aminocarbonyl)-5-(4-{[(2-fluorophenyl)methyl]oxy}phenyl)-2-methyl-1-pyrrolidinecarboxylate (D11, 306 mg, 0.69 mmol) in a mixture of ethyl acetate (5 ml) and methanol (0.5 ml) was added AcCl (130 μl, 2.5 eq) at 0° C. The mixture was stirred for 1 hour at room temperature. A further addition of AcCl (130 μl) was made and stirred for 30 min rt. The reaction mixture was kept overnight at −18° C. Then AcCl (another 100 μl) was added at 0° C., stirring for 15 mins, then for 1 hour at rt. The reaction was then complete (as shown by HPLC). The mixture was evaporated to afford the title compound as a white solid (246 mg, 95%); R$_t$ (HPLC) 3.62 min; Chiral HPLC: Column: chiralpak AD-H 5 um, 250×4.6 mm; Mobile phase: A: n-Hexane; B: Ethanol; Gradient: isocratic 30% B; Flow rate: 0.8 ml/min; UV wavelength range: 200400 nm; Analysis time: 20 min; ret. time: 14.3 min; MS: (ES/+) m/z: 329 [MH+]; ¹H NMR (500 MHz, DMSO-d₆) δ (ppm): 9.87 (br. s., 1H), 8.24 (br. s., 1H), 8.12 (s, 1H), 7.89 (s, 1H), 7.56 (t, 1H), 7.39-7.47 (m, 3H), 7.21-7.30 (m, 2H), 7.11 (d, 2H), 5.16 (s, 2H), 4.60-4.76 (m, 1H), 2.42-2.54 (m, 1H), 2.23-2.34 (m, 1H), 1.99-2.11 (m, 1H), 1.84-1.97 (m, 1H), 1.65 (s, 3H).

The following compounds of formula (Ie) were prepared using a similar procedure to that described above for Example 1. For each compound, reference to a starting material (SM) is provided. This is provided merely for assistance to the skilled chemist. The starting material may not necessarily have been prepared from the batch referred to.

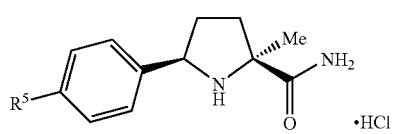

(Ie)

| No. | SM | R⁵ | Characterising data |
|---|---|---|---|
| E2 | D12 | 2-cyanobenzoxy | R_t (HPLC) 3.39 min; MS: (ES/+) 336 m/z: [MH+]. C20H21N3O2 requires; ¹H NMR (500 MHz, DMSO-d6) δ (ppm): 9.89 (br. s, 1H), 8.29 (br. s, 1H), 8.12 (s, 1H), 7.93 (d, 1H), 7.89 (s, 1H), 7.80-7.70 (m, 2H), 7.59 (dt, 1H), 7.46 (d, 2H), 7.12 (d, 2H), 5.27 (s, 2H), 4.78-4.63 (m, 1H), 2.51-2.42 (m, 1H), 2.34-2.23 (m, 1H), 2.11-1.98 (m, 1H), 1.97-1.87 (m, 1H), 1.64 (s, 3H). |
| E3 | D13 | 2-cyanophenoxy | R_t (HPLC) 3.28 min; MS: (ES/+) m/z: 322 [MH+]. C19H19N3O2 requires 321; ¹H NMR (500 MHz, DMSO-d6) δ (ppm) 10.09 (br. s., 1H), 8.35 (br. s., 1H), 8.14 (s, 1H), 7.94 (d, 1H), 7.87 (s, 1H), 7.70 (dt, 1H), 7.57 (d, 2H), 7.33 (t, 1H), 7.21 (d, 2H), 7.00 (d, 1H), 4.72-4.85 (m, 1H), 2.50-2.54 (m, 1H), 2.30-2.40 (m, 1H), 2.01-2.13 (m, 1H), 1.87-2.01 (m, 1H), 1.66 (s, 3H). |

The following compounds of formula (If) were prepared using a similar procedure to that described above for Example 1. For each compound, reference to a starting material is provided. This is provided merely for assistance to the skilled chemist. The starting material may not necessarily have been prepared from the batch referred to.

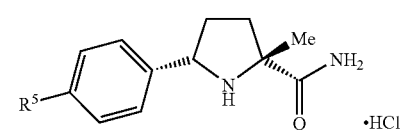

(If)

| No. | SM | R⁵ | Characterising data |
|---|---|---|---|
| E4 | D21 | benzoxy | R_t (HPLC): 3.59 min. MS: (ES/+) 311 m/z: [MH+]. C19H22N2O2 requires 310. ¹H NMR (400 MHz, DMSO-d₆) δ (ppm): 9.91 (br. s., 1H); 8.17 (br. s., 1H); 8.12 (s, 1H); 7.89 (s, 1H); 7.44 (d, 2H); 7.41 (d, 2H); 7.39 (t, 2H); 7.32 (t, 1H); 7.07 (d, 2H); 5.13 (s, 2H); 4.64-4.74 (m, 1H); 2.44-2.49 (m, 1H); 2.23- |

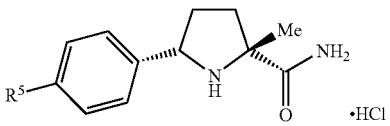

(If)

| No. | SM | R⁵ | Characterising data |
|---|---|---|---|
| | | | 2.32 (m, 1H); 2.00-2.09 (m, 1H); 1.84-1.94 (m, 1H); 1.65 (s, 3H). |
| E5 | D23 | 2-fluorobenzoxy | R_t (HPLC) 3.61 min; Chiral HPLC: Column: chiralpak AD-H 5 um, 250 × 4.6 mm, Mobile phase: A: n-Hexane; B: Ethanol, Gradient: isocratic 30% B, Flow rate: 0.8 ml/min, UV wavelength range: 200-400 nm, Analysis time: 20 min, ret. time: 16.3 min.; MS: (ES/+) 329 m/z: [MH+]. C19H21FN2O2 requires 328; ¹H NMR (500 MHz, DMSO-d₆) δ ppm 9.87 (br. s., 1H), 8.24 (br. s., 1H), 8.12 (s, 1H), 7.89 (s, 1H), 7.56 (t, 1H), 7.39-7.47 (m, 3H), 7.21-7.30 (m, 2H), 7.11 (d, 2H), 5.16 (s, 2H), 4.60-4.76 (m, 1H), 2.42-2.54 (m, 1H), 2.23-2.34 (m, 1H), 1.99-2.11 (m, 1H), 1.84-1.97 (m, 1H), 1.65 (s, 3H). |

The following compounds of formula (Ig) were prepared using a similar procedure to that described above for Example 1. For each compound, reference to a starting material (SM) is provided. This is provided merely for assistance to the skilled chemist. The starting material may not necessarily have been prepared from the batch referred to.

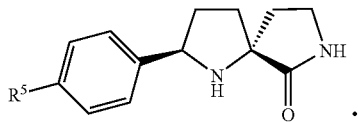

(Ig)

| No. | SM | R⁵ | Characterising Data |
|---|---|---|---|
| E6 | D26 | 2-fluorobenzoxy | R_t (HPLC) 3.61 min; MS: (ES/+) m/z: 341 [MH+]. C20H21FN2O2 requires 340; ¹H NMR (500 MHz, DMSO-d₆) δ (ppm): 10.37 (br. s, 1H), 8.78 (br. s, 1H), 8.42 (s, 1H), 7.53-7.58 (m, 1H), 7.54 (d, 2H), 7.42 (dd, 1H), 7.25 (t, 1H), 7.23 (t, 1H), 7.10 (d, 2H), 5.13-5.21 (m, 2H), 4.65-4.76 (m, 1H), 3.25-3.33 (m, 2H), 2.48-2.55 (m, 1H), 2.31-2.42 (m, 2H), 2.27-2.34 (m, 2H), 2.04-2.14 (m, 1H). |
| E7 | D27 | 2-cyanobenzoxy | R_t (HPLC) 3.37 min; MS: (ES/+) m/z: 348 [MH+]. C21H21N3O2 requires 347; ¹H NMR (500 MHz, DMSO-d₆) δ (ppm): 10.39 (br. s, 1H), 8.85 (br. s, 1H), 8.38 (s, 1H), 7.91 (d, 1H), 7.78-7.71 (m, 2H), 7.60-7.56 (m, 1H), 7.55 (d, 2H), 7.11 (d, 2H), 5.27 (s, 2H), 4.75-4.62 (m, 1H), 3.33-3.23 (m, 2H), 2.56-2.50 (m, 1H), 2.41-2.22 (m, 4H), 2.13-2.03 (m, 1H). |
| E8 | D28 | 2-cyanophenoxy | R_t (HPLC) 3.26 min; MS: (ES/+) m/z: 334 [MH+]. C20H19N3O2 requires 333; ¹H NMR (500 MHz, DMSO-d₆) δ (ppm): 10.73 (br. s, 1H), 8.96 (br. s, 1H), 8.44 (s, 1H), 7.93 (dd, 1H), 7.73-7.68 (m, 1H), 7.70 (d, 2H), 7.33 (t, |

-continued

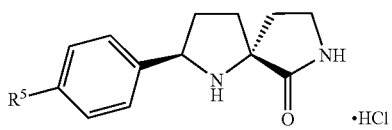

| No. | SM | R⁵ | Characterising Data |
|---|---|---|---|

1H), 7.22 (d, 2H), 6.99 (d, 1H), 4.85-4.75 (m, 1H), 3.34-3.25 (m, 2H), 2.65-2.51 (m, 1H), 2.45-2.27 (m, 4H), 2.16-2.06 (m, 1H).

E6 was also prepared as follows:

Example 6

(Procedure 2): (2R,5R)-2-(4-{[(2-Fluorophenyl)methyl]oxy}phenyl)-1,7-diazaspiro[4.4]nonan-6-one hydrochloride (E6)

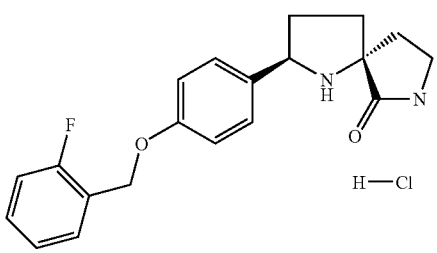

To a solution of 1,1-dimethylethyl (2R,5R)-2-(4-{[(2-fluorophenyl)methyl]oxy}phenyl)-6-oxo-1,7-diazaspiro[4.4]nonane-1-carboxylate (D26, 29.3 g) in AcOEt (325 mL) and MeOH (108 mL) at 0° C., was added acetyl chloride (28.5 mL). The resulting solution was stirred at 0° C. for 15 minutes then at ambient temperature for 16 hours. Solvent was evaporated (bath temperature: first ambient and then 38° C.) and the residue solid was triturated with Et₂O (3×244 mL). Finally the solid was collected by filtration and dried under high vacuum at 35° C. overnight to afford the title compound (23 g, Y=92%) as white solid.

¹H NMR (400 MHz, DMSO-d6) δ(ppm): 10.37 (t, 1H); 8.78 (t, 1H); 8.42 (s, 1H); 7.55 (m, 1H); 7.54 (d, 2H); 7.42 (dd, 1H); 7.25 (t, 1H); 7.23 (t, 1H); 7.10 (d, 2H); 5.17 (m, 2H); 4.70 (m, 1H); 3.29 (m, 2H); 2.52 (m, 1H); 2.37 (m, 2H); 2.31 (m, 2H); 2.09 (m, 1H).

Example 9

(2R,5R)-2-(4-{[(2-Fluorophenyl)methyl]oxy}phenyl)-7-methyl-1,7-diazaspiro[4.4]nonan-6-one hydrochloride (E9)

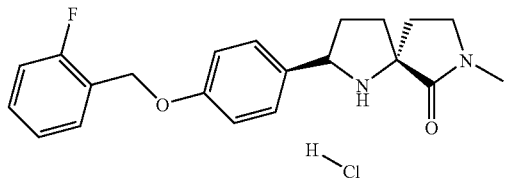

Procedure 1: To a solution of 1,1-dimethylethyl (2R,5R)-2-(4-{[(2-fluorophenyl)methyl]oxy}phenyl)-7-methyl-6-oxo-1,7-diazaspiro[4.4]nonane-1-carboxylate (D29, 61 mg, 0.134 mmol) in a mixture of ethyl acetate (1 ml) and methanol (0.1 ml) at 0° C. was added acetyl chloride (60 µl, 0.806 mmol). The mixture was stirred for 3 hours at room temperature. The solvent was removed under vacuum and the gummy solid was treated with Et₂O (3×2 ml) obtaining a white solid (53 mg). R$_t$ (HPLC): 3.72 min; MS: (ES/+) m/z: 355 [MH⁺]; C21H23FN2O2 requires 354; ¹H NMR (500 MHz, DMSO-d₆) δ (ppm): 10.58 (br. s., 1H), 8.87 (br. s., 1H), 7.59-7.52 (m, 3H), 7.47-7.39 (m, 1H), 7.31-7.20 (m, 2H), 7.11 (d, 2H), 5.17 (s, 2H), 4.80-4.66 (m, 1H), 3.43-3.37 (m, 2H), 2.81 (s, 3H), 2.59-2.23 (m, 5H), 2.13-2.03 (m, 1H).

E9 was also prepared as follows:

Procedure 2: The previous crude of (2R,5R)-2-(4-{[(2-fluorophenyl)methyl]oxy}phenyl)-7-methyl-1,7-diazaspiro[4.4]nonan-6-one (E10, 75.85 g) was stripped with Et₂O (2×150 mL), dissolved in DCM (150 mL) and 5-6M HCl in IPA (76 mL) was added at room temperature. Solvent and excess of HCl were evaporated and then stripped with Et₂O (2×76 mL) and DCM (2×76 mL) to get a foam. The foam was suspended in Et₂O (600 mL) and DCM (76 mL) and stirred overnight at room temperature. Finally the solid was collected, washed with a mixture of Et₂O/DCM 8/1 (3×76 mL) and dried under high vacuum at 40° C. overnight to afford the title compound (79 g).

¹H NMR (500 MHz, DMSO-d₆) δ(ppm): 10.58 (bs, 1H); 8.87 (bs, 1H); 7.55 (m, 3H); 7.43 (m, 1H); 7.25 (m, 2H); 7.11 (d, 2H); 5.17 (s, 2H); 4.73 (m, 1H); 3.40 (m, 1H); 2.81 (s, 3H); 2.60-2.20 (m, 5H); 2.08 (m, 1H).

Example 10

(2R,5R)-2-(4-{[(2-Fluorophenyl)methyl]oxy}phenyl)-7-methyl-1,7-diazaspiro[4.4]nonan-6-one (E10)

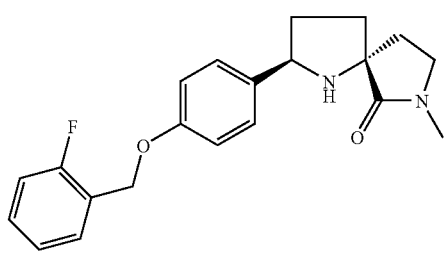

Procedure 1: The reaction was performed on the two separated batches of 1-(1,1-dimethylethyl) 2-methyl (2R,5R)-5-(4-{[(2-fluorophenyl)methyl]oxy}phenyl)-2-[2-(methylamino)ethyl]-1,2-pyrrolidinedicarboxylate resulting from Description 38. The first batch (80 g) was dissolved in MeOH (320 mL), 5-6N HCl in IPA (160 mL) was added and the mixture stirred overnight at 25° C. 13% aqueous NH₃ (200 mL) was added, cooling the reaction to 0° C. during addition, until complete conversion. EtOAc (320 mL), water (160 mL) and NaHCO₃ saturated solution (240 mL) were added and the phases separated. Aqueous phase was extracted with EtOAc (6×80 mL) and the organic phase was concentrated to about 400 mL then washed with brine (120 mL) which was back extracted with EtOAc (80 mL). The combined organic phases were dried over Na₂SO₄ and evaporated to dryness to afford the crude (50 g). The second batch (81 g) was dissolved in MeOH (324 mL), 5-6N HCl in IPA (162 mL) was added and the mixture stirred overnight at 25° C. Further 5-6N HCl in IPA (20 mL) was added and stirred for a further 6 hours. NaHCO₃ saturated solution (160 mL) and EtOAc (500 mL) were added followed by solid NaHCO₃ to pH~8. Phases were separated and the aqueous was back extracted with EtOAc (2×200 mL). Combined organics were concentrated to about 400 mL. DCM (300 mL) and brine (200 mL) were added, the phases were separated and the organic phase was dried over Na₂SO₄ and evaporated to dryness to afford crude (67 g). DCM (135 mL) was added and stirred overnight at room temperature then heated to reflux for 3 hours then cooled back to room temperature. 2M NH₃ in methanol (12.5 mL) was added due to incomplete cyclisation and then aqueous 13% NH₃ was added and stirred for at least 2 hours to reach complete cyclisation. Brine (100 mL) was added, phases were separated and organic was dried over Na₂SO₄ and evaporated to dryness to afford the crude (58 g).

The two crudes were combined and purified via chromatographic column (DCM/MeOH 25/1) to afford the title compound (85 g).

¹H NMR (600 MHz, DMSO-d₆) δ(ppm): 7.56 (dt, 1H); 7.41 (m, 3H); 7.25 (t, 1H); 7.23 (t, 1H); 6.97 (d, 2H); 5.12 (s, 2H); 4.18 (m, 1H); 3.28 (m, 1H); 3.21 (m, 1H); 2.77 (s, 3H); 2.50 (bs, 1H); 2.12 (m, 1H); 2.01 (m, 1H); 1.92 (m, 1H); 1.72 (m, 2H).

E10 was also obtained as follows:
Procedure 2: A mixture of 1-(1,1-dimethylethyl) 2-methyl (2R,5R)-5-(4-{[(2-fluorophenyl)methyl]oxy}phenyl)-2-[2-(methylamino)ethyl]-1,2-pyrrolidinedicarboxylate and 1,1-dimethylethyl (2R,5R)-2-(4-{[(2-fluorophenyl)methyl]oxy}phenyl)-7-methyl-6-oxo-1,7-diazaspiro[4.4]nonane-1-carboxylate (D86, 5.8 g) was dissolved in MeOH (23.2 mL), HCl in IPA (14.3% solution, 17.7 g) was added and the mixture stirred at 25° C. for 24 hours. 13% aqueous NH₃ (14.5 ml) and the mixture stirred for 4 hours. EtOAc (60 mL) and water (40 mL) were added and the phases separated. The aqueous phase was extracted with EtOAc (25 ml) then the combined organic phases were dried over Na₂SO₄ and evaporated to dryness to afford the crude (5.52 g). The crude was purified via column chromatography (EtOAc to 9:1 EtOAc/MeOH) to afford the title compound (2.1 g).

Example 11

(2R,5R)-2-(3-{[(2-Fluorophenyl)methyl]oxy}phenyl)-1,7-diazaspiro[4.4]nonan-6-one hydrochloride (E11)

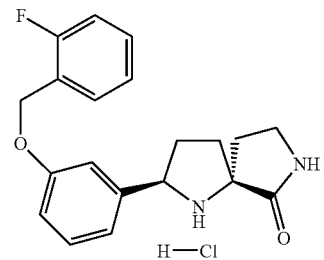

To a solution of 1,1-dimethylethyl (2R,5R)-2-(3-{[(2-fluorophenyl)methyl]oxy}phenyl)-6-oxo-1,7-diazaspiro[4.4]nonane-1-carboxylate (D46, 200 mg, 0.45 mmol) in dichloromethane (2 mL) cooled at 0° C., was added TFA (0.4 mL) dropwise and the ice-bath removed. After 1 h the solvent was evaporated under vacuum and the crude mixture purified by SCX column to give the title compound as the free base (154 mg, quant.); R$_t$ (HPLC) 3.58 min. The free base (77 mg, 0.23 mmol) was dissolved in dichloromethane (2.5 mL), and o the resulting solution cooled at 0° C. HCl (0.29 mL of a 1M solution in diethyl ether, 0.29 mmol) was added dropwise. After 15 min the solvent was removed under reduced pressure and the resulting solid triturated with diethyl ether to give the title compound (68 mg, 80%); R$_t$ (HPLC) 3.72 min. MS: (ES/+) m/z: 341 [MH⁺]; C20H21FN2O2 requires 340; ¹H NMR (500 MHz, DMSO-d₆) δ (ppm): 10.13 (br. s., 1H), 8.94 (br. s., 1H), 8.39-8.53 (m, 1H); 7.57 (t, 1H), 7.41-7.47 (m, 1H); 7.38 (t, 1H), 7.31-7.35 (m, 1H); 7.22-7.30 (m, 2H); 7.17 (d, 1H), 7.10 (d, 1H), 5.13-5.18 (m, 2H); 4.72 (br. s, 1H), 3.34-3.41 (m, 2H); 2.25-2.68 (m, 5H), 2.12 (br. s, 1H).

Example 12

(2R,5R)-2-(3-{[(2-Fluorophenyl)methyl]oxy}phenyl)-7-methyl-1,7-diazaspiro[4,4]nonan-6-one hydrochloride (E12)

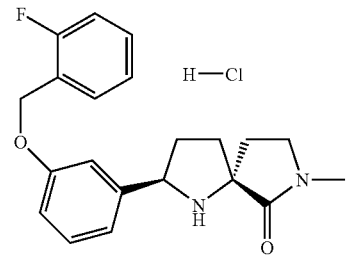

To a solution of 1,1-dimethylethyl (2R,5R)-2-(3-{[(2-fluorophenyl)methyl]oxy}phenyl)-7-methyl-6-oxo-1,7-diazaspiro[4.4]nonane-1-carboxylate (D47, 60 mg, 0.13 mmol) in a mixture of ethyl acetate (1 mL) and methanol (0.2 mL) was added AcCl (58 μl, 0.82 mmol) at 0° C. The mixture was stirred for 1 hour at room temperature, solvent removal afforded the title compound. Despite a clean HPLC trace, the product did not become solid. The oil obtained was then submitted to a further purification by SCX column. The free base coming from the SCX (40 mg, 0.11 mmol) was dissolved in dichloromethane (1 mL) and to this solution cooled at 0° C. HCl (0.15 mL of a 1M solution in diethyl ether, 0.15 mmol) was added. After 15 min the solvent was removed under reduced pressure and the solid obtained triturated with diethyl ether. The title compound was obtained as a white solid (40 mg, 80%); $R_t$ (HPLC) 3.72 min; MS: (ES/+) m/z: 355 [MH$^+$]; C21H23FN2O2 requires 354; $^1$H NMR (500 MHz, DMSO-$d_6$) δ (ppm): 10.62 (br. s., 1H), 9.00 (br. s., 1H), 7.59 (dt, 1H); 7.42-7.48 (m, 1H); 7.39 (t, 1H), 7.34-7.37 (m, 1H); 7.22-7.31 (m, 2H); 7.18 (d, 1H), 7.11 (dd, 1H); 5.11-5.24 (m, 2H), 4.70-4.80 (m, 1H); 3.35-3.45 (m, 2H); 2.78-2.86 (m, 3H); 2.50-2.56 (m, 2H); 2.24-2.46 (m, 3H); 2.00-2.18 (m, 1H).

Example 13

(2R,5R)-2-(4-{[(2-Fluorophenyl)methyl]oxy}phenyl)-1,7-diazaspiro[4.6]undec-9-en-6-one hydrochloride (E13)

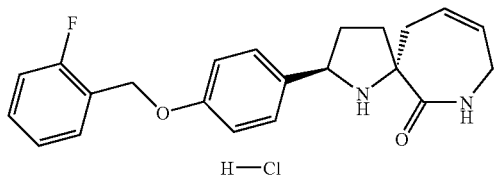

1-(1,1-Dimethylethyl) 2-methyl (2R,5R)-2-[(2Z)-4-bromo-2-buten-1-yl]-5-(3-{[(2-fluorophenyl)methyl]oxy}phenyl)-1,2-pyrrolidinedicarboxylate (D48, 80 mg, 0.14 mmol) was dissolved in a 7M solution of NH$_3$ in methanol (5 mL) and stirred at room temperature for 4 hours. The solvent was removed under vacuum and the oily residue dissolved in dichloromethane (8 mL) and cooled at 0° C. TFA (0.8 mL) was added dropwise and the reaction mixture allowed to warm to room temperature. After 1 hour the solvent was removed and the crude mixture purified by SCX column. At this stage the uncyclized allylic amine was dissolved in methanol (10 mL), NaOMe (50 mg, excess) was added and the heterogeneous mixture refluxed for 7 hours. Solvent removal followed by chromatography on silica gel using dichloromethane/methanol/triethylamine (98.0:1.5:0.5) gave the title compound as free base (25 mg, 48%); $R_t$ (HPLC) 3.93 min. MS: (ES/+) m/z: 367 [MH$^+$]; C22H23FN2O2 requires 366. The free base (25 mg, 0.07 mmol) was dissolved in dichloromethane (1 mL) and the solution cooled to 0° C. and HCl (0.10 mL of a 1M solution in diethyl ether, 0.10 mmol) was added. After 20 min the solvent was removed under reduced pressure and the solid obtained triturated with diethyl ether. The title compound was obtained as a white solid (20 mg, 73%); $R_t$ (HPLC) 3.93 min; MS: (ES/+) m/z: 367 [MH$^+$]; C22H23FN2O2 requires 366; 1H NMR (500 MHz, DMSO-d6) δ (ppm): 9.95 (br. s., 1H), 8.61 (d, 1H); 8.40 (br. s., 1H), 7.55 (t, 1H); 7.45 (d, 2H); 7.39-7.45 (m, 1H); 7.20-7.29 (m, 2H); 7.11 (d, 2H); 5.68-5.79 (m, 2H); 5.16 (s, 2H), 4.68-4.78 (m, 1H), 4.07 (d, 1H); 3.58-3.69 (m, 1H); 2.61-2.78 (m, 3H); 2.31-2.39 (m, 1H); 2.08-2.20 (m, 1H); 1.97-2.08 (m, 1H).

Example 14

(2R,5S)-2-(4-{[(2-Fluorophenyl)methyl]oxy}phenyl)-1,7-diazaspiro[4.5]decan-6-one hydrochloride (E14)

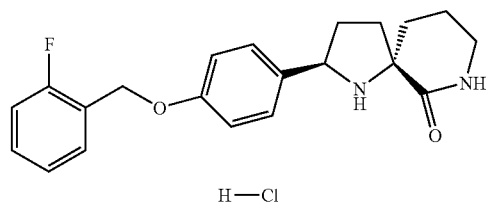

To a solution of 1,1-dimethylethyl (2R,5S)-2-(3-{[(2-fluorophenyl)methyl]oxy}phenyl)-6-oxo-1,7-diazaspiro[4.5]decane-1-carboxylate (D52, 20 mg, 0.044 mmol) in a mixture of ethyl acetate (0.5 mL) and methanol (30 μL) was added AcCl (19 μl, 6 eq) at 0° C. The mixture was stirred for 6 hours at room temperature. The mixture was evaporated to afford the title compound as a white solid (12 mg, 70%); $R_t$ (HPLC) 3.72 min; MS: (ES/+) m/z: 355 [MH$^+$]; C21H23FN2O2 requires 354; 1H NMR (500 MHz, DMSO-d6) δ (ppm): 7.58 (d, 2H), 7.51 (dt, 1H), 7.36 (dd, 1H), 7.06-7.23 (m, 2H), 7.10 (d, 2H), 5.18 (s, 2H), 4.66-4.77 (m, 1H); 3.35-3.49 (m, 2H), 2.59-2.76 (m, 1H), 2.47-2.57 (m, 1H), 2.32-2.40 (m, 1H), 2.18-2.34 (m, 3H), 1.95-2.08 (m, 2H).

Example 15

(2S,5S)-2-(4-{[(2-Fluorophenyl)methyl]oxy}phenyl)-1,7-diazaspiro[4.5]decan-6-one hydrochloride (E15)

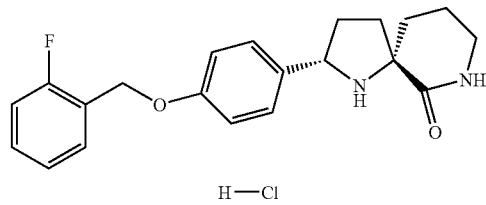

The title compound was prepared in quantitative yield by using a similar procedure to that described above in Example 14 using 1,1-dimethylethyl (2S,5S)-2-(3-{[(2-fluorophenyl)methyl]oxy}phenyl)-6-oxo-1,7-diazaspiro[4.5]decane-1-carboxylate (D53). $R_t$ (HPLC) 3.72 min; MS: (ES/+) m/z: 355 [MH+-HCl]; C21H23FN2O2 requires 354; 1H NMR (500 MHz, DMSO-$d_6$) δ (ppm): 7.49-7.61 (m, 3H), 7.43 (t, 1H), 7.13-7.29 (m, 3H), 6.93 (d, 1H), 5.27 (s, 2H), 4.84-5.14 (m, 1H); 3.12-3.67 (m, 2H), 2.46-2.71 (m, 4H), 2.26-2.37 (m, 1H), 2.00-2.25 (m, 3H).

Example 16

(5R)-5-[4-{[(2-Fluorophenyl)methyl]oxy}-3-(methyloxy)phenyl]-2-methyl-L-prolinamide hydrochloride (E16)

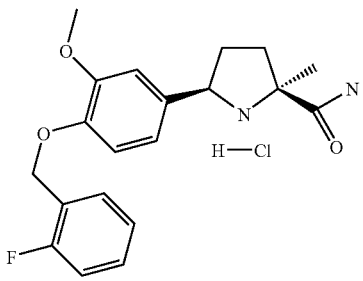

To a solution of 1,1-dimethylethyl (2S,5R)-2-(aminocarbonyl)-5-[4-{[(2-fluorophenyl)methyl]oxy}-3-(methyloxy)phenyl]-2-methyl-1-pyrrolidinecarboxylate (D61, 110 mg, 0.24 mmol) in a mixture of ethyl acetate (2.7 ml) and methanol (0.3 ml) at 0° C. was added AcCl (110 µl, 1.54 mmol). The mixture was stirred for 1 hour at room temperature. Two further additions of AcCl (110 µl and after 1 h another 110 µl plus additional stirring for 2 h) were required, before the reaction was complete (as shown by HPLC). The mixture was evaporated and the residue was triturated with Et$_2$O to afford the title compound as a white solid (80 mg, 84%); R$_t$ (HPLC) 3.41 min; MS: (ES/+) m/z: 359 [MH]+ C20H23FN2O3 requires 358; 1H NMR (500 MHz, DMSO-d6) δ (ppm): 9.82-10.05 (br.s, 1H); 8.02-8.27 (br.s, 1H); 8.05-8.10 (br.s, 1H); 7.80-7.90 (br.s, 1H); 7.47-7.53 (m, 1H); 7.35-7.43 (m, 1H); 7.17-7.24 (m, 2H); 7.15 (d, 1H); 7.07 (d, 1H); 6.95 (dd, 1H); 5.08 (s, 2H); 4.57-4.72 (m, 1H); 3.70-3.78 (s, 3H); 2.39-2.51 (m, 1H); 2.19-2.32 (m, 1H); 1.95-2.08 (m, 1H); 1.81-1.95 (m, 1H); 1.62 (s, 3H).

Example 17

(5R)-5-[4-{[(2-Fluorophenyl)methyl]oxy}-3-(methyloxy)phenyl]-2-[(methyloxy)methyl]-L-prolinamide hydrochloride (E17)

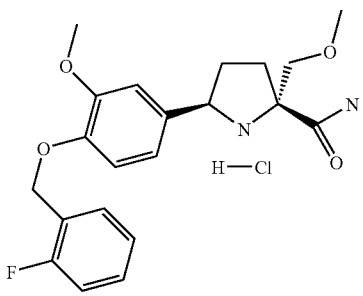

To a solution of 1,1-dimethylethyl (2R,5R)-2-(aminocarbonyl)-5-[4-{[(2-fluorophenyl)methyl]oxy}-3-(methyloxy)phenyl]-2-[(methyloxy)methyl]-1-pyrrolidinecarboxylate (D65, 70 mg, 0.14 mmol) in a mixture of ethyl acetate (1.8 ml) and methanol (0.2 ml) at 0° C. was added AcCl (170 µl, 2.38 mmol). The mixture was stirred for 4 hours at room temperature. The solvent was evaporated and the residue was triturated with Et$_2$O to afford the title compound as a white solid (49 mg, 82%); Rt (HPLC) 3.62 min; MS: (ES/+) m/z: 389 [MH]+ C21H25FN2O4 requires 388; 1H NMR (500 MHz, DMSO-d6) δ (ppm): 9.91-10.02 (br.s, 1H); 8.07-8.25 (br.s, 2H); 7.94-8.03 (br.s, 1H); 7.50 (t, 1H); 7.35-7.43 (m, 1H); 7.17-7.25 (m, 2H); 7.13 (s, 1H); 7.06 (d, 1H); 6.95 (dd, 1H); 5.08 (s, 2H); 4.51-4.66 (m, 1H); 3.92 (d, 1H); 3.74 (s, 3H); 3.69 (d, 1H); 3.26 (s, 3H); 2.17-2.35 (m, 2H); 1.97-2.12 (m, 1H); 1.79-1.96 (m, 1H).

Example 18

(5R)-5-(4-{[(2-Fluorophenyl)methyl]oxy}phenyl)-2-[(methyloxy)methyl]-L prolinamide hydrochloride (E18)

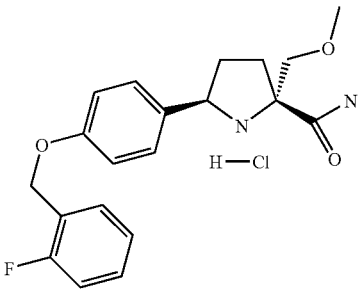

To a solution of 1,1-dimethylethyl (2R,5R)-2-(aminocarbonyl)-5-(4-{[(2-fluorophenyl)methyl]oxy}phenyl)-2-[(methyloxy)methyl]-1-pyrrolidinecarboxylate (D69, 400 mg, 0.87 mmol) in a mixture of ethyl acetate (9 ml) and methanol (1 ml) at 0° C. was added AcCl (400 µl, 5.60 mmol). The mixture was stirred for 2 hours at room temperature. Two further additions of AcCl (400 µl and after 2 h another 400 µl plus additional stirring for 2 h) were required, before the reaction was complete (as shown by HPLC). The mixture was evaporated and the residue was triturated with Et$_2$O to afford the title compound as a white solid (314 mg, 91%); R$_t$ (HPLC) 3.71 min; MS: (ES/+) m/z: 359 [MH]+ C20H23FN2O3 requires 358; 1H NMR (500 MHz, DMSO-d6) δ (ppm): 10.05-10.25 (br.s, 1H); 8.25 (s, 1H); 8.04-8.24 (br.s, 1H); 8.02 (s, 1H); 7.52-7.65 (m, 1H); 7.38-7.51 (m, 3H); 7.21-7.33 (m, 2H); 7.07-7.17 (m, 2H); 5.19 (s, 2H); 4.59-4.76 (br.s, 1H); 4.00 (d, 1H); 3.76 (d, 1H); 3.35 (s, 3H); 2.20-2.43 (m, 2H); 2.01-2.18 (m, 1H); 1.80-1.99 (m, 1H).

Example 19

(5R)-5-(4-{[(2-Fluorophenyl)methyl]oxy}phenyl)-2-(hydroxymethyl)-L-prolinamide hydrochloride (E19)

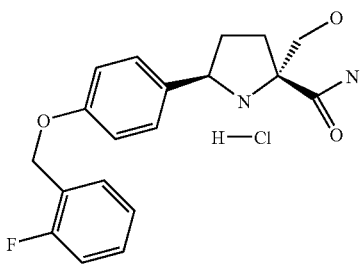

To a solution of (5R)-2-({[(1,1-dimethylethyl)(dimethyl)silyl]oxy}methyl)-5-(4-{[(2-fluorophenyl)methyl]oxy}phenyl)-L-prolinamide (D75, 50 mg, 0.11 mmol) in dry THF (2 ml) at 0° C. was added tetrabutyl ammonium fluoride (0.12 ml, 0.13 mmol, 1.1M solution in THF) in 5 min and the mixture was stirred for 1 h at the same temperature. The reaction was quenched with a 5% solution of NaHCO₃ and extracted with ethyl acetate. The organic layer was dried (Na₂SO₄) filtered and evaporated. The residue was purified by chromatography on silica gel using cyclohexane/ethyl acetate (1:1 to 0:1) to afford the title compound (free base) as a white solid (20 mg, 53%); $R_t$ (HPLC): 3.59 min; MS: (ES/+) m/z: 345 [MH+] C19H21FN2O3 requires 344.

To a solution of this solid, dissolved in dry ethyl ether (2 ml), was added HCl (80 µl, 0.08 mmol, 1M solution in Et₂O). The solvent was evaporated and the residue was triturated with Et₂O to afford the title compound as a white solid (22 mg, quantitative); $R_t$ (HPLC): 3.56 min; MS: (ES/+) m/z: 345 [MH+] C19H21FN2O3 requires 344; 1H NMR (500 MHz, DMSO-d6) δ(ppm): 7.40-7.82 (m, 1H); 7.49 (t, 1H); 7.38 (d, 2H); 7.31-7.40 (m, 1H); 7.13-7.22 (m, 2H); 7.01 (d, 2H); 5.13 (s, 2H); 4.41-4.60 (m, 1H); 3.86 (d, 1H); 3.72 (d, 1H); 2.10-2.27 (m, 2H); 1.95-2.13 (m, 1H); 1.65-1.94 (m, 1H).

NOTE: Individual signals of the acid protons, NH2 and OH were not observed

Example 20

(2S,5S)-2-(4-{[(2-Fluorophenyl)methyl]oxy}phenyl)-1,7-diazaspiro[4.4]nonan-6-one hydrochloride (E20)

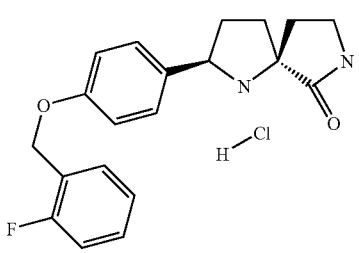

To a solution of 1,1-dimethylethyl (2S,5S)-2-(4-{[(2-fluorophenyl)methyl]oxy}phenyl)-6-oxo-1,7-diazaspiro[4.4]nonane-1-carboxylate (D79, 130 mg, 0.295 mmol) in a mixture of ethyl acetate (2.7 ml) and methanol (0.3 ml) at 0° C. was added AcCl (130 µl, 1.82 mmol). The mixture was stirred for 4 hours at room temperature. The solvent was evaporated and the residue was triturated with Et₂O to afford the title compound as a white solid (80 mg, 82%); $R_t$ (HPLC) 3.60 min; MS: (ES/+) m/z: 341 [MH+] C20H21FN2O2 requires 340; 1H NMR (500 MHz, DMSO-d6) δ(ppm): 10.37 (br. s, 1H), 8.78 (br. s, 1H), 8.42 (s, 1H), 7.53-7.58 (m, 1H), 7.54 (d, 2H), 7.42 (dd, 1H), 7.25 (t, 1H), 7.23 (t, 1H), 7.10 (d, 2H), 5.13-5.21 (m, 2H), 4.65-4.76 (m, 1H), 3.25-3.33 (m, 2H), 2.48-2.55 (m, 1H), 2.31-2.42 (m, 2H), 2.27-2.34 (m, 2H), 2.04-2.14 (m, 1H).

Example E21, E22

(5R,7R)-7-(4-{[(2-Fluorophenyl)methyl]oxy}phenyl)-2,6-diazaspiro[4.5]decan-1-one hydrochloride, (5S,7S)-7-(4-{[(2-Fluorophenyl)methyl]oxy}phenyl)-2,6-diazaspiro[4.5]decan-1-one hydrochloride (E21, E22)

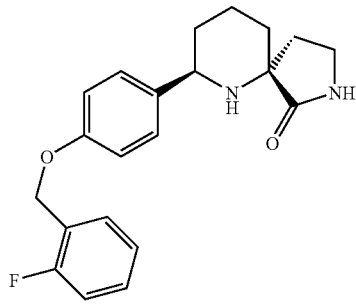

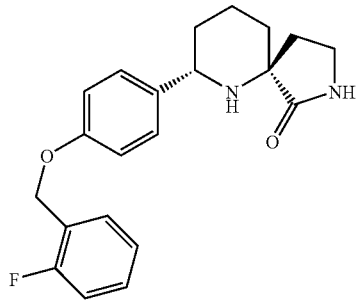

To a solution of racemic 2-methyl 1-(phenylmethyl)(2R,6R)-2-(cyanomethyl)-6-(4-{[(2-fluorophenyl)methyl]oxy}phenyl)-1,2-piperidinedicarboxylate (D84, 524 mg, 1.0 mmoles, 1 eq) in of MeOH (35 mL) was added Ni Raney in a catalytic quantity (1 spatula). The mixture was hydrogenated at 6 atm for 4.5 h. The crude compound was filtered, then solvent was removed under reduced pressure. The residue was dissolved in AcOEt and the organic phase was washed with a solution of NaOH 1M, dried over $Na_2SO_4$, filtered and evaporated to dryness. The crude compound was purified by flash chromatography on 10 g silica gel cartridge, using a gradient of DCM/MeOH 10/0 to 95/5 as an eluent, to give the free base of the title compound (42 mg, 12%) as a racemate. 1H-NMR (CDCl3, 400 MHz): δ 1144-1.55 (m, 1 H), 1.55-1.64 (m, 1 H), 1.64-1.72 (m, 1 H), 1.72-1.80 (m, 1 H), 1.89 (d, 1 H), 1.94-2.02 (m, 1 H), 2.21-2.31 (m, 1 H), 2.37-2.45 (m, 1 H), 3.31 (dd, 1 H), 3.42 (t, 1 H), 3.67 (d, 1H), 5.13 (s, 2 H), 5.70 (br. s., 1 H), 6.94 (d, 2 H), 7.08 (t, 1 H), 7.15 (t, 1 H), 7.29 (d, 2 H), 7.31 (t, 1 H), 7.49 (t, 1 H). LC-MS [Supelcosil ABZ+Plus, 33×4.6 mm, 3 μm, gradient: A: $H_2O$+0.1% HCOOH/B: $CH_3CN$: 0% to 95% B in 3 min., 95% B for 1 min., 95% B to 0% B in 0.1 min., flow rate: 2 mL/min]. $R_t$=1.44 min (100%) (m/z=355 $(M+H)^+$).

The enantiomeres were separated by chiral HPLC [chiralcel od (25×2) cm. Mobile phase: n-Hexane/Ethanol 60/40%. Flow rate: 0.8 mL/min, UV detection: 220 nm]. Solvents were removed under reduced pressure. The resulting compounds were dissolved in $Et_2O$. Then a solution of HCl 1M in $Et_2O$ was added dropwise. Supernatant was removed and the precipitate was dried under high vacuum to give example E21 (13 mg) and example E22 (8 mg). The absolute stereochemistry has not been assigned.

Chiral HPLC [Supelcosil ABZ+Plus, 33×4.6 mm, 3 μm, gradient: A: $H_2O$+0.1% HCOOH/B: $CH_3CN$: 0% to 95% B in 3 min., 95% B for 1 min., 95% B to 0% B in 0.1 min., flow rate: 2 mL/min]:

enantiomer 1 (E21): $R_t$=6.8 min. (100% ee)
enantiomer 2 (E22): $R_t$=12.8 min (97.6% ee)

Example 23

(2R,5R)-2-(4-{[(2-fluorophenyl)methyl]oxy}phenyl)-7-methyl-1,7-diazaspiro[4.4]nonan-6-one 4-methylbenzenesulfonate (E23)

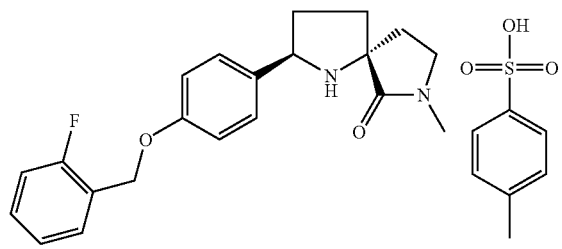

The compound (2R,5R)-2-(4-{[(2-fluorophenyl)methyl]oxy}phenyl)-7-methyl-1,7-diazaspiro[4.4]nonan-6-one hydrochloride (E9, 57.2 g) was suspended in EtOAc (286 mL) and $NaHCO_3$ saturated solution (229 mL) was added. The layers were separated and the organic layer was dried over $Na_2SO_4$.

The salt was filtered off and washed with EtOAc (3×57 mL).

The solvent was evaporated under reduced pressure and the crude stripped with acetone (2×171 mL), giving 52.7 g of (2R,5R)-2-(4-{[(2-fluorophenyl)methyl]oxy}phenyl)-7-methyl-1,7-diazaspiro[4.4]nonan-6-one.

This compound was dissolved in acetone (520 mL) and the solution was heated to 40° C.

A solution of p-toluenesulfonic acid monohydrate (27.84 g) in acetone (260 mL) was added in 30 min.

A solid precipitated after the addition of approx 50 mL of this solution.

The mixture was stirred at 40° C. for 4.5 h and then cooled to room temperature.

The solid was collected, washed with acetone (3×230 mL) and dried under high vacuum for 16 hours obtaining the Form 1 crystals of the title compound (70.1 g).

1H NMR (400 MHz, DMSO-d6) δ(ppm): 9.90 (bs, 1H); 8.91 (bs, 1H); 7.55 (m, 3H); 7.48 (m, 2H); 7.43 (m, 1H); 7.25 (m, 2H); 7.11 (m, 4H); 5.18 (s, 2H); 4.73 (dd, 1H); 3.41 (m, 2H); 2.82 (s, 3H); 2.36 (m, 5H); 2.29 (s, 3H); 2.11 (m, 1H).

Unique and discriminating peaks of Form 1 of Example 23 have been identified and are illustrated in the table below:

| Position [°2Th.] | d-spacing [Å] |
|---|---|
| 6.8 | 13.0 |
| 8.7 | 10.2 |
| 10.8 | 8.2 |
| 12.7 | 7.0 |
| 13.6 | 6.5 |
| 14.6 | 6.1 |
| 17.3 | 5.1 |
| 17.8 | 5.0 |
| 18.3 | 4.8 |
| 20.4 | 4.4 |
| 21.0 | 4.2 |
| 22.0 | 4.0 |
| 22.6 | 3.9 |
| 23.1 | 3.8 |
| 24.1 | 3.7 |
| 24.6 | 3.6 |
| 25.0 | 3.6 |
| 27.2 | 3.3 |
| 27.8 | 3.2 |
| 28.1 | 3.2 |
| 28.7 | 3.1 |
| 29.3 | 3.0 |
| 29.6 | 3.0 |
| 30.2 | 3.0 |
| 34.6 | 2.6 |
| 35.4 | 2.5 |
| 36.1 | 2.5 |
| 44.5 | 2.0 |

Melting point: 233° C.

Example 24

(2R,5R)-2-(4-{[(2-fluorophenyl)methyl]oxy}phenyl)-1,7-diazaspiro[4.4]nonan-6-one (E24)

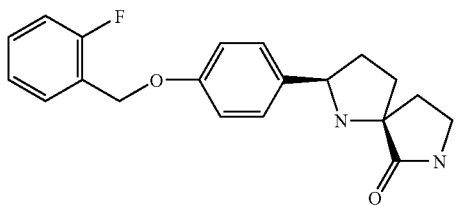

1,1-Dimethylethyl (2R,5R)-2-(4-{[(2-fluorophenyl)methyl]oxy}phenyl)-6-oxo-1,7-diazaspiro[4.4]nonane-1-carboxylate (D26, 30 mg) was dissolved in dry DCM (1.5 ml). At 0° C. TFA (0.4 ml) was added and the mixture was stirred at room temperature for 1 h. The mixture was evaporated and the residue purified via a SCX cartridge affording the title compound (23 mg) as a yellowish oil. $R_t$ (HPLC) 3.61 min; MS: (ES/+) m/z: 341 [MH+]. C20H21FN2O2 requires 340.

Biological Assay

Na Channel Assay Protocol

The ability of the compounds of the invention to modulate the voltage-gated sodium channel subtype NaV1.3 may be determined by the following assay.

Cell Biology

Stable cell lines expressing hNaV1.3 channels were created by transfecting CHO cells with the pCIN5-hNav1.3 vector using the lipofectamine (Invitrogen) transfection method. pCIN5 is a bicistronic vector for the creation of mammalian cell lines that predisposes all neomycin resistant cells to express recombinant protein (see Rees S., Coote J., Stable J., Goodson S., Harris S. & Lee M. G. (1996) Biotechniques, 20, 102-112) by virtue of the recombinant cDNA being linked to the neomycin-selectable marker cDNA downstream of the CMV promoter (for full details see Chen Y H, Dale T J, Romanos M A, Whitaker W R, Xie X M, Clare J J. Cloning, distribution and functional analysis of the type III sodium channel from human brain Eur J Neurosci, 2000 December; 12, 4281-9). Cells were cultured in Iscove's modified Dulbecco's medium (Invitrogen) containing, 10% fetal bovine serum, 1% L-glutamine, 1% Penicillin-Streptomycin (Invitrogen), 1% non-essential amino acids, 2% H-T supplement and 1% G418 (Invitrogen) and maintained at 37° C. in a humidified environment containing 5% CO2 in air. Cells were liberated from the T175 culture flask for passage and harvesting using Versene (Invitrogen).

Cell Preparation

Cells were grown to 60-95% confluence in a T75 flask. Cells were lifted by removing the growth media and incubating with 1.5 ml of warmed (37° C.) Versene (Invitrogen, 15040-066) for 6 min. Lifted cells were suspended in 10 ml of PBS (Invitrogen, 14040-133). Cell suspension was then placed into a 10-ml centrifuge tube and centrifuged for 2 min at 700 rpm. After centrifugation, the supernatant was removed and the cell pellet was resuspended in 3 ml of PBS.

Electrophysiology

Currents were recorded at room temperature (21-23° C.) using the IonWorksHT planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential of −90 mV to 0 mV were applied for 20 ms and repeated 10 times at a frequency of 10 Hz. In all experiments, the test pulse protocol was performed in the absence (pre-read) and presence (post-read) of a compound. Pre- and post-reads were separated by a compound addition followed by a 3-3.5 min incubation.

Solutions and Drugs

The intracellular solution contained the following (in mM): K-gluconate 100, KCl 40 mM, MgCl2 3.2, EGTA 3, HEPES 5, adjusted to pH 7.25. Amphotericin was prepared as 30 mg/ml stock solution and diluted to a final working concentration of 0.1 mg/ml in internal buffer solution. The external solution was Dulbecco's PBS (Invitrogen) and contained the following (in mM): CaCl2 0.90, KCl 2.67, K3PO4 1.47, MgCl2 0.50, NaCl 138, Na3PO4 8.10, with a pH of 7.4. Compounds were prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analysed and filtered using both seal resistance (>40 MΩ) and peak current amplitude (>200 pA) in the absence of compound to eliminate unsuitable cells from further analysis. Paired comparisons between pre-drug and post-drug additions were used to determine the inhibitory effect of each compound. The concentrations of compounds required to inhibit current elicited by the $1^{st}$ depolarising pulse by 50% (tonic pIC50) were determined by fitting of the Hill equation to the concentration response data. In addition the use-dependent inhibitory properties of the compounds were determined by assessing the effect of compounds on the $10^{th}$ versus $1^{st}$ depolarising pulse. The ratio of the $10^{th}$ over $1^{st}$ pulse was calculated in the absence and presence of drug and the % use-dependent inhibition calculated. The data was fitted using the same equation as for the tonic $pIC_{50}$ and the concentration producing 15% inhibition (use-dependent $pUD_{15}$) calculated.

The compounds of Examples 1 to 9, 11 to 22 were tested in the above assay and gave $pUD_{15}$ values of 4.5 or greater.

Monoamine Oxidase-B Assay Protocol

The protocol describes the assay for testing MAO-B inhibition. It is a fluorescence-based end-point assay using benzylamine as substrate. Oxidation of the substrate by MAO-B leads to hydrogen peroxide release, and this product is then utilised by peroxidase to convert non-fluorescent Amplex Red(™) into fluorescent resorufin. The global reaction is:

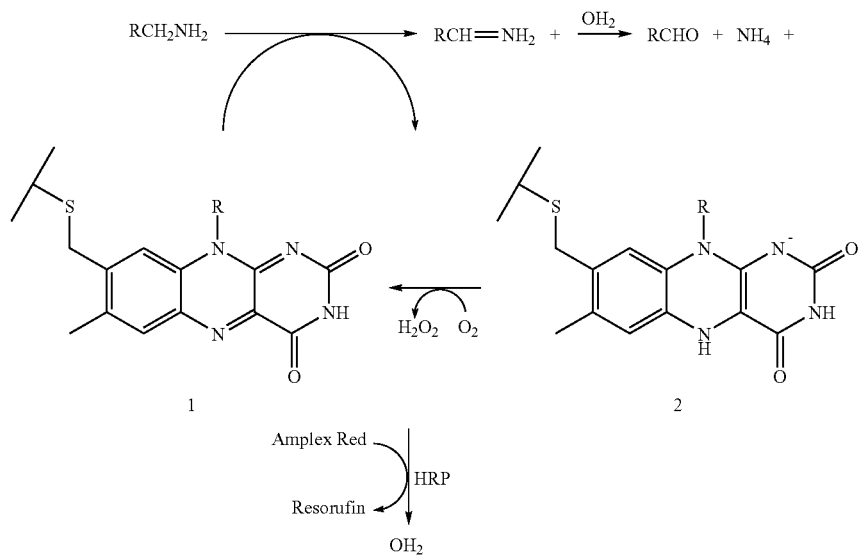

Thus inhibition of the enzyme by a test compounds leads to reduced fluorescence.

The assay uses human recombinant monoamine oxidase B that is present in microsomes from baculovirus infected insect cells (Supplied by Sigma). Compounds are tested over a range of concentrations in order to determine the concentration that causes half-maximal inhibition of the enzyme activity in the assay (IC50). Pargyline (Sigma) is used as a positive control in the assay, giving an IC50 in the range 0.4-2 µM.

Dispense 0.1 µl of test compound in neat DMSO in black low volume Greiner 384-well plate. Add 5 µl of substrate solution (400 µM benzylamine (Sigma), 50 µM Amplex Red (Molecular Probes), 50 mM potassium phosphate, pH 7.4). Add 5 µl of the assay buffer (50 mM potassium phosphate, pH 7.4) to blank wells. Add 5 µl of the enzyme solution (0.23 IU/ml human recombinant monoamine oxidase B, 1 IU/ml horseradish peroxidase type XII (Sigma), 50 mM potassium phosphate, pH 7.4) to remaining wells. Shake to ensure proper mixing. Incubate for 60 minutes at room temperature in darkness. Read fluorescence using Analyst/Gemini (Molecular Devices; Resorufin: Ex530/Em580/Dichr561 (Analyst)—Ex555/Em590/Cutoff570 (Gemini)).

The effect of a given compound is calculated as:

% Inh=100×[(data−control1)/(control2−control1)], where control1 corresponds to the enzyme showing its maximum activity (i.e., not inhibited) and control2 corresponds to minus enzyme fluorescence in absence of HRP.

The invention claimed is:

1. The compound (2R,5R)-2-(4-{[(2-fluorophenyl)methyl]oxy}phenyl)-7-methyl-1,7-diazaspiro[4.4]nonan-6-one or a pharmaceutically acceptable salt thereof.

2. The compound of claim 1, wherein said compound is (2R,5R)-2-(4-{[(2-fluorophenyl)methyl]oxy}phenyl)-7-methyl-1,7-diazaspiro[4.4]nonan-6-one.

3. The compound of claim 1, wherein said compound is (2R,5R)-2-(4-{[(2-fluorophenyl)methyl]oxy}phenyl)-7-methyl-1,7-diazaspiro[4.4]nonan-6-one tosylate.

4. A pharmaceutical composition comprising a compound as claimed in claim 1, and a pharmaceutically acceptable carrier therefor.

5. A method of treating depression or a mood disorder in a mammal comprising administering an effective amount of a compound according to claim 1.

6. A method of treating a bipolar disorder in a mammal comprising administering an effective amount of a compound according to claim 1.

7. A process to prepare a compound as claimed in claim 1, comprising reacting a compound of formula (XXII), wherein n is zero, q is 1, X is C, $R^2$ is methyl, $R^6$ is H, $R^5$ is —$OCH_2R^7$ wherein $R^7$ is 2-fluorophenyl, and R is $C_{1-3}$alkyl

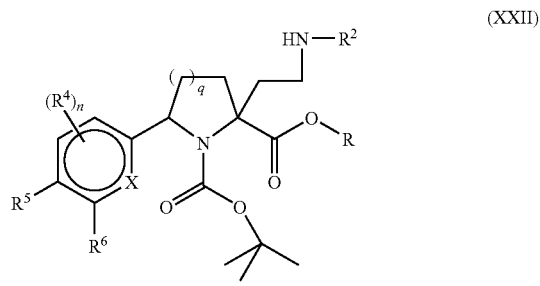

(XXII)

with a solution of hydrochloric acid in a suitable solvent followed by treatment with a suitable base.

8. A method of treating compulsive eating disorder or binge eating disorder in a in a mammal, said method comprising administering a compound according to claim 1.

9. The method according to claim 8 wherein said mammal is a human.

10. A method of treating epilepsy in a mammal comprising administering an effective amount of a compound according to claim 1.

11. The method according to claim 10 wherein said mammal is a human.

12. The method according to claim 5 wherein said mammal is a human.

13. The method according to claim 6 wherein said mammal is a human.

14. A pharmaceutical composition comprising a compound as claimed in claim 3 and a pharmaceutically acceptable carrier therefor.

15. A method of treating depression or a mood disorder in a mammal comprising administering an effective amount of a compound according to claim 3.

16. The method according to claim 15, wherein said mammal is a human.

17. A method of treating a bipolar disorder in a mammal comprising administering an effective amount of a compound according to claim 3.

18. The method according to claim 17, wherein said mammal is a human.

19. A method of treating compulsive eating disorder or binge eating disorder in a mammal comprising administering an effective amount of a compound according to claim 3.

20. A method according to claim 19 wherein the mammal is human.

21. A method of treating epilepsy in a mammal comprising administering an effective amount of a compound according to claim 3.

22. A method according to claim 21 wherein the mammal is human.

\* \* \* \* \*